(12) United States Patent
Dillingham

(10) Patent No.: US 10,806,608 B2
(45) Date of Patent: *Oct. 20, 2020

(54) PROSTHETIC METHOD AND APPARATUS

(71) Applicant: iFIT Prosthetics, LLC, Pewaukee, WI (US)

(72) Inventor: Timothy R. Dillingham, Merion Station, PA (US)

(73) Assignee: iFit Prosthetics, LLC, Pewaukee, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/222,375

(22) Filed: Dec. 17, 2018

(65) Prior Publication Data

US 2019/0110910 A1 Apr. 18, 2019

Related U.S. Application Data

(63) Continuation-in-part of application No. 15/171,081, filed on Jun. 2, 2016, now abandoned, which is a
(Continued)

(51) Int. Cl.
*A61F 2/80* (2006.01)
*A61F 2/78* (2006.01)
(Continued)

(52) U.S. Cl.
CPC .............. *A61F 2/80* (2013.01); *A61F 2/5046* (2013.01); *A61F 2/54* (2013.01); *A61F 2/60* (2013.01);
(Continued)

(58) Field of Classification Search
CPC ..... A61F 2/7812–2002/785; A61F 2002/5026; A61F 2002/5027; A61F 2002/7875
See application file for complete search history.

(56) References Cited

U.S. PATENT DOCUMENTS

| 1,090,881 A | 3/1914 | Rowley |
| 4,161,042 A | 7/1979 | Cottingham et al. |

(Continued)

FOREIGN PATENT DOCUMENTS

| EP | 0395630 B1 | 10/1993 |
| EP | 1656911 A1 | 5/2006 |

(Continued)

OTHER PUBLICATIONS

Written Opinion and international Search Report dated Mar. 29, 2013 in related International Patent Application No. PCT/US2012/060168.

(Continued)

*Primary Examiner* — David H Willse
(74) *Attorney, Agent, or Firm* — Caesar Rivise, PC

(57) ABSTRACT

A method of placing a prosthetic system over a residual limb, said method comprising the steps of: providing the prosthetic system; and placing an outer shell of the prosthetic system on the residual limb having an above-knee amputation, the outer shell at least partially surrounds the residual limb, an outer side and an inner side of the outer shell on opposite sides of the residual limb, an upper edge of the outer side above a greater trochanter, the inner side below a lowest edge of an ischium without being directly below the lowest edge of the ischium.

32 Claims, 50 Drawing Sheets

Related U.S. Application Data continuation-in-part of application No. 14/466,227, filed on Aug. 22, 2014, now Pat. No. 10,398,577, which is a continuation-in-part of application No. 14/050,739, filed on Oct. 10, 2013, now Pat. No. 8,845,755, which is a continuation-in-part of application No. 13/274,146, filed on Oct. 14, 2011, now abandoned, which is a continuation-in-part of application No. 13/083,403, filed on Apr. 8, 2011, now Pat. No. 8,491,667, and a continuation-in-part of application No. 13/274,130, filed on Oct. 14, 2011, now Pat. No. 8,470,050.

(51) Int. Cl.
*A61F 2/50* (2006.01)
*A61F 2/76* (2006.01)
*A61F 2/60* (2006.01)
*A61F 2/54* (2006.01)

(52) U.S. Cl.
CPC ............. *A61F 2/76* (2013.01); *A61F 2/78* (2013.01); *A61F 2/7812* (2013.01); *A61F 2/7843* (2013.01); *A61F 2/601* (2013.01); A61F 2002/502 (2013.01); A61F 2002/5015 (2013.01); A61F 2002/5018 (2013.01); A61F 2002/5023 (2013.01); A61F 2002/5026 (2013.01); A61F 2002/5027 (2013.01); A61F 2002/5083 (2013.01); A61F 2002/546 (2013.01); A61F 2002/608 (2013.01); A61F 2002/762 (2013.01); A61F 2002/7635 (2013.01); A61F 2002/785 (2013.01); A61F 2002/7818 (2013.01); A61F 2002/7856 (2013.01); A61F 2002/7862 (2013.01); A61F 2002/7875 (2013.01); A61F 2002/7881 (2013.01)

(56) References Cited

U.S. PATENT DOCUMENTS

| | | | |
|---|---|---|---|
| 4,302,856 A | 12/1981 | May | |
| 4,872,879 A | 10/1989 | Shamp | |
| 4,988,360 A * | 1/1991 | Shamp | A61F 2/80 623/33 |
| 5,108,455 A | 4/1992 | Telikicherla | |
| 5,314,497 A | 5/1994 | Fay et al. | |
| 5,425,782 A | 6/1995 | Phillips | |
| 5,443,526 A | 8/1995 | Hoerner | |
| 5,529,575 A | 6/1996 | Klotz | |
| 5,571,209 A | 11/1996 | Brown, Sr. | |
| 5,651,792 A * | 7/1997 | Telikicherla | A61F 2/60 602/63 |
| 5,728,165 A | 3/1998 | Brown, Sr. | |
| 5,728,170 A | 3/1998 | Becker et al. | |
| 5,755,812 A | 5/1998 | Becker et al. | |
| 5,888,233 A | 3/1999 | Randstrom | |
| 5,888,234 A | 3/1999 | Littig | |
| 5,941,912 A | 8/1999 | Taylor et al. | |
| 6,051,026 A | 4/2000 | Biedermann et al. | |
| 6,267,787 B1 | 7/2001 | Capper et al. | |
| 6,368,357 B1 | 4/2002 | Schon et al. | |
| 6,398,817 B1 | 6/2002 | Hellberg et al. | |
| 6,402,789 B1 | 6/2002 | Gramnas | |
| 6,440,173 B1 | 8/2002 | Meyer | |
| 6,576,022 B2 | 6/2003 | Meyer et al. | |
| 6,689,171 B2 | 2/2004 | Slemker et al. | |
| 6,797,008 B1 | 9/2004 | Arbogast et al. | |
| 6,942,703 B2 | 9/2005 | Carstens | |
| 6,991,657 B1 | 1/2006 | Price, Jr. | |
| 7,083,654 B2 | 8/2006 | Helenberger et al. | |
| 7,300,466 B1 * | 11/2007 | Martin | A61F 2/605 623/31 |
| D617,460 S | 6/2010 | Okuda et al. | |
| 7,867,286 B2 | 1/2011 | Einarsson | |
| 2002/0116789 A1 | 8/2002 | McDevitt | |
| 2003/0023320 A1 | 1/2003 | Laghi | |
| 2003/0065403 A1 | 4/2003 | Meyer et al. | |
| 2003/0233151 A1 | 12/2003 | Lund | |
| 2005/0271462 A1 | 12/2005 | Curtis | |
| 2005/0278038 A1 | 12/2005 | Ikeda | |
| 2007/0260328 A1 | 11/2007 | Bertels et al. | |
| 2009/0043402 A1 | 2/2009 | Slemker | |
| 2010/0036505 A1 | 2/2010 | Hassler | |
| 2010/0191348 A1 * | 7/2010 | Kettwig | A61F 2/78 623/33 |
| 2010/0274364 A1 | 10/2010 | Pacanowsky et al. | |
| 2011/0015761 A1 | 1/2011 | Celebi et al. | |
| 2011/0071647 A1 | 3/2011 | Mahon | |

FOREIGN PATENT DOCUMENTS

| | | | |
|---|---|---|---|
| GB | 2 103 490 A * | 2/1983 | A61F 2/80 |
| GB | 2169207 A | 7/1986 | |
| GB | 2274994 A | 8/1994 | |
| JP | 08089519 A | 4/1996 | |
| RU | 2088182 C1 | 8/1997 | |
| WO | 98/43559 A1 | 10/1998 | |
| WO | 2006103430 A1 | 10/2006 | |

OTHER PUBLICATIONS

Written Opinion and International Search Report dated Mar. 15. 2013 in related International Patent Application No. PCT/US/2012/060166.
JP 7-155343 A (Jun. 20, 1995) English language translation.
Press Release entitled "Surefoot Announces Release of 3 New Custom Ski Boot Liners: The Surefoot Contoura X4, X4 Pro & C2", dated Aug. 14, 2014, Park City, UT, http://www.surefoot.com/SurefootCustomLiner.php, pp. 1-3.
Sidas Training Process—Injected Liner, https://www.youtube.com/watch?v+mrO9YhwNKo published Sep. 8, 2015.
Office Action dated May 23, 2019 in related U.S. Appl. No. 14/440,227.
Office Action dated Mar. 14, 2019 in related U.S. Appl. No. 15/171,081.

* cited by examiner

35

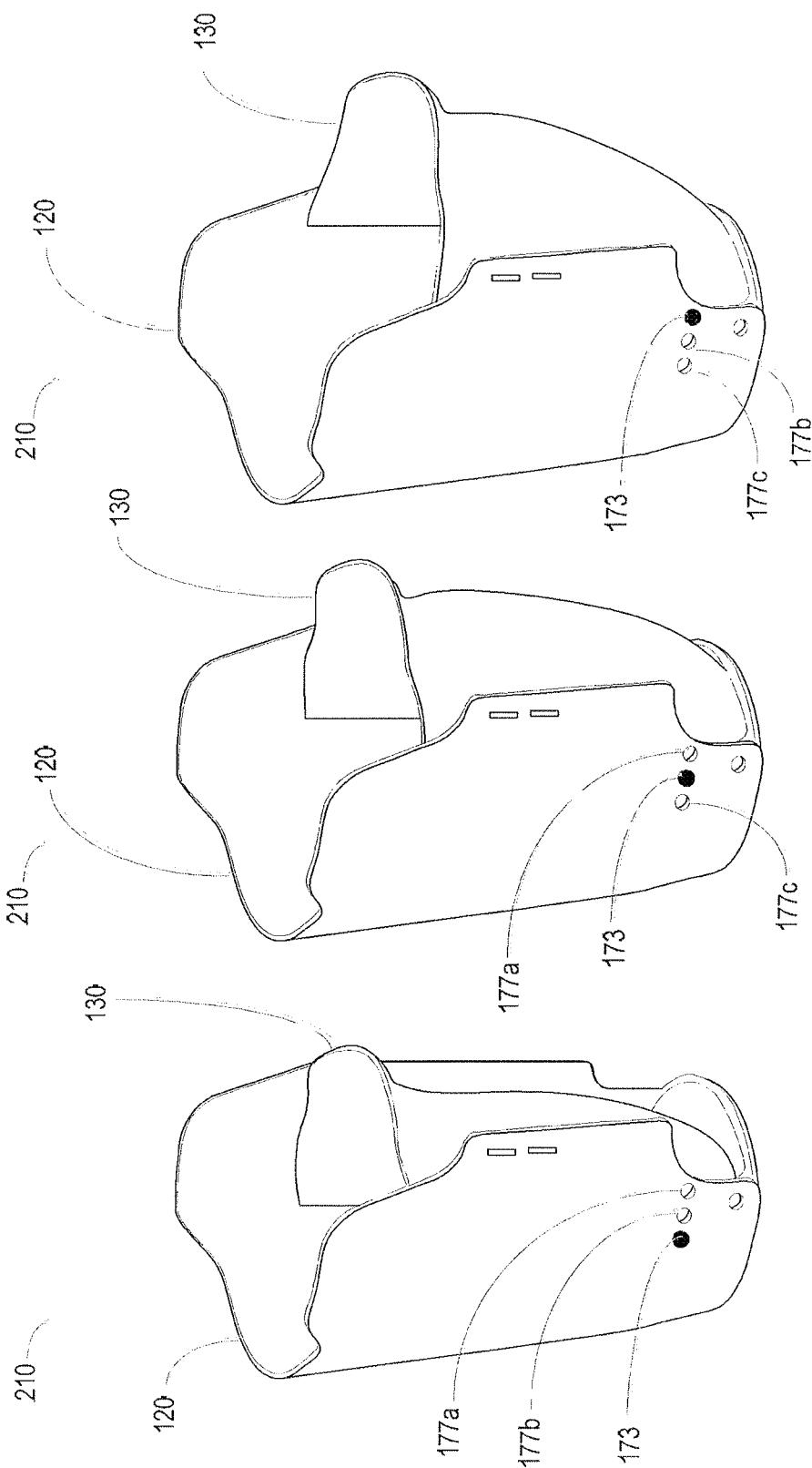

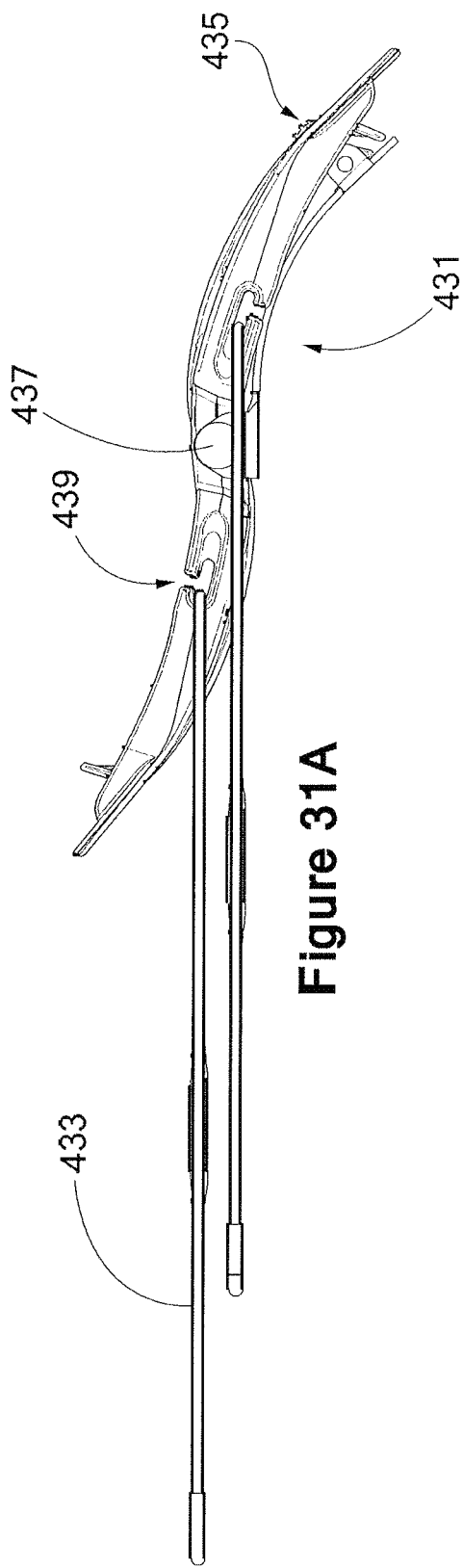
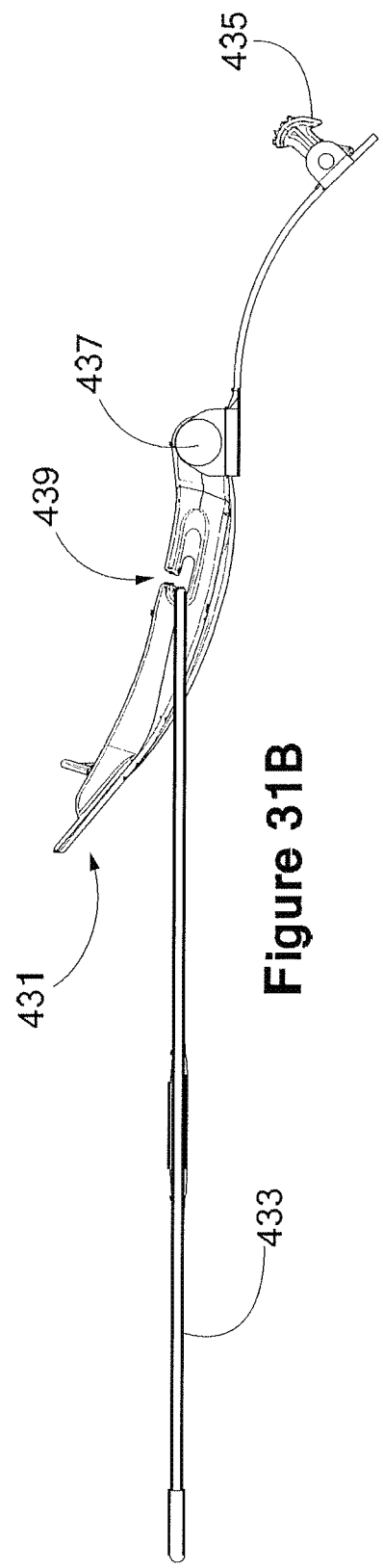
Figure 31A
Figure 31B

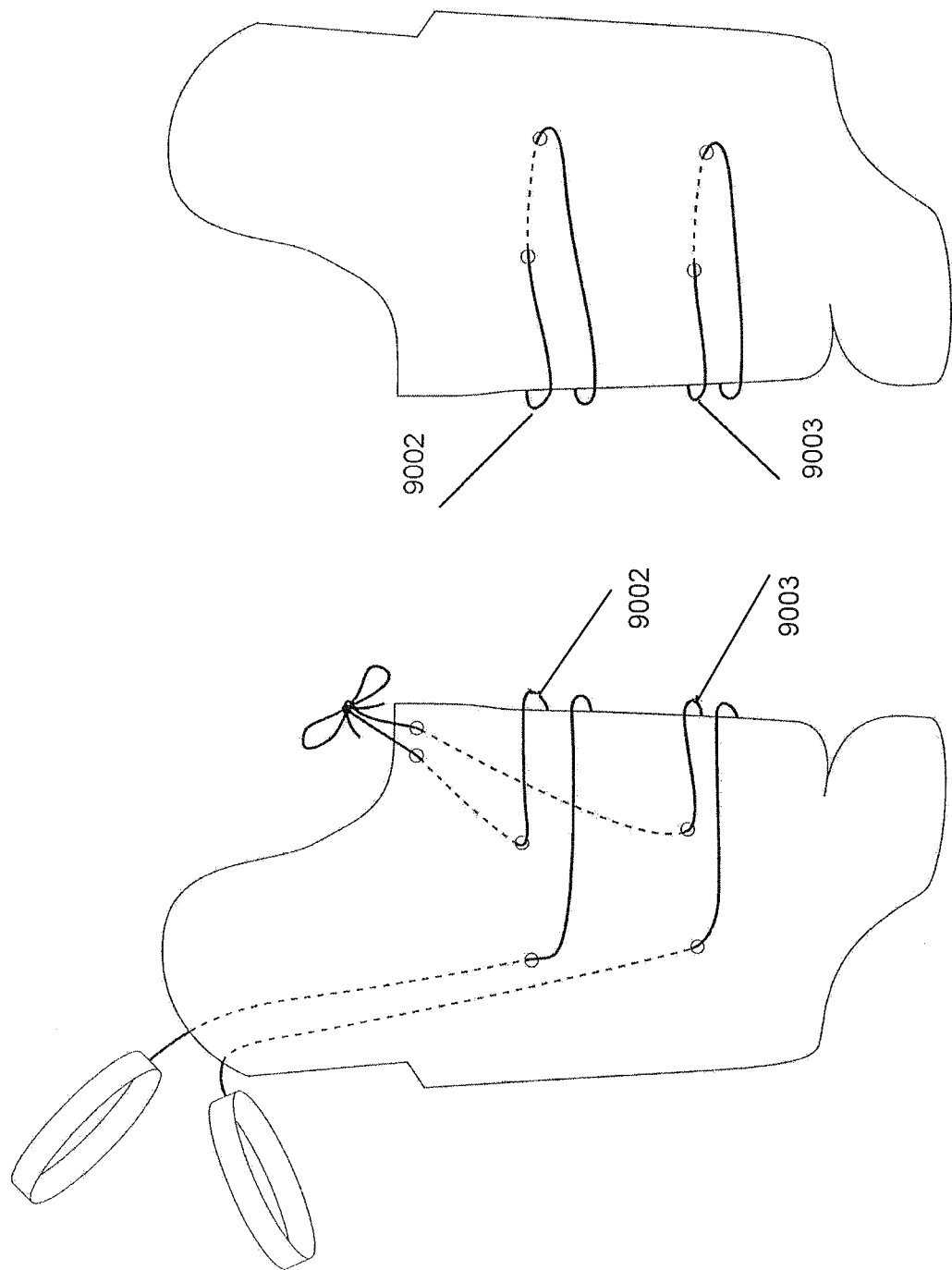

PROSTHETIC METHOD AND APPARATUS

CROSS-REFERENCE TO RELATED APPLICATIONS

This application is a continuation-in-part of U.S. patent application Ser. No. 15/171,081, filed on Jun. 2, 2016, now abandoned, which is a continuation-in-part of U.S. patent application Ser. No. 14/466,227, filed on Aug. 22, 2014, now U.S. Pat. No. 10,398,577, which is a continuation-in-part of U.S. patent application Ser. No. 14/050,739, entitled "Modular Prosthetic Devices and Prosthesis System," filed on Oct. 10, 2013, now U.S. Pat. No. 8,845,755, which is a continuation-in-part of U.S. patent application Ser. No. 13/274,146, entitled "Above-the Knee Modular Prosthesis System," filed on Oct. 14, 2011, now abandoned, which is a continuation-in-part of U.S. patent application Ser. No. 13/083,403 entitled "Modular Prosthesis System," filed on Apr. 8, 2011, now U.S. Pat. No. 8,491,667, and a continuation-in-part of U.S. patent application Ser. No. 13/274,130, entitled "Rapid Fit Modular Prosthetic Device for Accommodating Gait Alignment and Residual Limb Shape and Volume," filed on Oct. 14, 2011, now U.S. Pat. No. 8,470,050, the entire disclosures of which are hereby expressly incorporated by reference herein, and this application claims priority benefit of each and all of the aforesaid earlier filed patent applications.

STATEMENT REGARDING FEDERALLY SPONSORED RESEARCH OR DEVELOPMENT

This invention(s) was made with government support under NIH Grant 2R42HD069067-02 and 2SB1 AG050430-06 awarded by the National Institutes of Health. The government has certain rights in the invention(s).

FIELD OF INVENTION

The present invention(s) relates to the field of prostheses, and more particularly to modular prosthetic devices and prosthesis systems which accommodate gait alignment and residual limb shape and volume.

BRIEF DESCRIPTION OF THE DRAWINGS

Applicant's systems and devices will be described by way of example with reference to the accompanying drawings, in which:

FIGS. 17a, 17b, 17c illustrate the adjustability of an exemplary embodiment of a rear limb engaging member for a rapid fit modular prosthetic device for accommodating gait alignment and residual limb shape and volume.

FIG. 31A illustrates a perspective view of an exemplary embodiment of a buckle and a cable that may be used as a closure component for a modular prosthetic device/prosthesis system.

FIG. 31B illustrates another perspective view of the buckle and the cable shown in FIG. 31A.

FIGS. 46 and 47 are respective side views of an exemplary embodiment of the present invention that illustrates the use of an optional pull cord.

GLOSSARY

Figure 1:
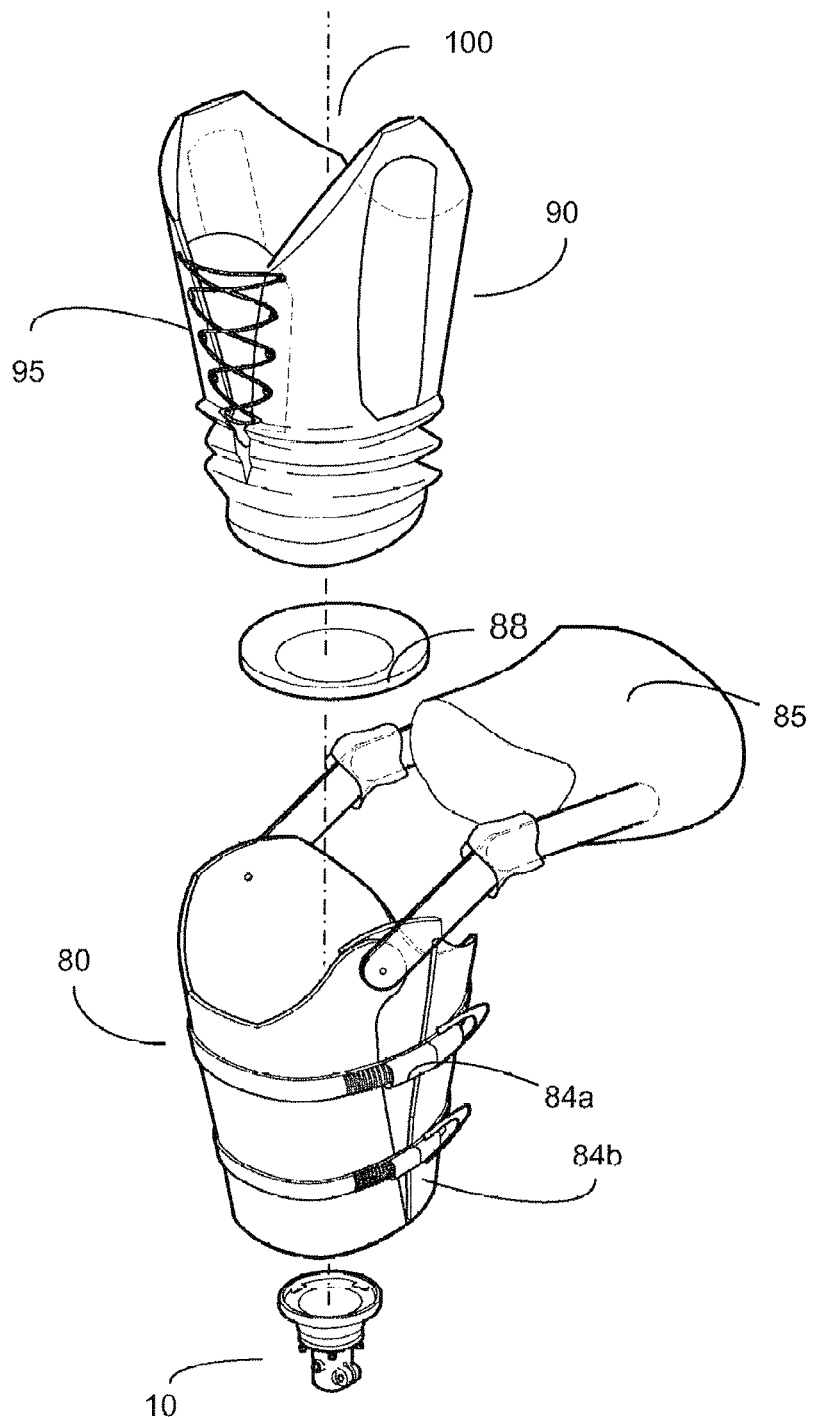
FIG. 1 illustrates an exploded view of an exemplary embodiment of a modular prosthesis system.

As used herein, the term "closure component" refers to any component which adjusts for the circumference of a residual limb to secure an outer housing.

As used herein, the term "connector tube" refers to any off-the-shelf 27-50 millimeter tube known in the art for use with a prosthetic limb, such as SAFETY KNEE.

As used herein, the term "deformable" means any structure with accommodating features for comfort and/or to reduce impact. Deformable materials may include, but are not limited to, padding, foam, cushioning, gel, rubber and any other malleable, moldable or adjustable material or combinations of materials known in the art.

As used herein, the term "dynamic stress point profile" refers to the unique anatomic and physiologic characteristics of an amputee's residual limb which govern the distribution of forces and stresses on the residual limb during activity.

As used herein, the term "flexible" means able to bend repeatedly without damage or breaking.

As used herein, the term "gait" means an individual's walking pattern, including all forces which could impact a residual limb.

As used herein, the term "grid pattern" refers to a configuration of uniformly repeating shapes arranged in a network of uniformly spaced horizontal and perpendicular lines.

As used herein, the term "modular" refers to components that are interchangeable and designed to function together as a unit. Components of a modular prosthesis system may be off-the-shelf or custom-made.

As used herein, the term "modular prosthesis system" refers to a prosthesis system comprised of components that are interchangeable and designed to function together as a unit. Components of a modular prosthesis system may be off-the-shelf or custom-made.

As used herein, the term "off-the-shelf knee joint" refers to a standard connector tube type prosthetic knee joint having an approximately 30 millimeter pipe which is commercially available. An off-the-shelf knee joint may be a low-cost foot and knee joint component known in the art that only needs to be adjusted for height.

As used herein, the term "pivotal side joints" refers to components of a suspension system that allow an amputee to bend his or her knee while wearing the prosthesis. Pivotal side joints may be comprised of one or more straight, curved, or irregular-shaped components. The components of a multi-component pivotal side joint are connected at a pivot point, the location of which may vary.

As used herein, the term "shank" refers to a component, such as a tubular component, attached to a connector or knee mechanism at one end and to another component, such as a prosthetic foot, at the other end.

As used herein, the term "supporting component" refers to a component which provides additional foundation for bearing the weight of a central plate and an upper assembly of a connector as well as the weight of an amputee.

As used herein, the term "washer" refers to a component which distributes pressure from another component and provides a firm attachment through friction to prevent movement of the component. For example, a washer placed under a threaded fastener will distribute the pressure from the head of the fastener and prevent movement of the fastener.

BACKGROUND

Over 150,000 amputations occur in the United States annually. Amputations are rising in frequency due to diabetes and peripheral vascular disease. The transtibial level of amputation is the most frequently performed.

A transtibial amputation is an amputation of the lower limb below the knee. A transtibial prosthesis is an artificial limb that replaces the portion of the leg below the knee that is missing. The shape of the residual limb varies for each individual and generally requires a custom-fitted prosthesis. A custom-fitted prosthesis that is comfortable is difficult to fabricate and is costly. Custom prostheses are typically formed out of hard rigid materials that have no adjustability.

The transfemoral (above knee) level of amputation is less common than the below knee (transtibial) level of limb loss, but results in the highest level of gait dysfunction and disability. Further, the transfemoral level is difficult to fit with a prosthetic socket due to redundant soft tissues and variable lengths and sizes of the residual limb.

A transfemoral prosthesis is an artificial limb that replaces the portion of the leg above the knee that is missing. The shape of the residual limb varies for each individual and generally requires a custom-fitted prosthesis. A comfortable custom-fitted prosthesis is difficult to fabricate and costly to provide using conventional manufacturing techniques.

The initial cost of a conventional prosthesis for a transtibial amputee typically ranges from about $6,000 to about $14,000. In addition, there are additional costs to ensure the comfort and functionality of the device.

The initial cost of a conventional prosthesis for a transfemoral amputee typically ranges from $10,000 to $20,000 depending upon the components used and the difficulty in fitting the individual. In addition, there are additional costs to ensure the comfort and functionality of the device including replacement or revision of the socket.

Insurance coverage of such prosthetic devices is variable across insurers and has often impeded prescription and availability of high quality devices even for amputees with insurance coverage. The uninsured often go without comfortable prosthetic devices for long periods of time before public insurance enables them to receive a functional prosthesis.

The present state of prosthesis fabrication often requires three or more visits to the prosthetist and there are multiple steps in the fabrication process. First, a cast mold of the residual limb is made and a positive cast that resembles the residual limb is generated. Then, a prosthetic socket is built to custom-fit over the positive cast. Sometimes a check or temporary socket is made to insure a better fit. Typical fabrication techniques require specialized facilities. Generally, the final prosthesis requires post-fabrication adjustments as the residual limb tissue changes over time. Patients are given multiple layers of socks to place on over the limb to accommodate volume and shape changes in the residual limb. Conventionally made sockets are rigid and fixed in volume and shape and do not conform or accommodate any changes in the person's residual limb.

Recent advancements have been made in the field of prosthetic devices. However, devices such as computerized knee mechanisms and energy storing feet are costly and beyond the economic means of many prosthetic users, particularly those in nations outside the United States.

Attempts have been made in the prior art to develop prosthesis systems that can be globally manufactured and distributed. These prosthesis systems, however, have several limitations. They are difficult to fabricate and require specialized facilities for initial manufacturing (e.g., casting) and subsequent adjustments. These systems all require expertise and consulting support that is not widely available. In particular, the socket (i.e., the portion of the prosthesis into which the residual limb fits), socket attachment, and alignment aspects of the device seem to be a common problematic area of development.

It is desirable to create a prosthetic device which eliminates the need for complex fabrication and specialized tools or labs, and which can be economically manufactured and distributed on a global basis.

It is desirable to create a prosthetic device which is immediately fit and aligned on the residual limb during the initial clinical visit and is adjustable and modular to accommodate different residual limb sizes and volume fluctuations that frequently occur in patients after amputation or those with heart failure and renal diseases.

It is desirable to create a prosthetic device which is one size and adjustable to fit many shapes.

BRIEF SUMMARY

There are various aspects of Applicant's adjustable prosthesis system, and many variations of each aspect.

One aspect is an adjustable prosthesis system for a residual limb. The system includes an adjustable outer shell, at least one closure component, an inner liner, and an adjustable connector. The adjustable outer shell has a bottom, an adjustable inner volume, and an adjustable inner shape, each of the adjustable inner volume and the adjustable inner shape having a width. The at least one closure component is attached to the adjustable outer shell and is adapted to adjust the width of at least one of the adjustable inner volume and the adjustable inner shape of the adjustable outer shell. The inner liner is adapted to receive the residual limb and to be inserted into the adjustable inner volume of the adjustable outer shell. The adjustable connector includes an upper plate, a lower plate, and a plurality of connecting fasteners. The upper plate is adapted to adjustably connect to the adjustable outer shell. The lower plate is below the upper plate and adapted to adjustably connect to the upper plate and to a shank or an other prosthetic device. The connecting fasteners are adapted to adjustably connect the lower plate to the upper plate. The adjustable connector has a proximal end adjustably connected to a distal end of the adjustable outer shell and is adapted to provide concurrently for a plurality of directional adjustments and/or angular adjustments of the position of the distal end of the adjustable outer shell relative to the proximal end of the adjustable connector while the adjustable outer shell is on the residual limb. The distal end of the adjustable connector is adapted to connect to a shank or an other prosthetic device. Adjustment of the width of at least one of the adjustable inner volume and the adjustable inner shape of the adjustable outer shell and adjustment of the adjustable connector together provide for a custom-like fit on the residual limb of the adjustable prosthesis system accounting for a plurality of differences in at least some of residual limb shape, circumference, volume, angle, general size, and other properties, as well as a plurality of differences in at least some of gait, bone structure, bone curvature, and bone alignment among a plurality of amputees.

In a first variation of the adjustable prosthesis system, the adjustable outer shell includes a first limb engaging panel and a second limb engaging panel pivotally connected to the first limb engaging panel. In a variant of this variation, at least a portion of the first limb engaging panel is rigid and at least a portion of the second limb engaging panel is not rigid.

In another variation of the adjustable prosthesis system, the adjustable outer shell includes a first flap having a first extended end and a second flap opposite the first flap and having a second extended end. At least a portion of the first flap overlaps at least a portion of the second flap so that at least a portion of the first extended end is on top of the second flap and at least a portion of the second extended end is under the first flap. In a variant of this variation, the first flap has a lateral length that is longer than a lateral length of the second flap.

In another variation of the adjustable prosthesis system, the at least one closure component is selected from a group consisting of buttons, snaps, clasps, clips, elastic components, buckles, laces, ties, interlocking components, hook-and-loop fasteners, hook-and-eye fasteners, hook-shaped components, looped wires, straps, and combinations thereof.

In another variation of the adjustable prosthesis system, at least a portion of the adjustable outer shell is rigid. In another variation, at least a portion of the inner liner is deformable.

In yet another variation of the adjustable prosthesis system, the adjustable connector is releasably attached to the adjustable outer shell.

In yet another variation of the adjustable prosthesis system, the directional adjustments are selected from a group consisting of a forward adjustment, a backward adjustment, a side-to-side adjustment, a rotational adjustment, and combinations thereof.

In another variation of the adjustable prosthesis system, at least one of the connecting fasteners is part of a rocker bolt assembly.

In yet another variation of the adjustable prosthesis system, at least a portion of a lower surface of the upper plate is textured and at least a portion of the upper surface of the lower plate is textured.

In another variation, at least a portion of the bottom surface of the upper plate is convex and at least a portion of an upper surface of the lower plate is concave and is adapted to receive at least part of the convex portion of the bottom surface of the upper plate.

In still yet another variation of the adjustable prosthesis system, a connection of the shank to the lower plate is enhanced by a modification of the shank to increase friction. In a variant of this variation, the modification is selected from a group consisting of knurling, applying carbon paste, indenting with a set screw, and combinations thereof.

A second adjustable prosthesis system is similar to the first adjustable prosthesis system or any of the variations discussed above, but includes at least one stiffening member attached to at least a portion of the adjustable outer shell.

A third adjustable prosthesis system is similar to the first adjustable prosthesis system or any of the variations discussed above, but includes a suspension system connected to the adjustable outer shell.

A fourth adjustable prosthesis system is similar to the first adjustable prosthesis system or any of the variations discussed above, but includes at least one adjustment component selected from a group consisting of a height adjustment component, a volume adjustment component, an angle adjustment component, a circumference adjustment component, and combinations thereof.

A fifth adjustable prosthesis system is similar to the first adjustable prosthesis system or any of the variations discussed above, but includes a pin suspension system with a locking pin. A variant of this variation includes a locking mechanism to lock and unlock the locking pin at a desired position. A variant of that variant includes a base plate adapted to guide the locking pin to a location adjacent the locking mechanism.

A sixth adjustable prosthesis system is similar to the first adjustable prosthesis system or any of the variations discussed above, but includes a first stiffening member on a first side of the adjustable outer shell, and a second stiffening member on a second side of the adjustable outer shell substantially opposite the first side. A proximal end of the adjustable outer shell extends above a knee portion of the residual limb, and a proximal end of the inner liner extends above the proximal end of the adjustable outer shell. The at least one closure component applies a force that moves the first and second stiffening members toward each other and moves an inner side of the adjustable outer shell and an inner side of the inner liner toward the residual limb, whereby at least a portion of the proximal end of the inner liner grasps the residual limb above the knee portion of the residual limb. In a variation of this system, the at least one closure component includes a buckle and a cable. In a variant of that variation, the buckle includes a locking mechanism or a safety latch.

A seventh adjustable prosthesis system is similar to the sixth adjustable prosthesis system or any of the variations thereof, but includes a hook mechanism connected to an outer side of the adjustable outer shell, and the at least one closure component includes a buckle connected to the outer side of the outer shell, the buckle being adapted to removably connect with the hook mechanism.

Another aspect is an adjustable connector for a prosthesis system. The adjustable connector includes an upper plate, a lower plate below the upper plate, and at least one rocker bolt assembly. The upper plate is adapted to adjustably connect to a component of the prosthesis system adjacent a residual limb. The lower plate is adapted to adjustably connect to the upper plate and to a shank or an other prosthetic device below the lower plate. The at least one rocker bolt assembly includes a plurality of connecting fasteners adapted to adjustably connect the lower plate to the upper plate thereby providing for an adjustable connection between the component of the prosthesis system adjacent the residual limb and the shank or an other prosthetic device. The adjustable connection provides for a concurrently made plurality of directional adjustments and/or angular adjustments of a position of the component of the prosthesis system relative to the shank or an other prosthetic device while the component of the prosthesis system is on the residual limb.

In a first variation of the adjustable connector, at least a portion of a lower surface of the upper plate is textured and at least a portion of the upper surface of the lower plate is textured.

In another variation of the adjustable connector, at least a portion of a bottom surface of the upper plate is convex and at least a portion of an upper surface of the lower plate is concave and adapted to receive at least part of the convex portion of the bottom surface of the upper plate.

Yet another aspect is an adjustable connector for a prosthesis system. The adjustable connector includes an upper plate, a lower plate below the upper plate, and at least one rocker bolt assembly. The upper plate is adapted to adjustably connect to a component of the prosthesis system adjacent a residual limb. The lower plate is adapted to adjustably connect to the upper plate and to a shank or an other prosthetic device below the lower plate. At least a portion of a bottom surface of the upper plate is convex and at least a portion of an upper surface of the lower plate is concave and adapted to receive at least part of the convex portion of the bottom surface of the upper plate. The at least one rocker bolt assembly includes a plurality of connecting fasteners adapted to adjustably connect the lower plate to the upper plate, thereby providing for an adjustable connection between the component of the prosthesis system adjacent the residual limb and the shank or an other prosthetic device. The adjustable connection provides for a concurrently made plurality of directional adjustments and/or angular adjustments of a position of the component of the prosthesis system relative to the shank or an other prosthetic device while the component of the prosthesis system is on the residual limb. The directional adjustments are selected from a group consisting of a forward adjustment, a backward adjustment, a side-to-side adjustment, a rotational adjustment, and combinations thereof.

In a variation of the adjustable connector, at least a portion of a lower surface of the upper plate is textured and at least a portion of an upper surface of the lower plate is textured.

DETAILED DESCRIPTION

For the purpose of promoting an understanding of the present invention(s), references are made in the text to exemplary embodiments of modular prosthesis systems and of modular prosthetic devices for accommodating gait alignment and residual limb shape and volume, only some of which are described herein. It should be understood that no limitations on the scope of the invention(s) are intended by describing these exemplary embodiments. One of ordinary skill in the art will readily appreciate that alternate but functionally equivalent materials, components, and designs may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention(s).

It should be understood that the drawings are not necessarily to scale; instead, emphasis has been placed upon illustrating the principles of the invention(s). In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

Figure 10:
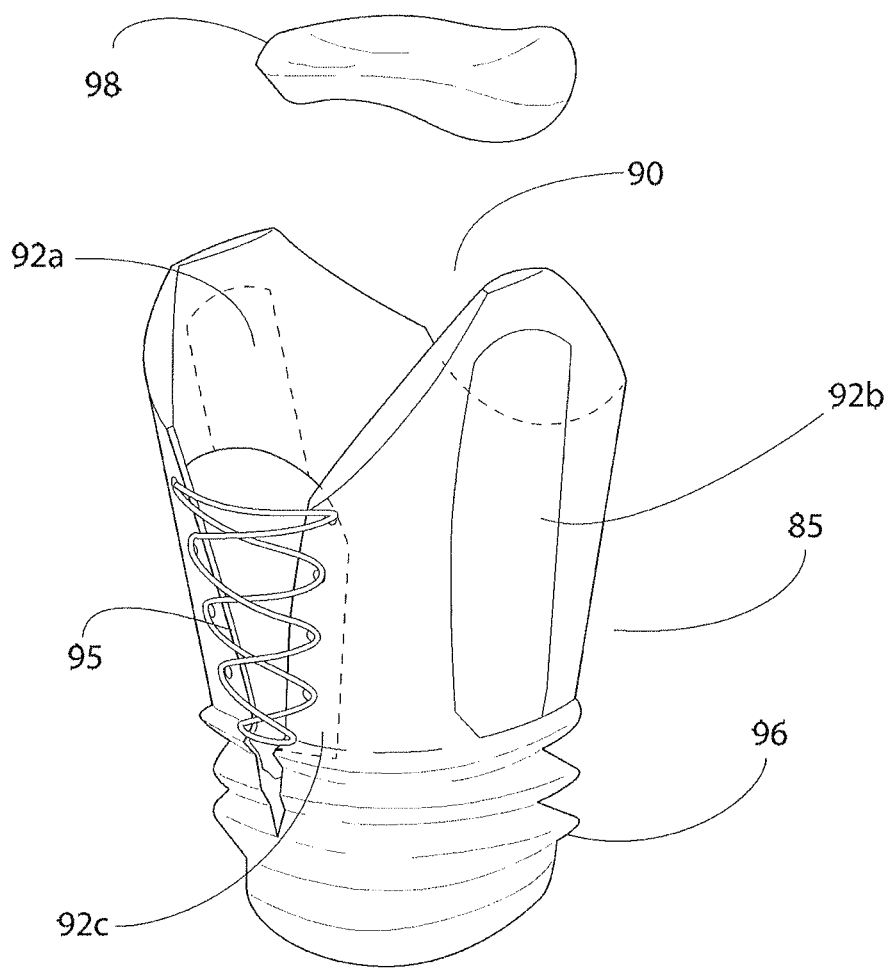
FIG. 10 illustrates a perspective view of an exemplary embodiment of a liner for a modular prosthesis system.
Figure 11:
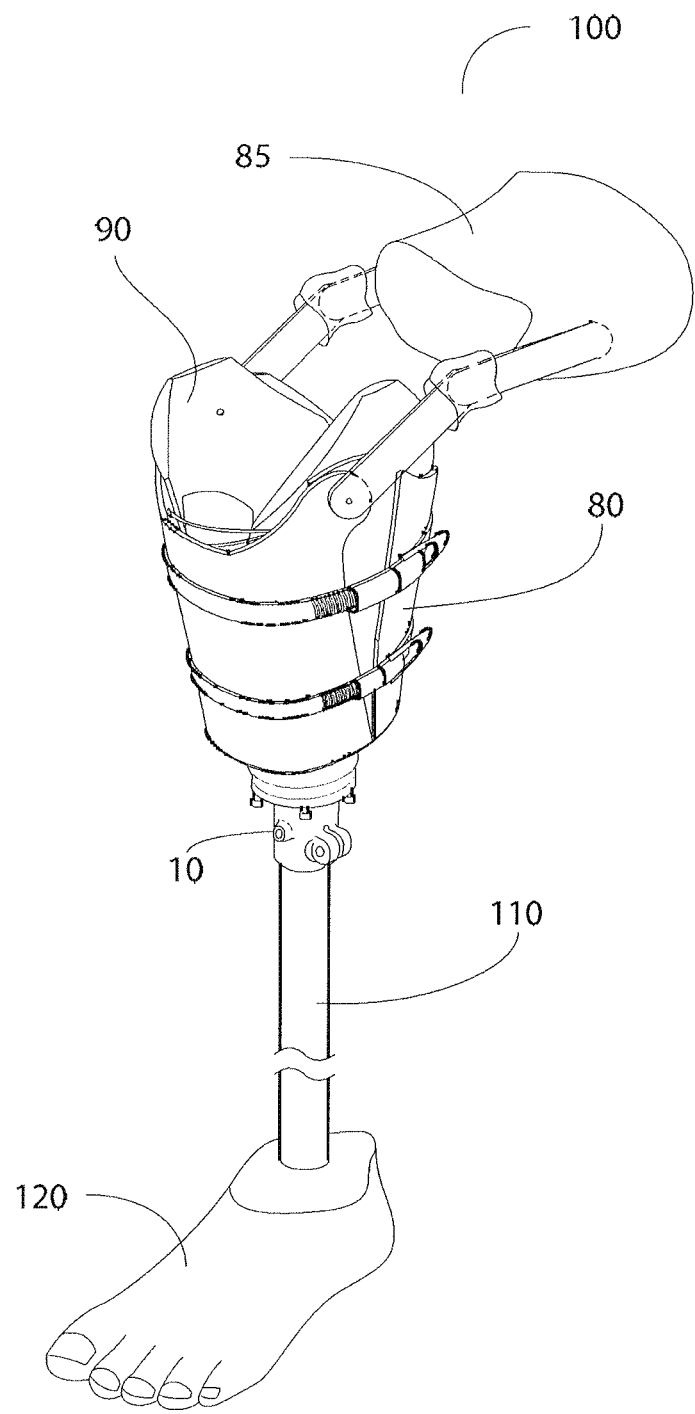
FIG. 11 illustrates a perspective view of an exemplary embodiment of an assembled modular prosthesis system.

FIG. 1 illustrates an exploded view of an exemplary embodiment of modular prosthesis system 100 comprised of connector 10, socket 80 with suspension system 85 (see FIGS. 9a and 9b), liner 90 (see FIG. 10), and shank 110 (see FIG. 11). In the embodiment shown, socket 80 and liner 90 include tightening components 84a, 84b and 95. Also visible in the embodiment shown is optional padding insert 88 which is placed at the bottom of socket 80 to support liner 90.

Figure 2:
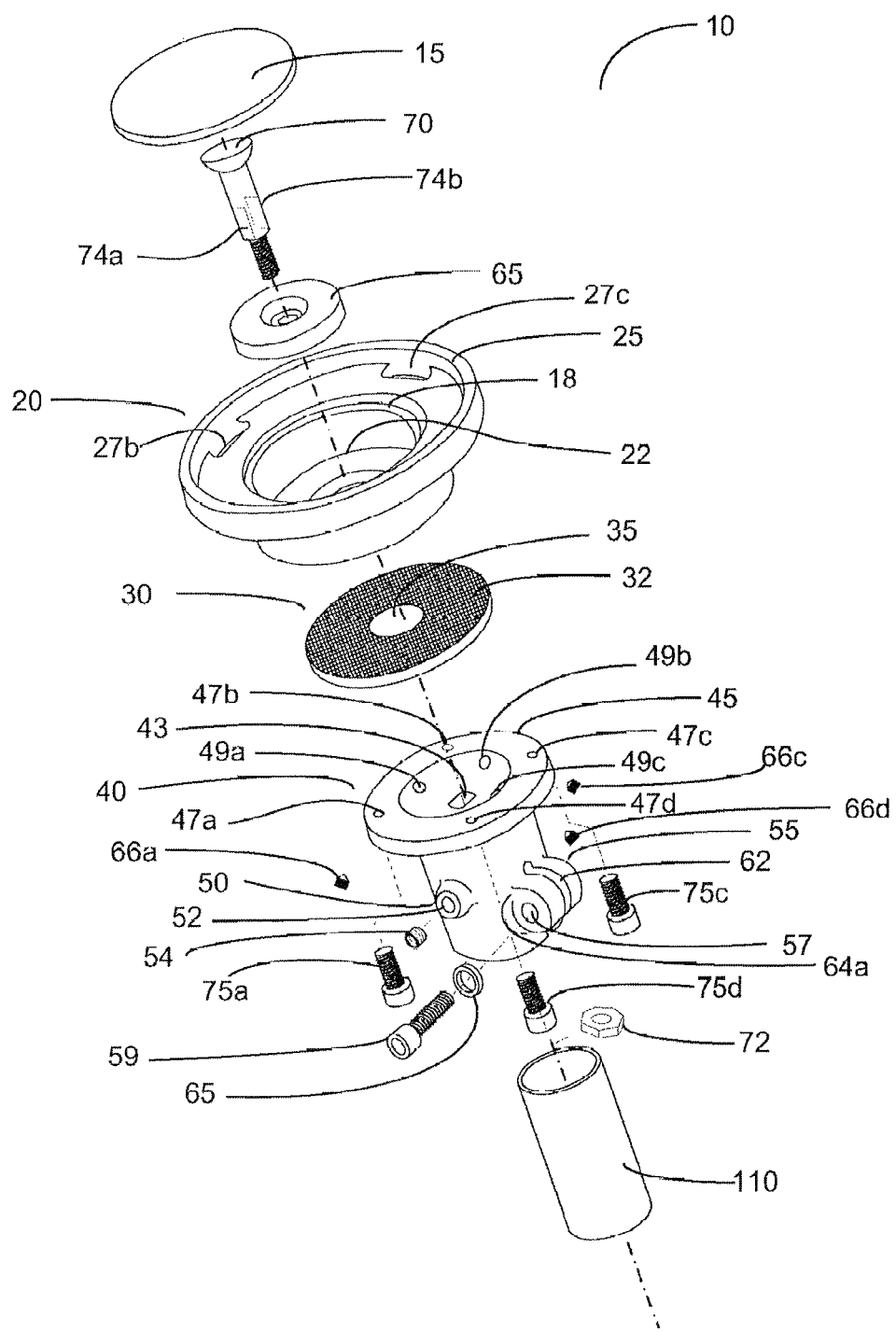
FIG. 2 illustrates an exploded view of an exemplary embodiment of a connector component for a modular prosthesis system.

FIG. 2 illustrates an exploded view of an exemplary embodiment of connector 10 for modular prosthesis system 100. In the embodiment shown, connector 10 is comprised of upper assembly 20, central plate 30, and lower assembly 40.

In the embodiment shown, upper assembly 20 is a tubular component with socket flange 25. Socket flange 25 is cup-shaped with a flat top surface. At the interface of socket flange 25 and the lower tubular portion of upper assembly 20 is ridge 18 for receiving and supporting cover 15. Socket flange 25 further includes apertures 27a, 27b, 27c, 27d (27a, 27d not visible) for inserting securing components 29a, 29b, 29c, 29d (not visible) used to secure connector 10 to socket 80. In the embodiment shown, apertures 27a, 27b, 27c, 27d are oval-shaped and are located near the edge of socket flange 25. In various other embodiments, apertures 27a, 27b, 27c, 27d are eliminated and socket 80 is secured to connector 10 in an alternate way. For example, one or more bolts or other fasteners may be threaded through apertures positioned on a substantially horizontal surface of upper assembly 20 and corresponding apertures on socket 80 (see FIG. 12).

In the embodiment shown, centered in the bottom of upper assembly 20 is aperture 22 for tapered shoulder screw 70. Aperture 22 is round and has a diameter that is substantially larger than the diameter of tapered shoulder screw 70 in this illustrated embodiment.

Central plate 30 is located between upper assembly 20 and lower assembly 40. The top surface of central plate 30 has raised grid pattern 32. In the embodiment shown, raised grid pattern 32 is uniform and has a plurality of raised protuberances in the shape of isosceles trapezoids (but other shapes may be used, and the grid pattern may be non-uniform). The bottom surface of upper assembly 20 has recessed grid pattern 28 (see FIGS. 3 and 4) that corresponds to raised grid pattern 32 on the top surface of central plate 30. Corresponding grid patterns 28, 32 on the bottom surface of upper assembly 20 and the top surface of central plate 30, respectively, allow for forward and backward adjustment and side-to-side adjustment.

In the embodiment shown, the bottom surface of central plate 30 has a rounded protuberance 37 (see FIG. 6) which corresponds to the shape of the upper surface of lower assembly 40. Central plate 30 further includes aperture 35 for tapered shoulder screw 70. In the embodiment shown, aperture 35 is round and has a diameter that is substantially larger than the diameter of the shank of tapered shoulder screw 70, but smaller than the diameter of aperture 22 in upper assembly 20.

In the embodiment shown, lower assembly 40 is a tubular component with central plate flange 45. The outer edge of the top surface of central plate flange 45 is flat, while the center portion of the top surface of central plate flange 45 is concave to accommodate rounded protuberance 37 of central plate 30.

The flattened portion of the top surface of central plate flange 45 includes a plurality of apertures 47a, 47b, 47c, 47d for central plate supporting components 75a, 75b, 75c, 75d (75b not visible). In the center of central plate flange 45 is aperture 43 for tapered shoulder screw 70. In the embodiment shown, aperture 43 is oval-shaped to accommodate and secure tapered shoulder screw 70.

In the embodiment shown, the outer edge of the concave portion on the top surface of central plate flange 45 further includes a plurality of apertures 49a, 49b, 49c, 49d (49d not visible) for insertion of set screws 66a, 66b, 66c, 66d (66b not visible). Apertures 49a, 49b, 49c, 49d pass completely through central plate flange 45 and set screws 66a, 66b, 66c, 66d help to firmly anchor connector 10 once the final position has been attained. In the embodiment shown, set screws 66a, 66b, 66c, 66d are cone point set screws; however, in other embodiments another type of set screw known in the art (e.g., domed point, cup point, dog point) may be used.

In the embodiment shown, upper assembly 20 further includes depressions 51a, 51b, 51c, 51d (see FIGS. 3 and 4) located on the top of the tubular portion of lower assembly 40 just under apertures 49a, 49b, 49c, 49d. Depressions 51a, 51b, 51c, 51d provide a space which allows a tool (e.g., a Hex driver) to be used to insert set screws 66a, 66b, 66c, 66d.

In addition, one side of tubular portion of lower assembly 40 further includes raised surface 50 which has aperture 52 for insertion of set screw 54. Aperture 52 passes completely through the side of lower assembly 40 and when set screw 54 is inserted, the end of set screw 54 crosses the plane of the inner surface of lower assembly 40 and bumps against shank 110. In the embodiment shown, the top of raised surface 50 is flat; however, in other embodiments, the top of raised surface 50 may have slight curvature, mimicking the contours of lower assembly 40. In the embodiment shown, set screw 54 is a cone point set screw.

In the embodiment shown, lower assembly 40 further includes protuberance 55 having apertures 57 for insertion of shank securing component 59. Protuberance 55 is rounded and extends perpendicularly outward from lower assembly 40. In the embodiment shown, lower assembly 40 further includes groove 62 which starts at the bottom of lower assembly 40 and extends to approximately the center of lower assembly 40, cutting protuberance 55 in half. In the embodiment shown, lower assembly 40 further includes depressions 64a, 64b (64b not visible) in lower assembly 40 on each side of protuberance 55. Depressions 64a, 64b provide a space which allows a tool (e.g., wrench, socket wrench) to be used to tighten shank securing component 59. Gap 62 allows flexibility for the clamp to squeeze around the shank 110.

In the embodiment shown, shank securing component 59 is comprised of a bolt and nut; the bolt is inserted through aperture 57 and the nut is threaded onto the end of the bolt and tightened, securing lower assembly 40 to shank 110 and preventing lower assembly 40 from rotating around shank 110.

In the embodiment shown, shank 110 has a diameter of 30 mm; however, in other embodiments, lower assembly 40 may be designed to accommodate shanks of varying diameters. In an exemplary embodiment, shank 110 will include a connector at the bottom which allows various types of feet known in the art, such as the SACH foot or the NIAGRA foot, to be connected to shank 110. In an exemplary embodiment, the length of shank 110 is adjustable, eliminating the need to cut shank 110 to a length sized for each amputee.

Tapered shoulder screw 70 is inserted through aperture 22 in upper assembly 20, aperture 35 in central plate 30, and aperture 43 in lower assembly 40. When tapered shoulder screw 70 is positioned, the threaded end of tapered shoulder screw 70 extends into lower assembly 40. Nut 72 is threaded onto the threaded end of tapered shoulder screw 70 and tightened, securing upper assembly 20, central plate 30, and lower assembly 40 together.

In the embodiment shown, nut 72 is a K-nut, that is, a nut with an attached, free-spinning washer. In the embodiment shown, the washer is an external star washer. The use of a K-nut provides maximum torsional resistance and prevents loosening caused by vibration.

In the embodiment shown, tapered shoulder screw 70 is inserted through washer 65 before tapered shoulder screw 70 is inserted through aperture 22 in upper assembly. Washer 65 has a larger diameter than aperture 22 covering aperture 22 and preventing tapered shoulder screw 70 from directly touching upper assembly 20. Washer 65 distributes the load of tapered shoulder screw 70.

In the embodiment shown, tapered shoulder screw 70 is a shoulder screw with a flat, tapered head and machined grooves 74a, 74b cut on opposite sides of tapered shoulder screw 70. Machined grooves 74a, 74b lock tapered shoulder screw 70 automatically into place inside oval-shaped aperture 43 in lower assembly 40, allowing tapered shoulder screw 70 to be tightened from one end.

In the embodiment shown, the bottom of washer 65 is flat while the top of washer 65 has a beveled outer edge. The edges of the aperture in the center of washer 65 are also beveled. The bevel angle is greater on the top of washer 65 to accommodate the tapered head of tapered shoulder screw 70. When washer 65 is used, only a small portion of the head of tapered shoulder screw 70 is visible above washer 65.

The large diameters (i.e., diameters substantially larger than the diameter of the shoulder of tapered shoulder screw 70) of aperture 22 in upper assembly 20 and aperture 35 in central plate 30, the oval shape of aperture 43 in lower assembly 40, rounded protuberance 37 of central plate 30 and corresponding concave center portion of top surface of lower assembly 40, and tapered shoulder screw 70 allow for angular adjustment of upper assembly 20 and central plate 30 in relationship to lower assembly 40. The ability to angularly adjust connector 10 allows connector 10 to accommodate various stump configurations, providing additional comfort to the amputee.

Once upper assembly 20, central plate 30, and lower assembly 40 are correctly positioned, nut 72 is tightened on tapered shoulder screw 70 and central plate supporting components 75a, 75b, 75c, 75d are inserted into apertures 47a, 47b, 47c, 47d from the bottom and are tightened until the ends of central plate supporting components 75a, 75b, 75c, 75d press against the bottom of central plate 30, supporting central plate 30 and upper assembly 20 and further securing upper assembly 20, central plate 30, and lower assembly 40 together.

Cover 15 is placed on upper assembly 20 so that it rests on ridge 18 of upper assembly 20, covering tapered shoulder screw 70 and washer 65. When cover 15 is positioned, the surface of cover 15 is flush with the inside surface of socket flange 25.

In the embodiment shown, cover 15 and ridge 18 are shown for ease of illustration. In various other embodiments, ridge 18 and cover 15 are omitted and the inner surface of socket flange 25 is a single piece.

In the embodiment shown, upper assembly 20, central plate 30, lower assembly 40, and cover 15 are comprised of polyphthalamide (i.e., PPA or high performance polyamide); however, in various other embodiments those components may be comprised of other thermoplastics/synthetic resins, such as nylon, acrylonitrile butadiene styrene (ABS), polypropylene, polyamide-imide, polybenzimidazole (PBI), polybutylene (PB-1) or combinations thereof, or any other suitable non-metal material.

Figure 3:
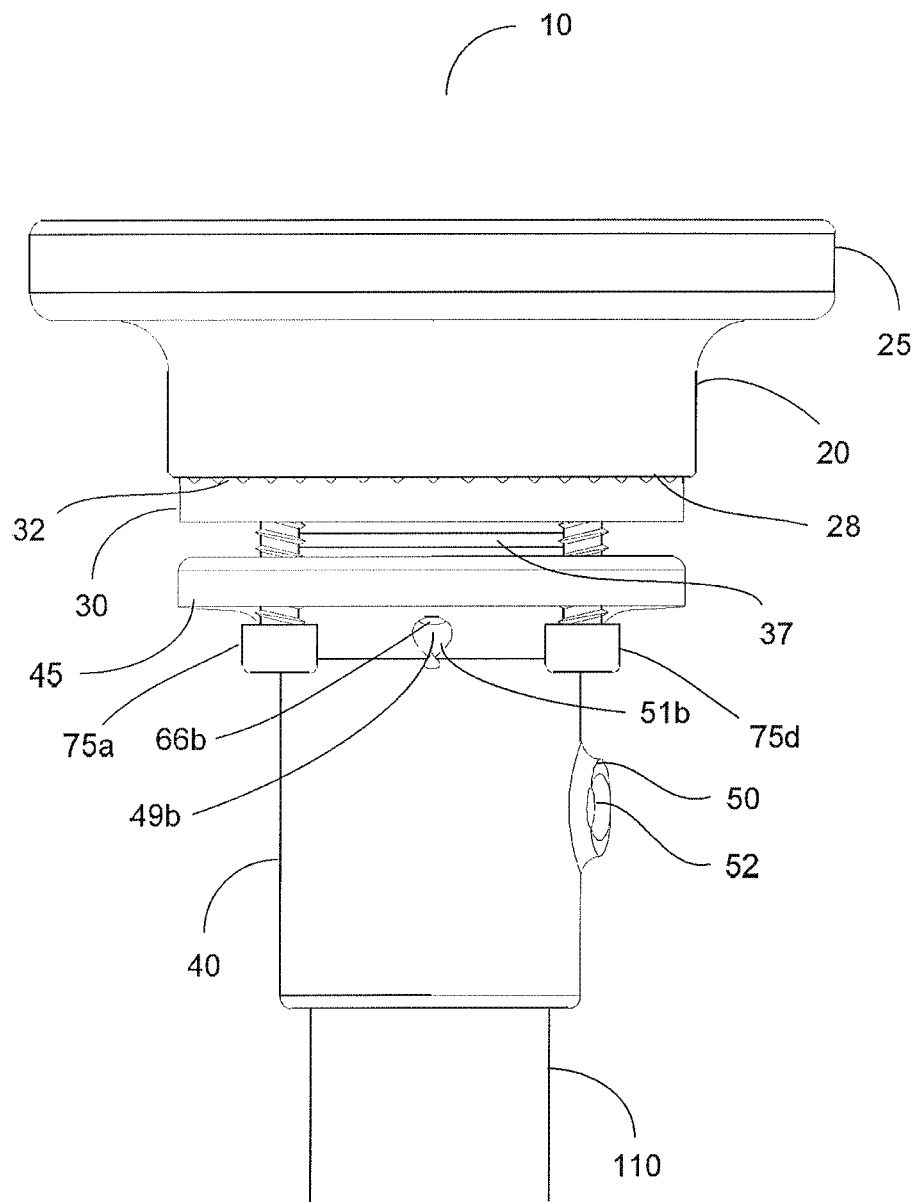
FIG. 3 illustrates a front view of an exemplary embodiment of a connector for a modular prosthesis system.

FIG. 3 illustrates a front view of an exemplary embodiment of connector 10 for modular prosthesis system 100. Visible in FIG. 3 are upper assembly 20, including socket flange 25 and recessed grid pattern 28; central plate 30, including raised grid pattern 32 and rounded protuberance 37; lower assembly 40, including central plate flange 45, aperture 49b, depression 51b, raised surface 50, and aperture 52; set screw 66b; central plate supporting components 75a, 75d; and shank 110.

Figure 4:
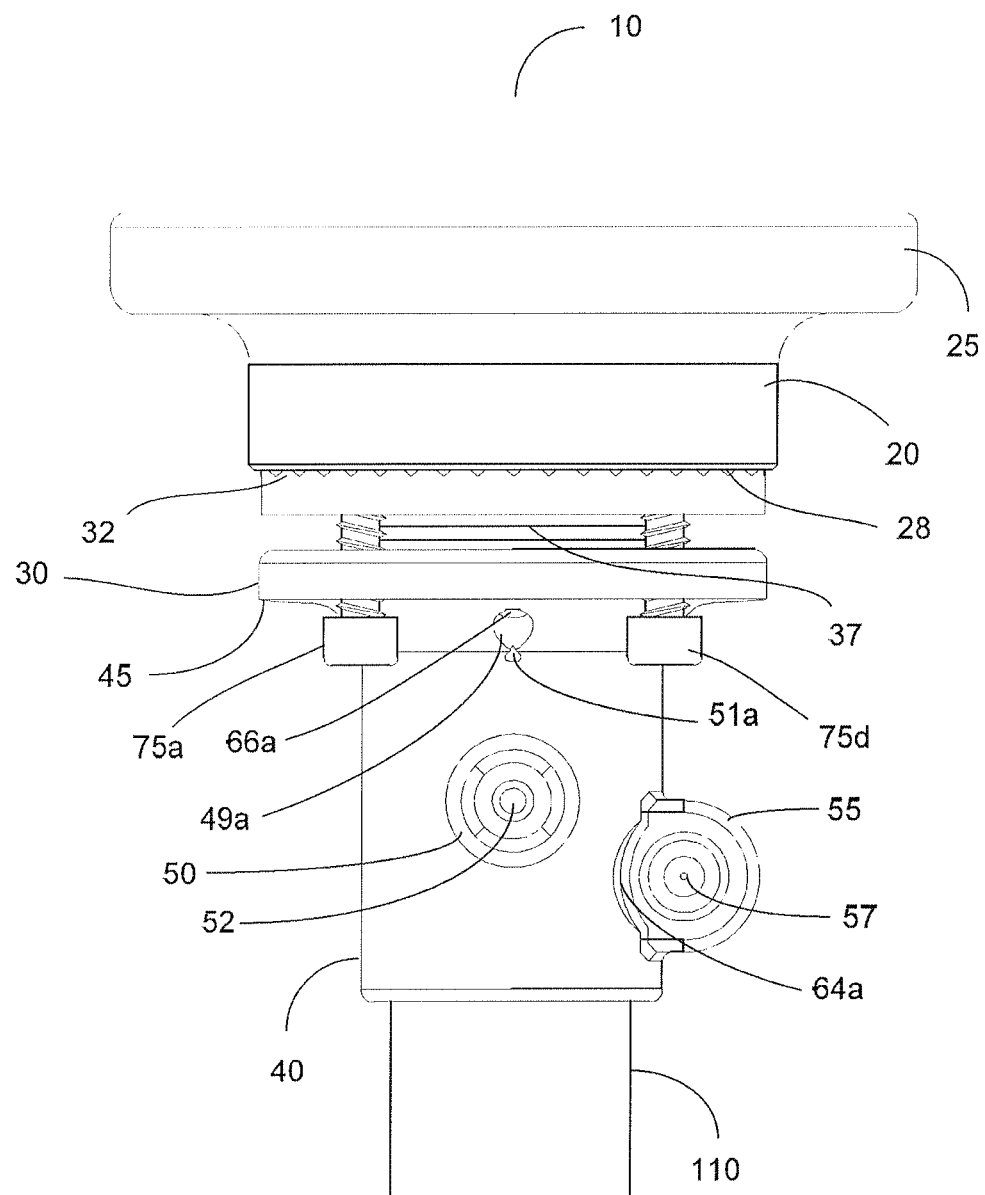
FIG. 4 illustrates a side view of an exemplary embodiment of a connector for a modular prosthesis system.

FIG. 4 illustrates a side view of an exemplary embodiment of connector 10 for modular prosthesis system 100. Visible in FIG. 4 are upper assembly 20, including socket flange 25 and recessed grid pattern 28; central plate 30, including raised grid pattern 32 and rounded protuberance 37; lower assembly 40, including central plate flange 45, aperture 49a, depression 51a, raised surface 50, aperture 52, protuberance 55, aperture 57, and depression 64a; set screw 66a; central plate supporting components 75a, 75d; and shank 110.

Figure 5:
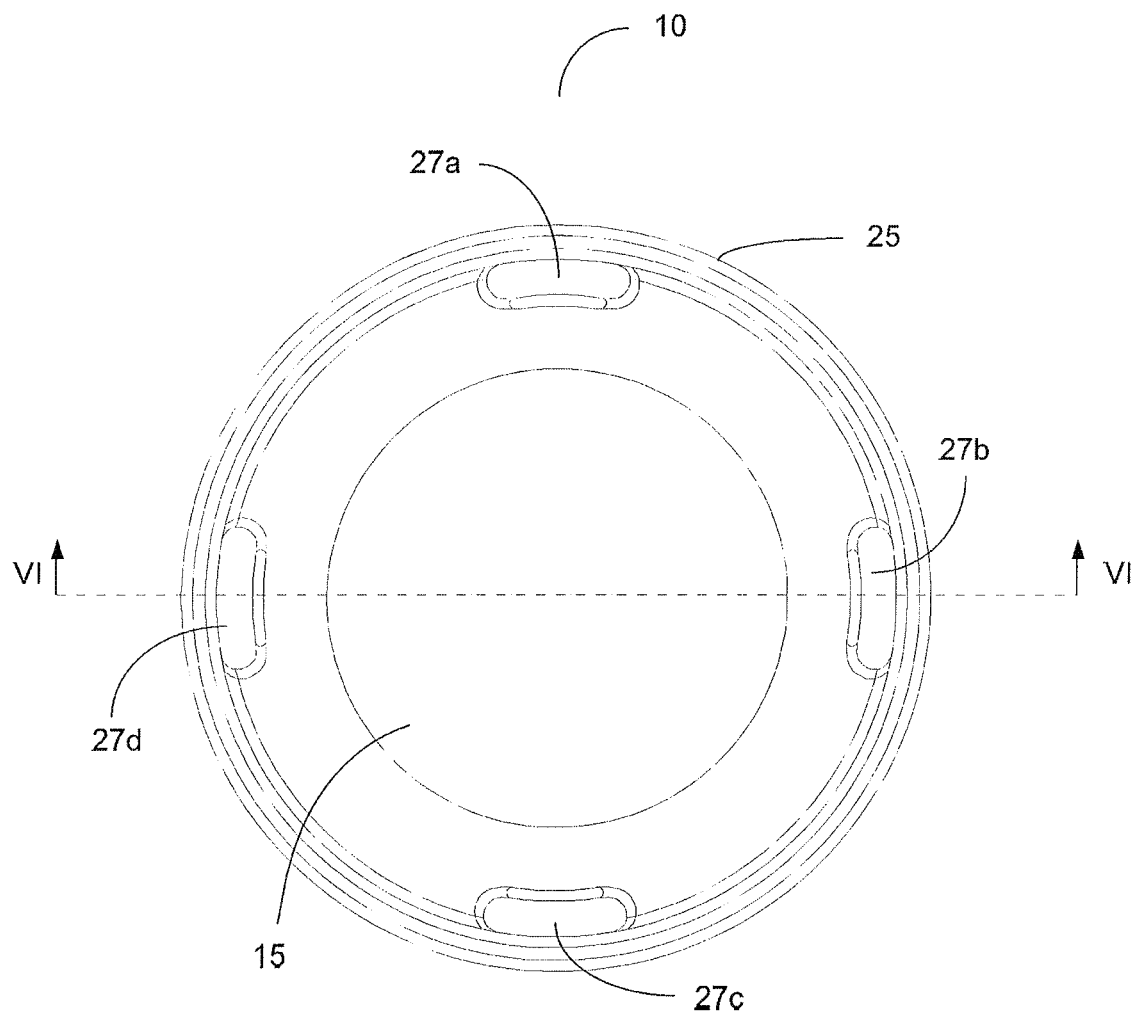
FIG. 5 illustrates a top view of an exemplary embodiment of a connector for a modular prosthesis system.

FIG. 5 illustrates a top view of an exemplary embodiment of connector 10 for modular prosthesis system 100. Visible in FIG. 5 are socket flange 25 of upper assembly 20, cover 15, and apertures 27a, 27b, 27c, 27d for securing components 29a, 29b, 29c, 29d (not visible), which are used to secure connector 10 to socket 80 (not visible).

Figure 6:
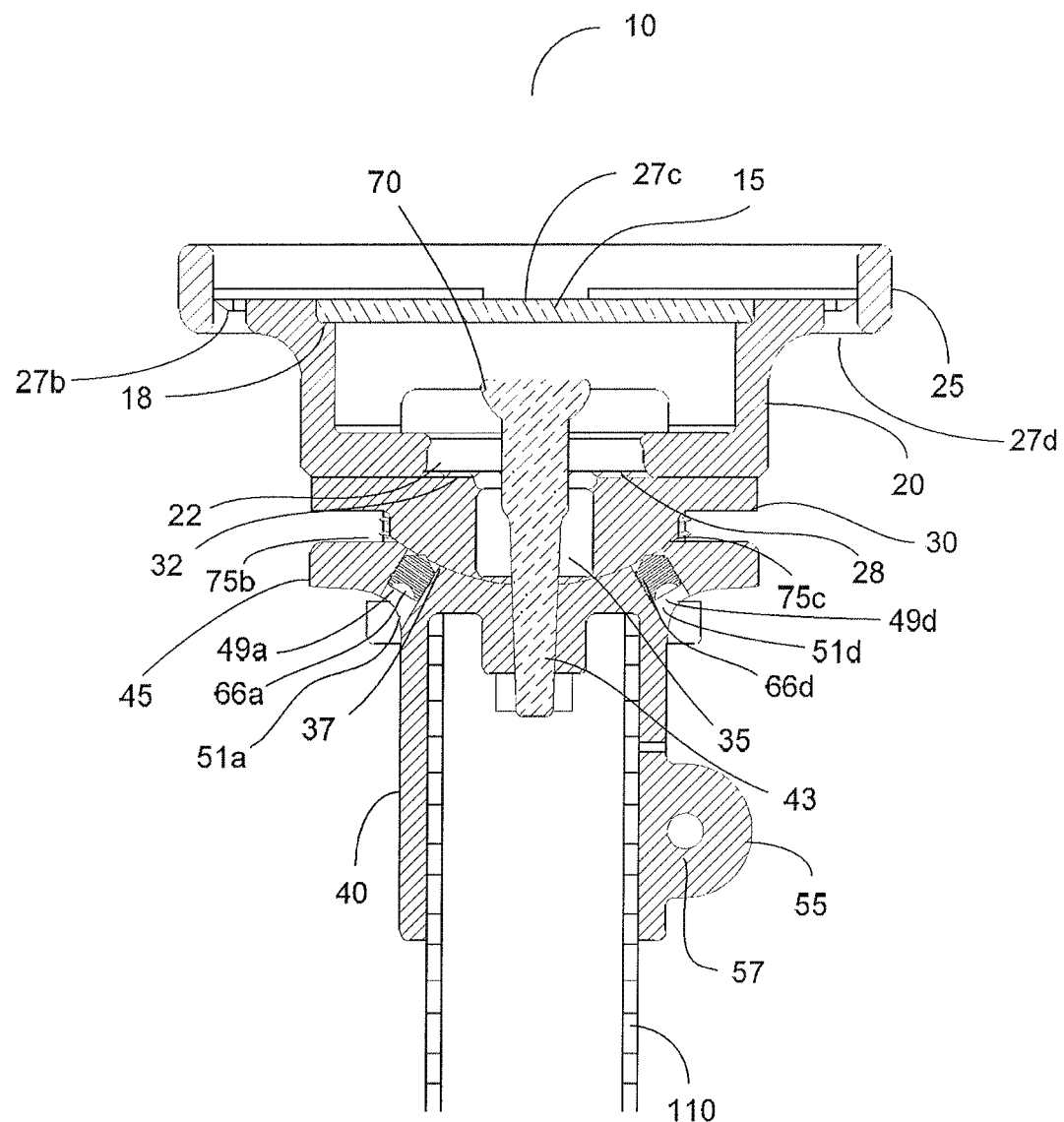
FIG. 6 illustrates a sectional view of an exemplary embodiment of a connector for a modular prosthesis system.

FIG. 6 illustrates a sectional view of an exemplary embodiment of connector 10 for modular prosthesis system 100 taken along line VI of FIG. 5. Visible in FIG. 6 are cover 15; upper assembly 20, including aperture 22, socket flange 25, recessed grid pattern 28, apertures 27b, 27c, 27d, and ridge 18; central plate 30, including aperture 35, raised grid pattern 32, and rounded protuberance 37; lower assembly 40, including aperture 43, central plate flange 45, aperture 49a, 49d, depression 51a, 51d, aperture 57, and protuberance 55; set screws 66a, 66d; central plate supporting components 75b, 75c; tapered shoulder screw 70, and shank 110.

Figure 7A:
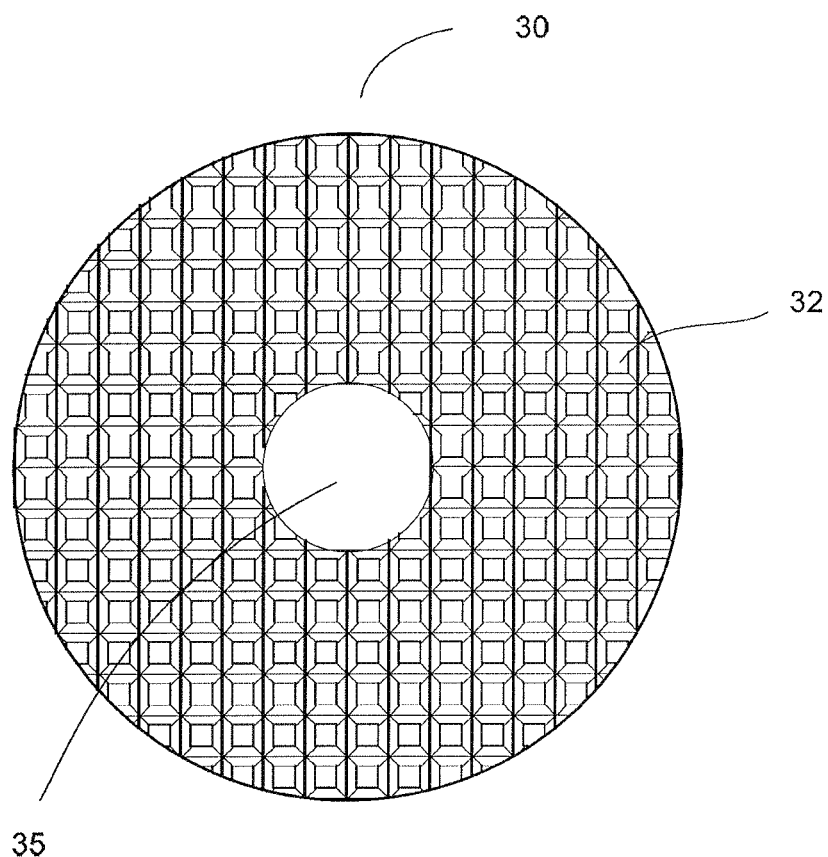
FIG. 7a illustrates a top view of an exemplary embodiment of a central plate of a connector.

FIG. 7a illustrates a top view of an exemplary embodiment of central plate 30 showing raised grid pattern 32 and aperture 35.

Figure 7B:
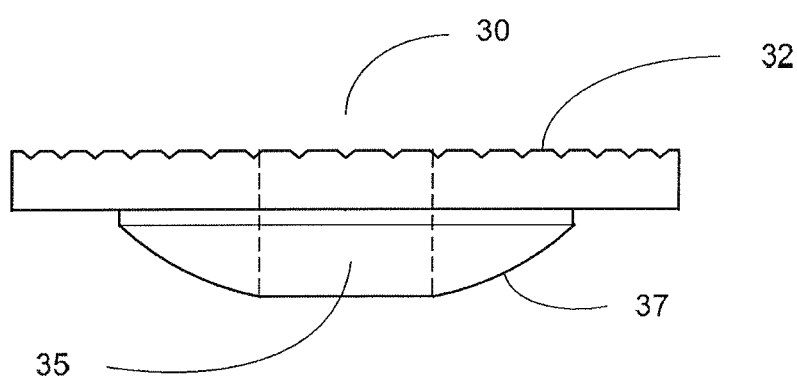
FIG. 7b illustrates a side view of an exemplary embodiment of a central plate of a connector.

FIG. 7b illustrates a side view of an exemplary embodiment of central plate 30 showing raised grid pattern 32, aperture 35, and rounded protuberance 37.

Figure 8A:
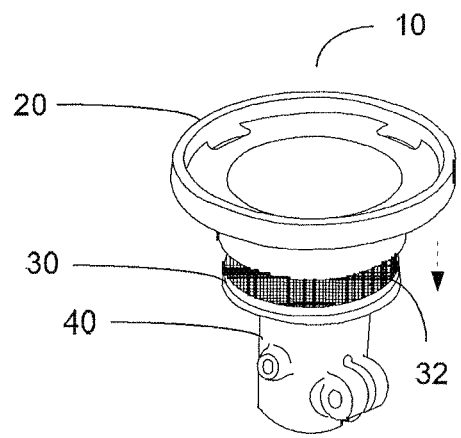
FIGS. 8a, 8b, and 8c illustrate front-back, side-to-side, and angular adjustment of an exemplary embodiment of a connector.
Figure 8B:
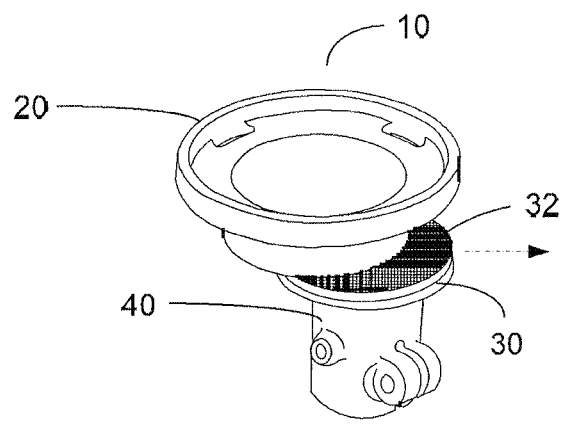
Figure 8C:
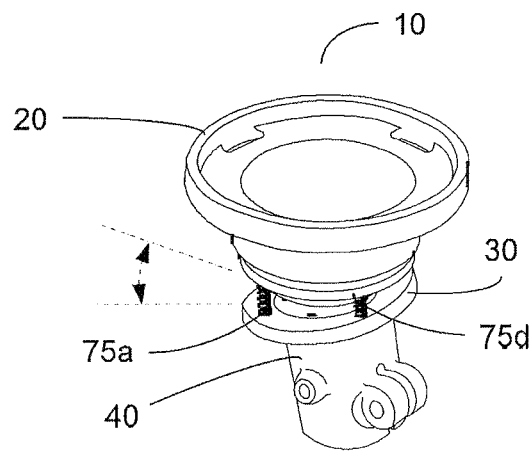

FIGS. 8a, 8b, and 8c illustrate front-back, side-to-side, and angular adjustment of an exemplary embodiment of connector 10, which allow the angle and position of prosthetic foot 115 (FIG. 11) to be changed (e.g., to compensate for foot inset-outset). In FIG. 8a, upper assembly 20 has been shifted backward (i.e., along x-axis) in relation to central plate 30 and lower assembly 40. In FIG. 8b, upper assembly 20 has been shifted sideways (i.e., along y-axis) in relation to central plate 30 and lower assembly 40.

When upper assembly 20 is shifted forward-backward or sideways (i.e., along x- or y-axis) in relation to central plate 30 and lower assembly 40, a portion of recessed grid pattern 28 (not visible) on the lower surface of upper assembly 20 and portion of raised grid pattern 32 on the upper surface of central plate 30 are exposed. The size of aperture 22 in upper assembly 20 and aperture 35 in central plate 30 permit tapered shoulder screw 70 (not visible) to be angled when upper assembly 20 is shifted forward-backward and/or sideways in relation to central plate 30 and lower assembly 40, ensuring that upper assembly 20, central plate 30, and lower assembly 40 are secure.

In FIG. 8c, upper assembly 20 and central plate 30 are tilted in relation to lower assembly 40 so that central plate 30 and central plate flange 45 on lower assembly 40 are no longer parallel. The concave center portion of the top surface of lower assembly 40 allows rounded protuberance 37 on the bottom of central plate 30 to tilt, allowing for angular adjustment of upper assembly 20 and central plate 30. When upper assembly 20 and central plate 30 are positioned at the desired angle, central plate supporting components 75a, 75b, 75c, 75d are tightened, securing lower assembly 40 to upper assembly 20 and central plate 30.

In the embodiment shown, connector 10 is capable of being adjusted in one or more directions concurrently, allowing for maximum adjustment of connector 10 to specifically accommodate each amputee's residual limb and gait. For example, connector 10 may be adjusted front-back, side-to-side, and angled. In other embodiments, connector 10 may be capable of only one type of adjustment (e.g., angular).

Figure 9A:
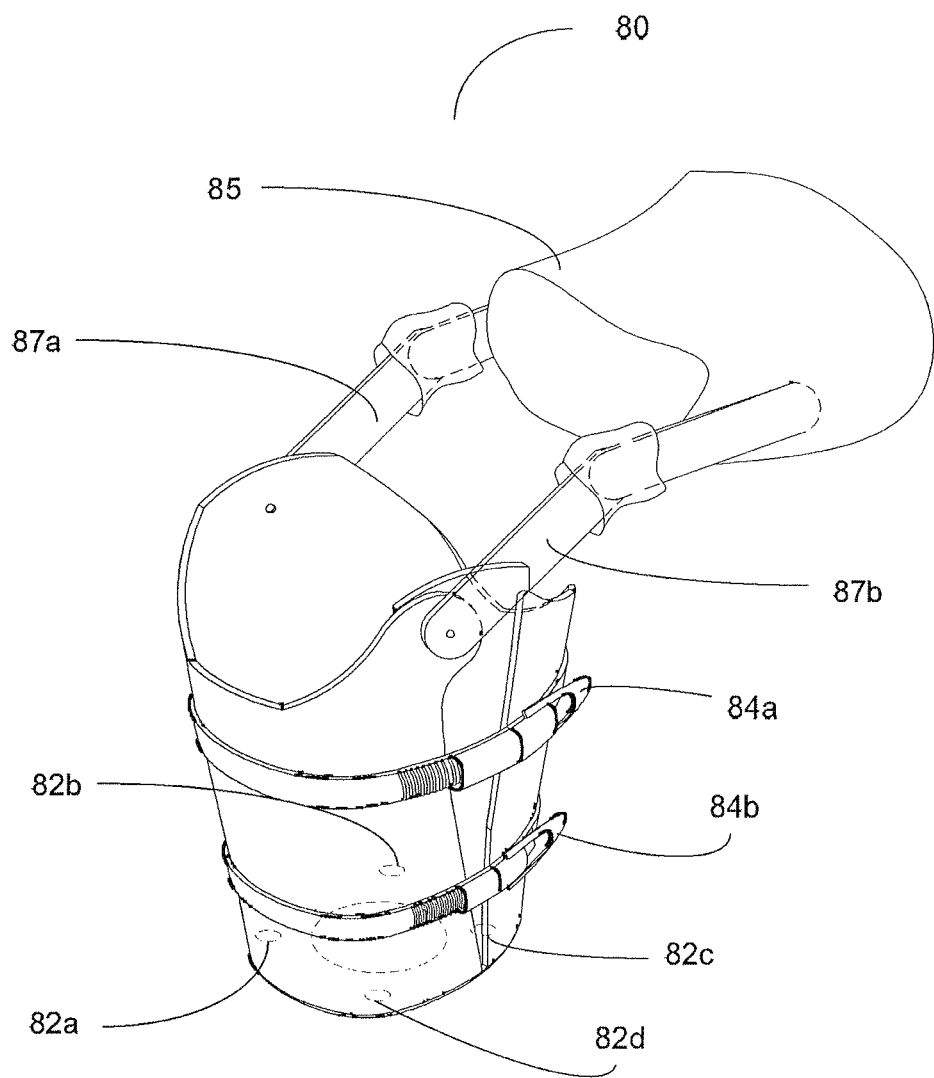
FIGS. 9a and 9b illustrate perspective views of exemplary embodiments of a socket for a modular prosthesis system.
Figure 9B:
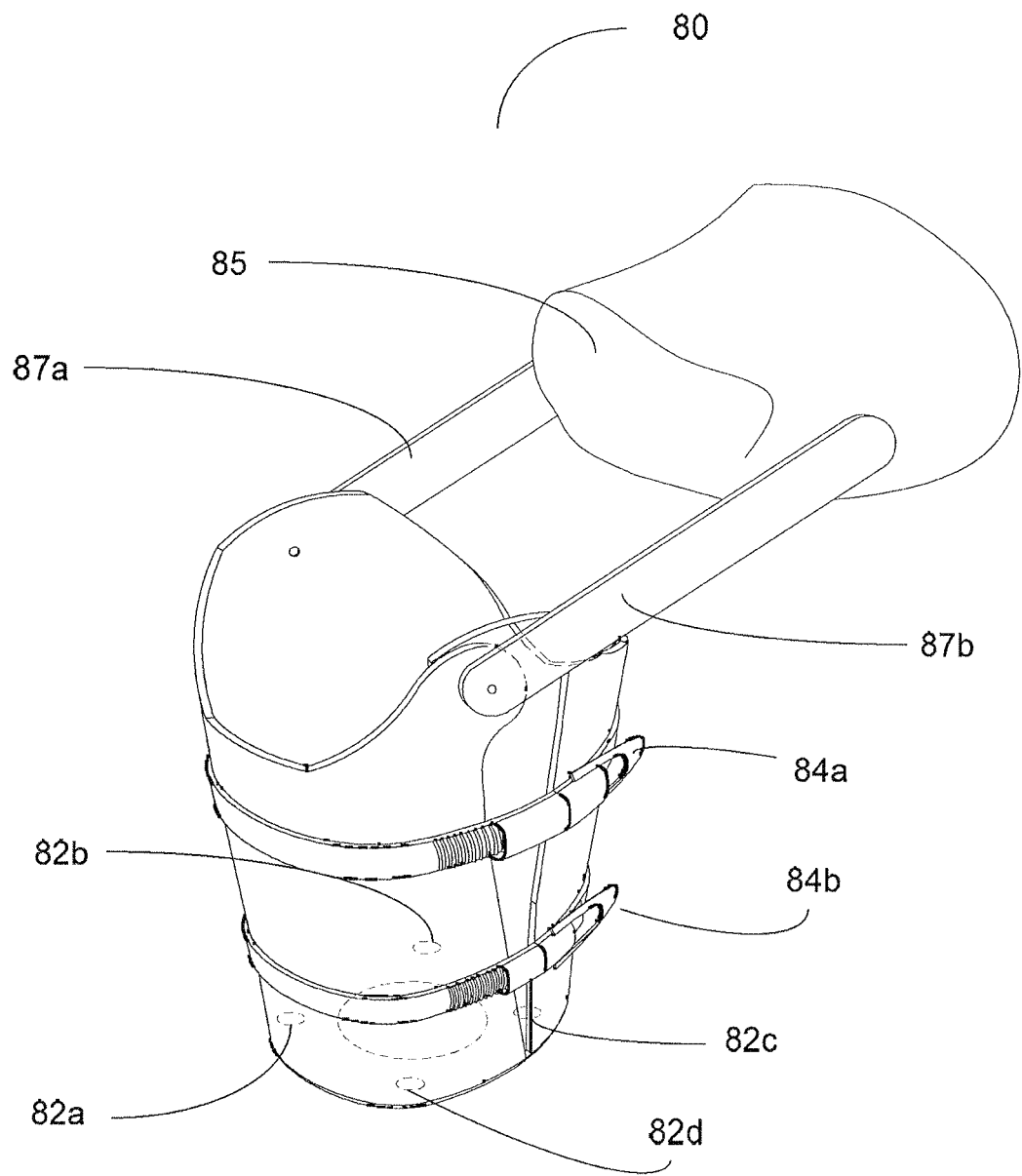

FIGS. 9a and 9b illustrate perspective views of exemplary embodiments of socket 80 for modular prosthesis system 100. Socket 80 includes tightening components 84a, 84b, which allow the tension in socket 80 to be adjusted by each amputee. In the embodiment shown, socket tightening components 84a, 84b are buckle assemblies.

In the embodiment shown, socket 80 further includes suspension system 85 with optional pivotal side joints 87a, 87b. Suspension system 85 secures the prosthesis on the amputee's residual limb. The inclusion of pivotal side joints 87a, 87b allows the amputee to move his or her knee more freely with less hindrance from the prosthesis. In various other embodiments, suspension system 85 may vary. For example, suspension system 85 may be comprised of a roll-on neoprene sleeve with an adjustable strap that goes around the amputee's thigh and one or more length-adjustable straps that connect the sleeve to socket 80.

In FIG. 9a, optional pivotal side joints 87a, 87b are comprised of two pieces connected at a joint. In various embodiments, the joint may be located further from or closer to suspension system 85. In FIG. 9b, optional pivotal side joints 87a, 87b are comprised of a single straight piece. In various embodiments, there may be fewer or more joints, the pieces may be of varying length, and/or curved or irregularly-shaped.

In various other embodiments, there may be more socket tightening components 84a, 84b and/or the type of tightening components may vary. For example, socket 80 may include laces or one or more straps secured by hook-and-loop fastener or another means, as well as combinations of such tightening components.

Also visible are apertures 82a, 82b, 82c, 82d for inserting securing components 29a, 29b, 29c, 29d (not visible) for securing connector 10 to socket 80.

FIG. 10 illustrates a perspective view of an exemplary embodiment of liner 90 for modular prosthesis system 100. Liner 90 is shaped to fit inside socket 80. In the embodiment shown, liner 90 further includes liner extension component 96 which allows the height of the liner to be adjusted to the length of each amputee's residual limb. In the embodiment shown, liner extension component 96 is a plurality of accordion fabric folds at the bottom portion of liner 90. In various other embodiments, liner extension component 96 may be comprised of adjustable or removable panels or another component that allows the length of liner 90 to be adjusted.

In the embodiment shown, liner 90 has tightening component 95 which allows the tension of liner 90 to be adjusted as the residual limb changes, accommodating long-term or daily changes of the residual limb, as well as allowing the individual amputee to adjust liner 90 to his or her comfort. For example, liner tightening component 95 allows liner 90 to be loosened as a result of swelling of the residual limb. In the embodiment shown, liner tightening component 95 is laces. In various other embodiments, liner tightening component 95 may include one or more adjustable straps.

In the embodiment shown, liner 90 includes stress distribution panels 92a, 92b secured to the outer surface of the sides of liner 90 and stress distribution panels 92c, 92d (92d not visible) secured to the outer surface of the front and back of liner 90. Stress distribution panels 92a, 92b, 92c, 92d help to distribute pressure and shear stresses. In the embodiment shown, stress distribution panels 92a, 92b are comprised of plastic. In various embodiments, the shape of the stress distribution panels varies depending on the placement of the panel (i.e., the side panels have a shape different than that of front and back panels).

In an exemplary embodiment, liner 90 further includes one or more optional removable padding inserts 98, which can be inserted into liner 90 for further adjustability, allowing liner 90 to accommodate the shape of each individual amputee's residual limb. For example, padding inserts may be inserted into the bottom of liner 90 to accommodate a bony prominence at the end of a residual limb or into the sides of liner 90 to add additional padding in areas that are less pressure tolerant.

Liner 90 is comprised of a soft, comfortable material, such as PE-LITE or silicone, that doesn't break down the skin of the amputee's residual limb. In various other embodiments, liner 90 may be comprised of a plastic mesh material or other material that allows for breathability for use in warmer climates or during physical activities. In various embodiments, liner 90 may be manufactured by gluing together layers of foam having different durometers.

FIG. 11 illustrates a perspective view of an exemplary embodiment of assembled modular prosthesis system 100. In an exemplary embodiment, modular prosthesis system 100 includes all items and components required for immediate fitting. Connector 10, shank 110, and foot 115 may be one fully adjustable system that readily connects to socket 80 and suspension system 85. Liner 90 is inserted into socket 80. In an exemplary embodiment, modular prosthesis system 100 may include a telescoping shank.

Figure 12:
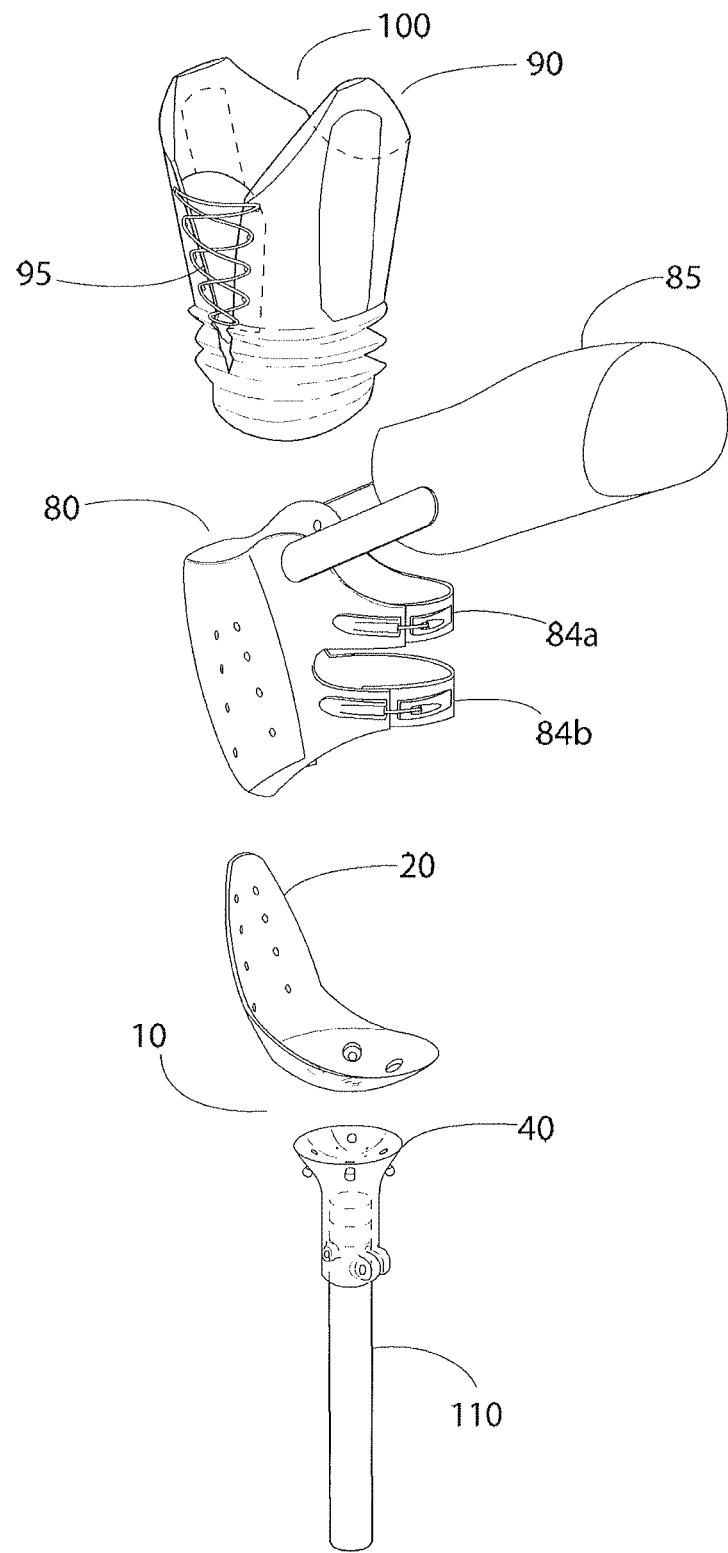
FIG. 12 illustrates an exploded view of another embodiment of a modular prosthesis system.

FIG. 12 illustrates an exploded view of another embodiment of modular prosthesis system 100 comprised of socket 80, liner 90, and connector 10. In the embodiment shown, socket 80 and liner 90 include tightening components 84a, 84b, and 95, respectively, and socket 80 further includes suspension system 85.

In the embodiment shown, connector 10 is comprised of upper assembly 20 and lower assembly 40. Upper assembly 20 is cup-shaped with a rounded bottom and a single elongated side. Lower assembly 40 is tubular-shaped having a flange with a concave center portion and a bottom portion for accepting shank 110. In the embodiment shown, upper assembly 20 is secured to lower assembly 40 by inserting a connecting screw (e.g., a tapered shoulder screw) or another type of fastener into each of the apertures in the rounded bottom of upper assembly 20 and into the apertures in the concave center portion of lower assembly 40. The position of the connecting screws can be adjusted to adjust the tilt between upper assembly 20 and lower assembly 40, allowing the position of the prosthetic foot to be adjusted (e.g., to compensate for foot inset-outset).

In the embodiment shown, the apertures in the bottom of upper assembly 20 are recessed to allow for placement of a washer.

In the embodiment shown, the single elongated side of upper assembly 20 includes a plurality of apertures which correspond to the apertures on socket 80. Socket 80 is secured to upper assembly 20 of connector 10 by threading a screw through two apertures (single row) in socket 80 and upper assembly 20. The plurality of rows of apertures accommodates for height adjustment. For example, for a shorter socket, the amputee would thread screws through the top four apertures of socket 80 and the top four apertures of upper assembly 20 (or any four corresponding apertures). For a longer socket, the amputee would thread screws through the bottom four apertures of socket 80 and the top four apertures of upper assembly 20. For shorter lengths, additional screws could be threaded through corresponding apertures to secure socket 80 and upper assembly more tightly together.

Modular prosthesis system 100 is easily fit to an individual and can be fully constructed and aligned in a reasonable amount of time. No casting or fabrication is required, eliminating the need for specialized tools and centers.

Modular prosthesis system 100 is highly adjustable, making it ideal for growing children, eliminating the need for many prosthetic revisions to insure a comfortable and functional device. In addition, modular prosthesis system 100 can be fit without a prosthetist making it desirable for developing countries, war-torn countries, and for individuals who are without insurance and/or don't have access to a prosthesis. The use of advanced technology and materials allows modular prosthesis system 100 to be economically manufactured and distributed.

Figures 13A, 13B, 13C:
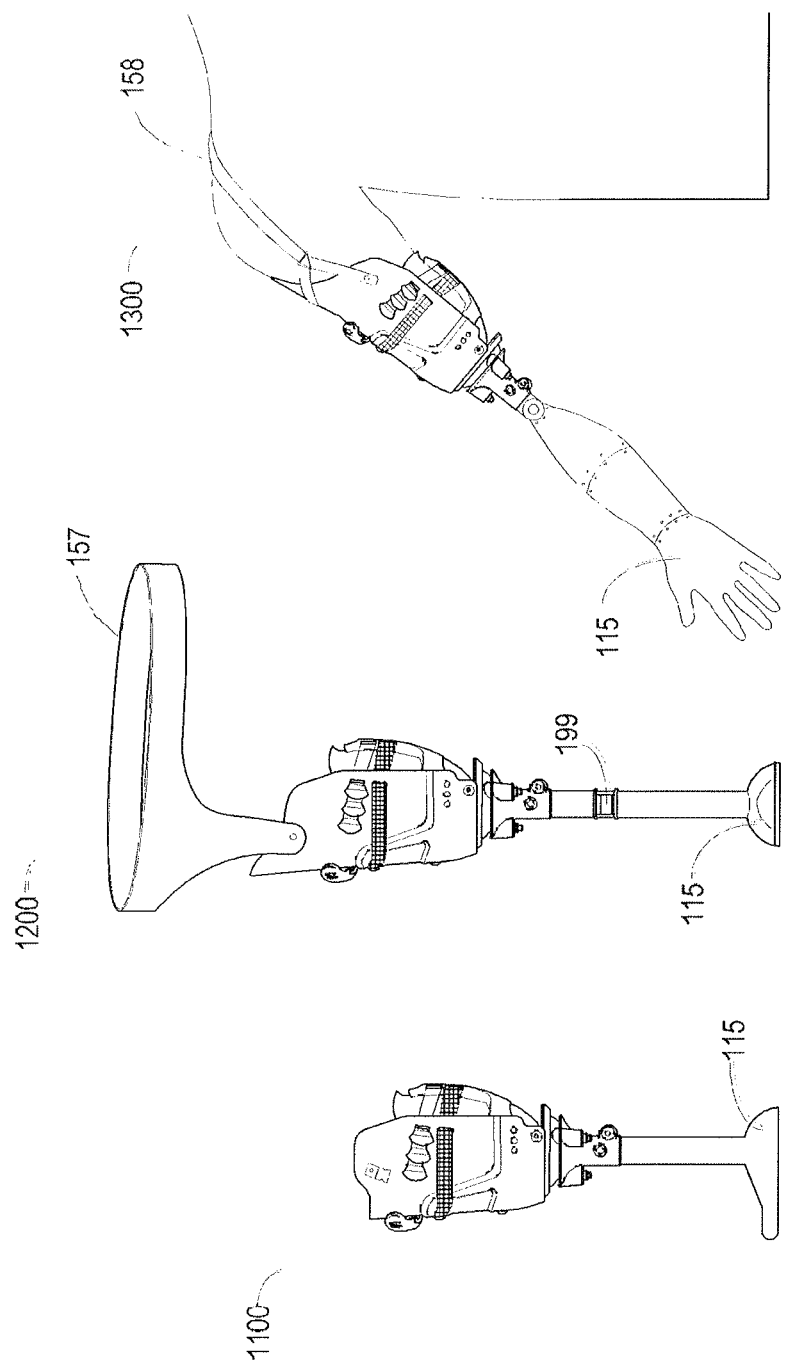
FIG. 13a illustrates an exemplary embodiment of a rapid fit modular prosthetic device for accommodating gait alignment and residual limb shape and volume for a below-the-knee residual limb.
FIG. 13b illustrates an exemplary embodiment of a rapid fit modular prosthetic device for accommodating gait alignment and residual limb shape and volume for an above-the-knee residual limb.
FIG. 13c illustrates an exemplary embodiment of a rapid fit modular prosthetic device for accommodating gait alignment and residual limb shape and volume for a residual limb which is an arm.

FIGS. 13a, 13b and 13c illustrate three different uses of a rapid fit modular prosthetic device for accommodating gait alignment and residual limb shape and volume. As illustrated in FIG. 13a, rapid fit modular prosthetic device for accommodating gait alignment and residual limb shape and volume 1100 is adapted for use on a below-the-knee residual limb. As illustrated in FIG. 13b, rapid fit modular prosthetic device for accommodating gait alignment and residual limb shape and volume 1200 may also be adapted for use with an above-the-knee residual limb. FIG. 13c illustrates rapid fit modular prosthetic device for accommodating gait alignment and residual limb shape and volume 1300 adapted for use with a residual limb which is an arm.

As illustrated in FIGS. 13a, 13b and 13c, the basic structure of rapid fit modular prosthetic device for accommodating gait alignment and residual limb shape and volume 1100, 1200, 1300 is the same. Rapid fit modular prosthetic device for accommodating gait alignment and residual limb shape and volume 1100 has prosthetic device 115 attached directly to rapid fit modular prosthetic device for accommodating gait alignment and residual limb shape and volume 1100. By comparison, rapid fit modular prosthetic device for accommodating gait alignment and residual limb shape and volume 1200 has knee 199 after prosthetic device 115 and an additional securing strap 157 to help stabilize rapid fit modular prosthetic device for accommodating gait alignment and residual limb shape and volume 1200. The orientation of prosthetic device 115 is also rotated at 90 degrees compared to rapid fit modular prosthetic device for accommodating gait alignment and residual limb shape and volume 1100.

When used for a below-the-knee residual limb, rapid fit modular prosthetic device for accommodating gait alignment and residual limb shape and volume 1100 is oriented so that it opens from the back of a wearer (i.e., at the calf). Because of the way pressure is exerted on rapid fit modular prosthetic device for accommodating gait alignment and residual limb shape and volume 1200 when used with an above-the-knee residual limb, and the movement caused by bending at the knee, rapid fit modular prosthetic device for accommodating gait alignment and residual limb shape and volume 1200 must be oriented to open from the side.

Similarly, as illustrated in FIG. 13c, rapid fit modular prosthetic device for accommodating gait alignment and residual limb shape and volume 1300 contains a different strap 158 to secure rapid fit modular prosthetic device for accommodating gait alignment and residual limb shape and volume 1300 to a residual limb which is an arm, and prosthetic device 115 is an arm instead of a foot or leg.

Figure 14:
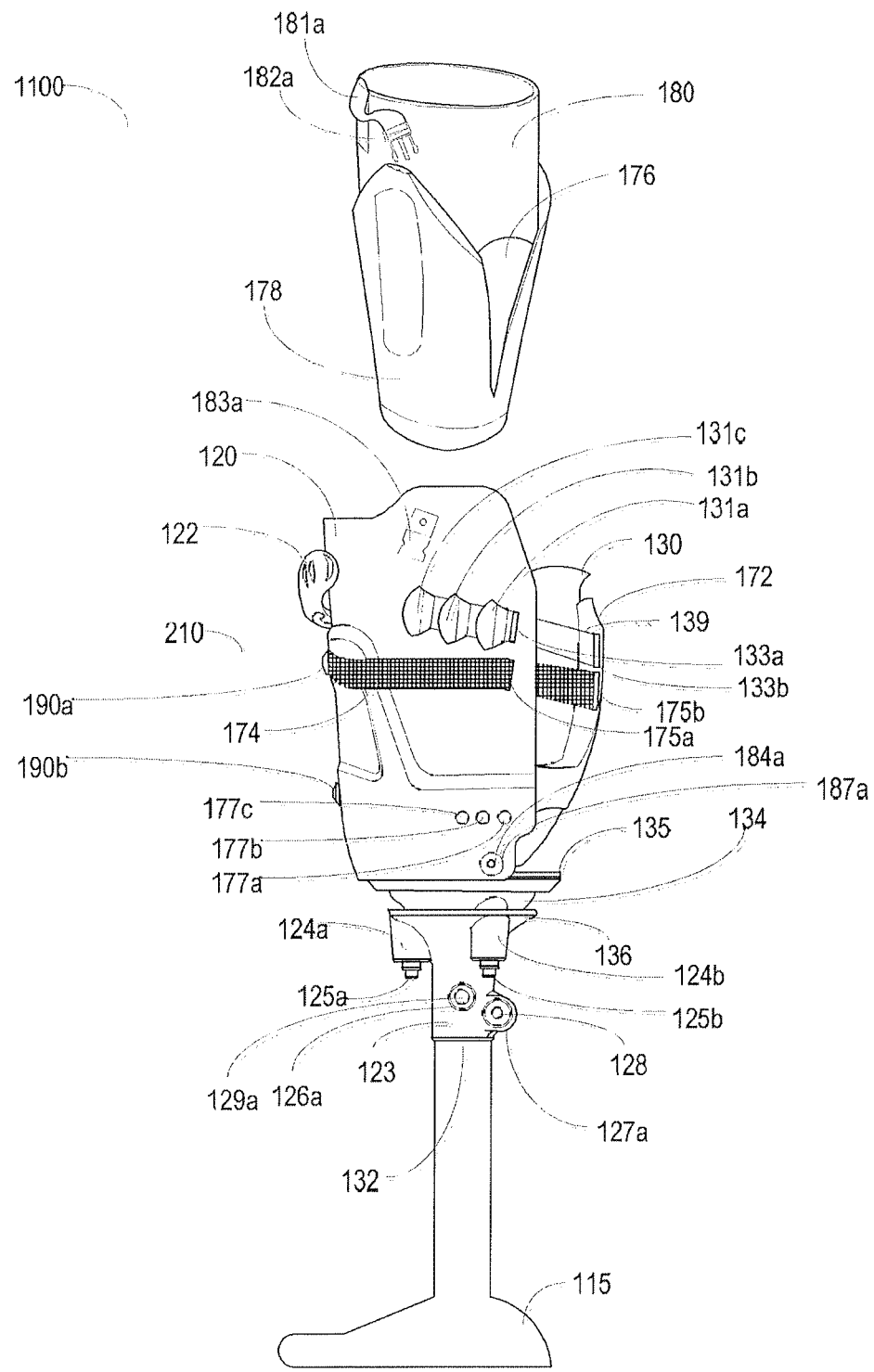
FIG. 14 illustrates an exemplary below-the-knee rapid fit modular prosthetic device for accommodating gait alignment and residual limb shape and volume.

FIG. 14 illustrates an exemplary embodiment of below-the-knee rapid fit modular prosthetic device for accommodating gait alignment and residual limb shape and volume 1100. Below-the-knee rapid fit modular prosthetic device for accommodating gait alignment and residual limb shape and volume 1100 contains rigid socket assembly 210, which is comprised of non-pivotal front limb engaging panel 120, pivotal rear limb engaging panel 130, rigid outer support rib 172, and deformable inner liner 178 with silicone liner 180. In the exemplary embodiment shown, rigid socket assembly 210 creates a tubular recess which receives a residual limb.

As illustrated in FIG. 14, pivotal rear limb engaging panel 130 overlaps non-pivotal front limb engaging panel 120 on the inside of non-pivotal front limb engaging panel 120. Rigid outer support rib 172 has an inverted T-shape and supports pivotal rear limb engaging panel 130 in front limb engaging panel 120.

In the exemplary embodiment shown, rigid outer support rib 172 is a separate physical component from rear limb engaging panel 130. In other exemplary embodiments, rigid outer support rib 172 may be permanently or temporarily connected with rear limb engaging panel 130. In still further exemplary embodiments, rigid outer support rib 172 may be singly manufactured with rear limb engaging panel 130.

In the exemplary embodiment shown, pivotal rear limb engaging panel 130 is pivoted to exert an even pressure and hold a residual limb in the place against front limb engaging panel 120. In a preferred exemplary embodiment, pivotal rear limb engaging panel 130 pivots at 10-40 degrees. (Persons skilled in the art will recognize that a wider range between 0 degrees and 90 degrees is feasible.) Rear limb engaging panel 130 is flexible and narrow as it is compressed in the contour of the more rigid and longer non-pivotal front limb engaging panel 120. Rigid outer support rib 172 provides structure to rear limb engaging panel 130.

As illustrated in the exemplary embodiment shown in FIG. 14, deformable inner liner 178 with silicone liner 180 is designed to fit within rigid socket assembly 210 to accommodate the individual and unique features of a residual limb to provide comfort and reduce impact. Silicone liner 180 cushions and conforms to the shape of a residual limb, while deformable inner liner 178 provides additional cushioning and support. In the exemplary embodiment shown, deformable inner liner 178 is made of cushioning material, such as deformable padding, foam, cushioning, gel, rubber or combinations of these materials. In further exemplary embodiments, deformable liner 178 may be malleable, moldable, or adjustable to specifically fit a residual limb.

While in the exemplary embodiment shown, silicone liner 180 is made of silicone, in further exemplary embodiments, silicone liner 180 may be made of any similar material known in the art. In still further exemplary embodiments, the material properties between silicone liner 180 and deformable inner liner 178 may be designed to provide added friction for augmented suspension when modular prosthetic device 1100 is firmly buckled around a residual limb.

In yet further exemplary embodiments, silicone liner 180 and deformable inner liner 178 may include a directional resistance material which allows silicone liner 180 to easily engage deformable inner liner 178 but prevents silicone liner 180 from being easily removed or shifted once in deformable inner liner 178. For example, the inner surface of deformable inner liner 178 and the outer surface of silicone liner 180 may contain an area, areas, or coating of a directionally resistive material. In still further exemplary embodiments, the outer surface of silicone liner 180 and the inner surface of deformable inner liner 178 may include engaging structures which allow silicone liner 180 to be easily inserted in deformable inner liner 178, but require additional force to remove from deformable inner liner 178.

In some exemplary embodiments, rigid socket assembly 210 and first convex plate base 135 with integrally molded longitudinal curved plate 134 may be modified to accommodate silicone liner 180 with a serrated pin suspension system, such as with the ALPS pin and gel liner suspension system known in the art.

Deformable liner 178 is shown having rear tongue 176 and a contoured front, which are adapted to comfortably receive a residual limb.

In the exemplary embodiment shown, silicone liner 180 also contains suspension straps 181a, 181b (not shown) with suspension strap buckles 182a, 182b (not shown). Suspension strap 181b with suspension strap buckle 182b is symmetrically arranged on the opposite side of silicone liner 180. In some exemplary embodiments, suspension straps 181a, 181b with suspension strap buckles 182a, 182b may be omitted, or additional or different securing components may be used.

Suspension strap buckles 182a, 182b engage corresponding suspension strap buckles 183a, 183b (not shown) on non-pivotal front limb engaging panel 120 to secure silicone liner 180 and deformable inner liner 178 to rigid socket assembly 210. In further exemplary embodiments, silicone liner 180 may be temporarily or permanently connected to rigid socket assembly 210 through any means known in the art, including clasps, clips, buckles, straps, adhesives, friction-fit components, contours, snaps, or combinations of these or other structures.

As illustrated in FIG. 14, non-pivotal front limb engaging panel 120 and pivotal rear limb engaging panel 130 are secured together around a residual limb by an intricate strap/buckle assembly comprised of buckle 122, looped cable 139, hook-shaped cable protuberances 131a, 131b, 131c and securing strap 174.

Securing strap 174 completely encircles non-pivotal front limb engaging panel 120 and pivotal rear limb engaging panel 130 and secures to rigid socket assembly 210 through securing strap apertures 175a, 175b, 175c (not shown). In the exemplary embodiment shown, securing strap 174 is made of a non-elastic material and serves as a safety strap. In further exemplary embodiments, securing strap 174 may be any material with a buckle or other structure which allows the tension on securing strap 174 to be adjusted. For example, the tension on securing strap 174 may be adjusted using buckles, clasps, clips, snaps or any other structure or combination of structures known in the art.

In the exemplary embodiment shown, securing strap aperture 175b creates a hollow opening perpendicular to the longitudinal portion of rigid outer support rib 172. Securing strap 174 is therefore able to pass completely through the longitudinal portion of rigid outer support rib 172. Securing strap aperture 175c (not shown) is symmetrically positioned on the opposite side of front limb engaging panel 120.

Similarly, looped cable 139 is connected on one end to buckle 122 and to hook-shaped cable protuberance 131c on the other end to partially encircle non-pivotal front limb engaging panel 120 and pivotal rear limb engaging panel 130. Looped cable 139 proceeds from buckle 122 through apertures 133c (not shown), 133b, 133a, and is then looped around one of hook-shaped cable protuberances 131a, 131b, 131c, depending on the size of a residual limb. As illustrated in FIG. 14, cable aperture 133b creates a hollow opening perpendicular to the longitudinal portion of rigid outer support rib 172. Looped cable 139 is therefore able to pass completely through the longitudinal portion of rigid outer support rib 172. Cable aperture 133c (not shown) is symmetrically positioned on the opposite side of non-pivotal front limb engaging panel 120.

In the exemplary embodiment shown, looped cable 139 is made of metal wire with a protective coating, such as rubber or any other moisture- and/or rust-resistant coating known in the art. Looped cable 139 goes through apertures 133a, 133b, 133c (not shown) to minimize the pressure and wear exerted on the ends of non-pivotal front limb engaging panel 120.

Once looped cable 139 is secured around one of hook-shaped cable protuberances 131a, 131b, 131c, buckle 122 is closed against front limb engaging panel 120 to pull looped cable 139 tight around rigid socket assembly 210. In the exemplary embodiment shown, buckle 122 is a buckle similar to the type traditionally used on ski boots. In further exemplary embodiments, buckle 122 may be any commercially available plastic buckle or assembly which allows leverage and tightening of looped cable 139. In still further exemplary embodiments, buckle 122 may be several buckles or securing components.

As illustrated in FIG. 14, non-pivotal front limb engaging panel 120 also contains base plate bolts 184a, 184b (not shown) and hinge bolt apertures 177a, 177b, 177c, with symmetrically arranged hinge bolt apertures 177d, 177e, 177f (not shown) on the opposite side of front limb engaging panel 120. Hinge bolt apertures 177a, 177b, 177c, and 177d (not shown), 177e (not shown), 177f (not shown) adjustably secure rigid outer support rib 172 and pivotal rear limb engaging panel 130 to non-pivotal front limb engaging panel 120.

Base plate bolts 184a, 184b (not shown) help join non-pivotal front limb engaging panel 120, and therefore a residual limb, to fitted base component 140 (not shown), containing first convex plate base 135 with integrally molded longitudinal curved plate 134. Base plate bolts 184a, 184b (not shown) project through base plate apertures 187a, 187b (not shown) in front limb engaging panel 120 and base plate apertures 85a (not shown), 185b (not shown) in fitted base component 140. Base plate aperture sets (e.g., 187a/187b and 185a/185b) are symmetrically positioned on opposite sides of their respective structural components.

Rocker connector bolts 125a, 125b, 125c (not shown) project through radial tubular portions 124a, 124b, 124c (not shown) of central hollow tubular portion 123 to secure integrally molded longitudinal curved plate 134 to concave plate base 136.

Hollow tubular portion 123 contains prosthetic pipe connector 132, which receives prosthetic device 115, which in the exemplary embodiment shown is a foot. In the exemplary embodiment shown, prosthetic pipe connector 132 is 30 mm in diameter. In further exemplary embodiments, prosthetic pipe connector 132 may have a diameter between 27 and 32 millimeters. Prosthetic device 115 is secured in hollow tubular portion 123 by set screws 129a, 129b (not shown), which project through set screw apertures 126a, 126b (not shown), and tightening bolt 128 in base clamping protuberances 127a, 127b (not shown).

Also illustrated in FIG. 14 are securing bolts 190a, 190b. Securing bolts 190a, 190b project through securing apertures 191a (not shown), 191b (not shown) in front limb engaging panel 120 and securing apertures 192a (not shown), 192b (not shown) in fitted base component 140 (not shown). Securing strap 174 also contains securing aperture 195 (not shown), which allows securing bolt 190a to vertically lock securing strap 174 in place.

In further exemplary embodiments securing strap 174 may be vertically locked in place by additional bolts or other structures, including, but not limited to, clips, clasps, buttons, or combinations of these and other structures.

Figure 15:
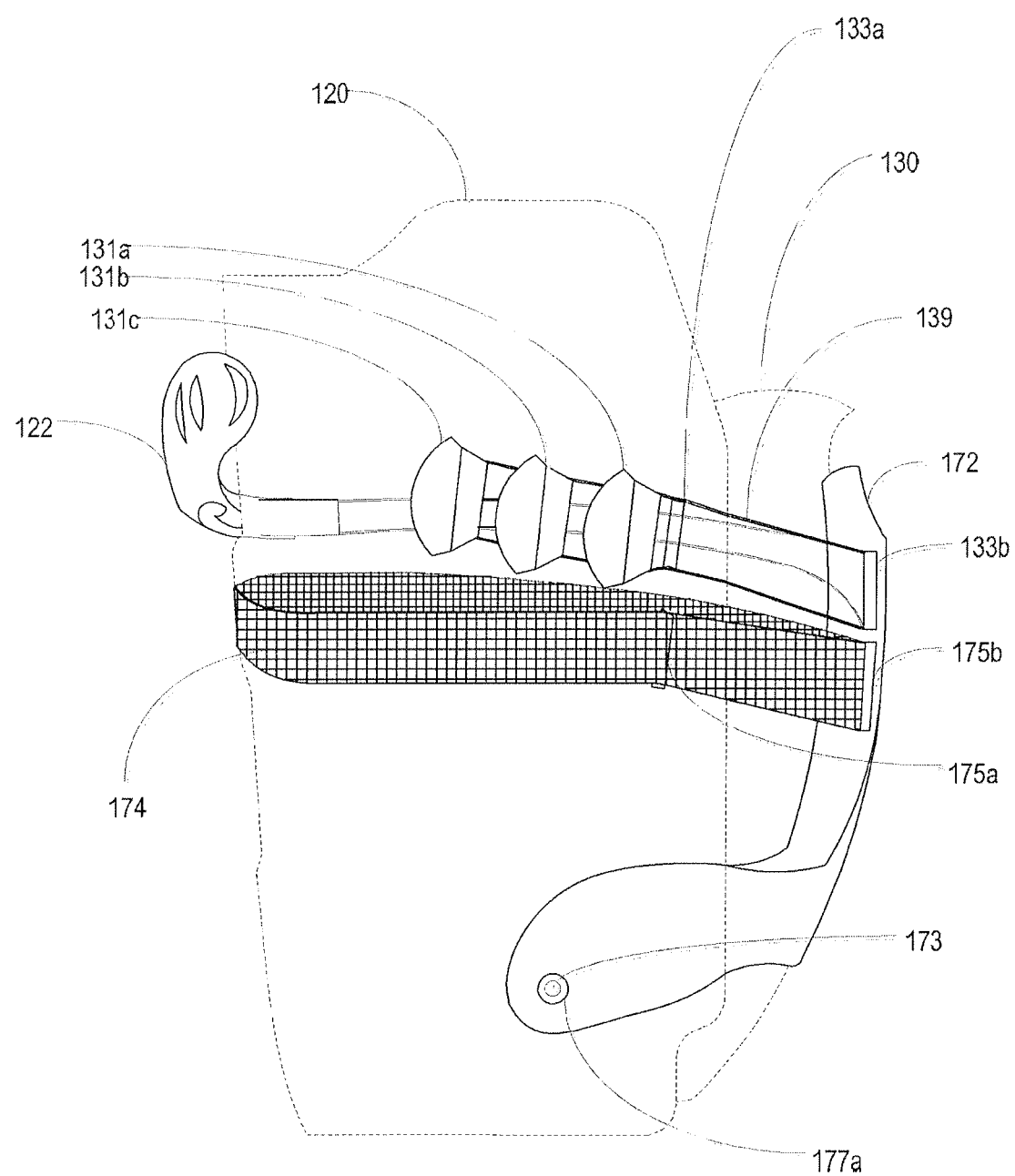
FIG. 15 illustrates an exemplary embodiment of a buckle cable system and hinge for a rapid fit modular prosthetic device for accommodating gait alignment and residual limb shape and volume.

FIG. 15 is an exemplary embodiment of a buckle/cable system of rigid socket assembly 210. The buckle/cable system secures non-pivotal front limb engaging panel 120, pivotal rear limb engaging panel 130 and rigid outer support rib 172 around a residual limb. In the exemplary embodiment shown, non-pivotal front limb engaging panel 120 and pivotal rear limb engaging panel 130 are shown in phantom to better view the components of the buckle/cable system.

As illustrated in FIG. 15, looped cable 139 is attached at one end to buckle 122. Looped cable 139 proceeds around the outside of non-pivotal front limb engaging panel 120 and goes through cable aperture 133c (not shown) on the opposite side of non-pivotal front limb engaging panel 120, and then passes through cable aperture 133b in rigid outer support rib 172. Looped cable 139 continues around the rear of rigid socket assembly 210 and passes through cable aperture 133a in non-pivotal front limb engaging panel 120. In the exemplary embodiment shown, looped cable 139 is looped around hook-shaped cable protuberance 131c, but in further exemplary embodiments, may be looped around any one of hook-shaped cable protuberances 131a, 131b, 131c, depending on the size of a residual limb. Buckle 122 tightens against non-pivotal front limb engaging panel 120 to tighten looped cable 139.

In the exemplary embodiment shown, securing strap 174 is a non-elastic component completely encircling rigid socket assembly 210. Securing strap 174 passes around the exterior of pivotal rear limb engaging panel 130 by passing through securing strap apertures 175c (not shown), 175b, 175a. Cable apertures 133a, 133b, 133c (not shown) and securing strap apertures 175a, 175b, 175c (not shown) allow looped cable 139 and securing strap 174 to tighten around rigid socket assembly 210 without putting excess pressure and strain on the edges of non-pivotal front limb engaging panel 120.

In further exemplary embodiments, rigid socket assembly 210 may contain more or fewer securing cables/straps, and securing cables or straps may have selective or continual adjustability around rigid socket assembly 210. For example, additional hook-shaped cable protuberances 131 may be available for looped cable 139. Additional tightening components, such as buckles, clasps, clips, snaps or any other structure or combination of structures, may be used to provide additional adjustment to looped cable 139 or securing strap 174.

In still further exemplary embodiments, rigid outer support rib 172 may contain additional apertures for looped cable 139 or securing strap 174.

In the exemplary embodiment shown, rigid outer support rib 172 has an inverted T-shape and is rigid to provide structural support for flexible rear limb engaging panel 130. Hinge bolt 173 projects through hinge bolt aperture 177a on non-pivotal front limb engaging panel 120, and corresponding hinge bolt apertures 117a and 118a on rear limb engaging panel 130 and rigid outer support rib 172, respectively, to attach rigid outer support rib 172 and rear limb engaging panel 130 to non-pivotal front limb engaging panel 120.

Hinge bolt 173 projects through one of hinge bolt apertures 177a, 177b (not shown), 177c (not shown), depending on the size of a residual limb. As illustrated in the exemplary embodiment shown in FIG. 15, the horizontal portion of T-shaped rigid outer support rib 172 extends against the interior of non-pivotal front limb engaging panel 120.

Rigid socket assembly 210 also contains symmetrically arranged hinge bolt apertures 177d (not shown), 177e (not shown), 177f (not shown) on the opposite side of front limb engaging panel 120, as well as symmetrically arranged hinge bolt apertures 117b (not shown), 118b (not shown) in rear limb engaging panel 130 and rigid outer support rib 172, respectively. A second hinge bolt 173 (not shown) secures rear limb engaging panel 130 and rigid outer support rib 172 to one of hinge bolt apertures 177d (not shown), 177e (not shown), 177f (not shown).

Figure 16:
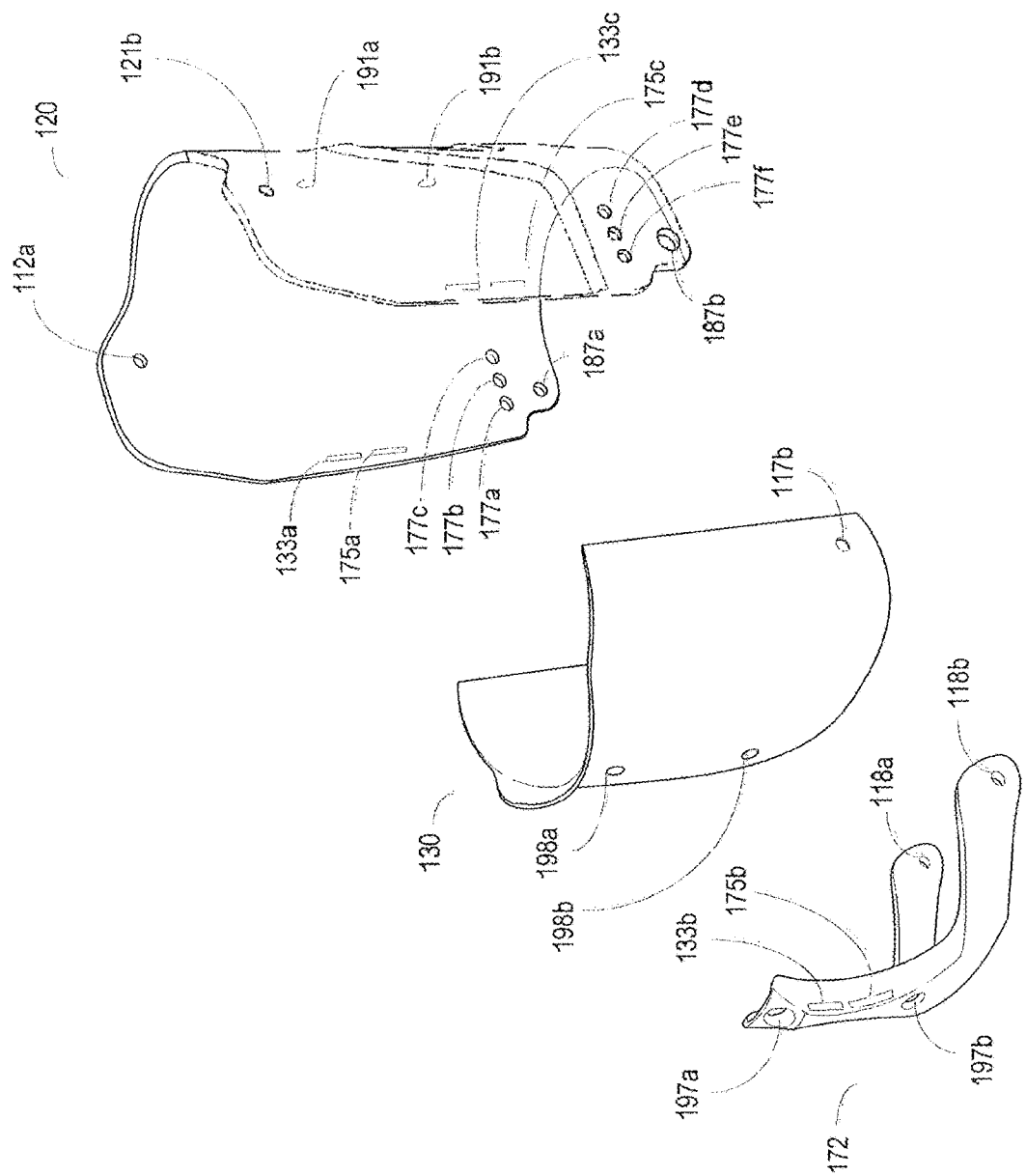
FIG. 16 illustrates an exemplary embodiment of a rigid socket assembly for a rapid fit modular prosthetic device for accommodating gait alignment and residual limb shape and volume.

FIG. 16 is an exploded view of rigid socket assembly 210. Non-pivotal front limb engaging panel 120 is shown separated from pivotal rear limb engaging panel 130 and rigid outer support rib 172. Cable apertures 133a, 133b, 133c and securing strap apertures 175a, 175b, 175c are shown without looped cable 139 (not shown) and securing strap 174 (not shown).

In the exemplary embodiment shown, rigid outer support rib 172 is a separate physical component from rear limb engaging panel 130, which securely attaches to rear limb engaging panel 130 by attachment means, such as screws or bolts, at attachment apertures 197a, 197b on rigid outer support rib and 198a, 198b on rear limb engaging panel 130. In other exemplary embodiments, rigid outer support rib 172 and rear limb engaging panel 130 may be attached by alternative structures, including, but not limited to, molding, adhesives, clips, claps, contours, or combinations of these and other attachment means.

Rigid outer support rib 172 also contains hinge bolt apertures 118a, 118b, which correspond to hinge bolt apertures 117a, 117b on rear limb engaging panel 130 and hinge bolt apertures 177a, 177b, 177c, 177d, 77e, 177f on front limb engaging panel 120. Hinge bolts 173a (not shown), 173b (not shown) engage hinge bolt aperture sets 117a/118a and 117b/118b, respectively, to adjustably and pivotally secure rigid outer support rib 172 and rear limb engaging panel 130 to front limb engaging panel 120. Hinge bolts 173a (not shown), 173b (not shown) engage one of hinge bolt apertures 177a, 177b, 177c and 177d, 177e, 177f, respectively.

In some exemplary embodiments, hinge bolts 173a (not shown), 173b (not shown) may engage symmetric hinge bolt apertures on non-pivotal front limb engaging panel 120. For example, hinge bolt 173a (not shown) may engage hinge bolt aperture 177a and hinge bolt 173b (not shown) may engage hinge bolt aperture 177f. In further exemplary embodiments, hinge bolts 173a (not shown), 173b (not shown) may engage non-symmetric hinge bolt apertures, such as 177a and 177e, respectively.

In some exemplary embodiments, hinge bolts 173a (not shown), 173b (not shown) may permanently secure rigid outer support rib 172, rear limb engaging panel 130 and front limb engaging panel 120. In other exemplary embodiments, hinge bolts 173a (not shown), 173b (not shown) may allow for selective adjustment of rigid outer support rib 172, rear limb engaging panel 130 and front limb engaging panel 120.

Base plate bolts 184a (not shown), 184b (not shown) engage base plate apertures 187a, 187b, respectively, to securely fasten front limb engaging panel 120 to fitted base component 140.

Also illustrated in FIG. 16 are attachment points 112a, 112b for suspension strap buckles 183a (not shown), 183b (not shown).

FIGS. 17a, 17b and 17c illustrate the adjustability of rigid socket assembly 210 to accommodate residual limbs of various sizes. In FIG. 17a, rigid socket assembly 210 is at its smallest size. Pivotal rear limb engaging panel 130 is recessed within front limb engaging panel 120, such that hinge bolt 173 projects through hinge bolt aperture 177c. FIG. 17b illustrates rigid socket assembly 210 with hinge bolt 173 projecting through hinge bolt aperture 177b, and FIG. 17c illustrates rigid socket assembly 210 with hinge bolt 173 projecting through hinge bolt aperture 177a.

While FIGS. 17a, 17b and 17c illustrate a single side of rigid socket assembly 210, it should be understood that front limb engaging panel 120 contains symmetrical hinge bolt apertures which are similarly engaged by a hinge bolt.

While in the exemplary embodiment illustrated in FIGS. 17a, 17b and 17c, the adjustability of rigid socket assembly 210 is limited to three pre-determined sizes, in further exemplary embodiments, additional hinge bolt apertures 177 may be provided for additional adjustability. In still further exemplary embodiments, a structure other than a hinge bolt may be used to provide continuous adjustability.

Figure 18A:
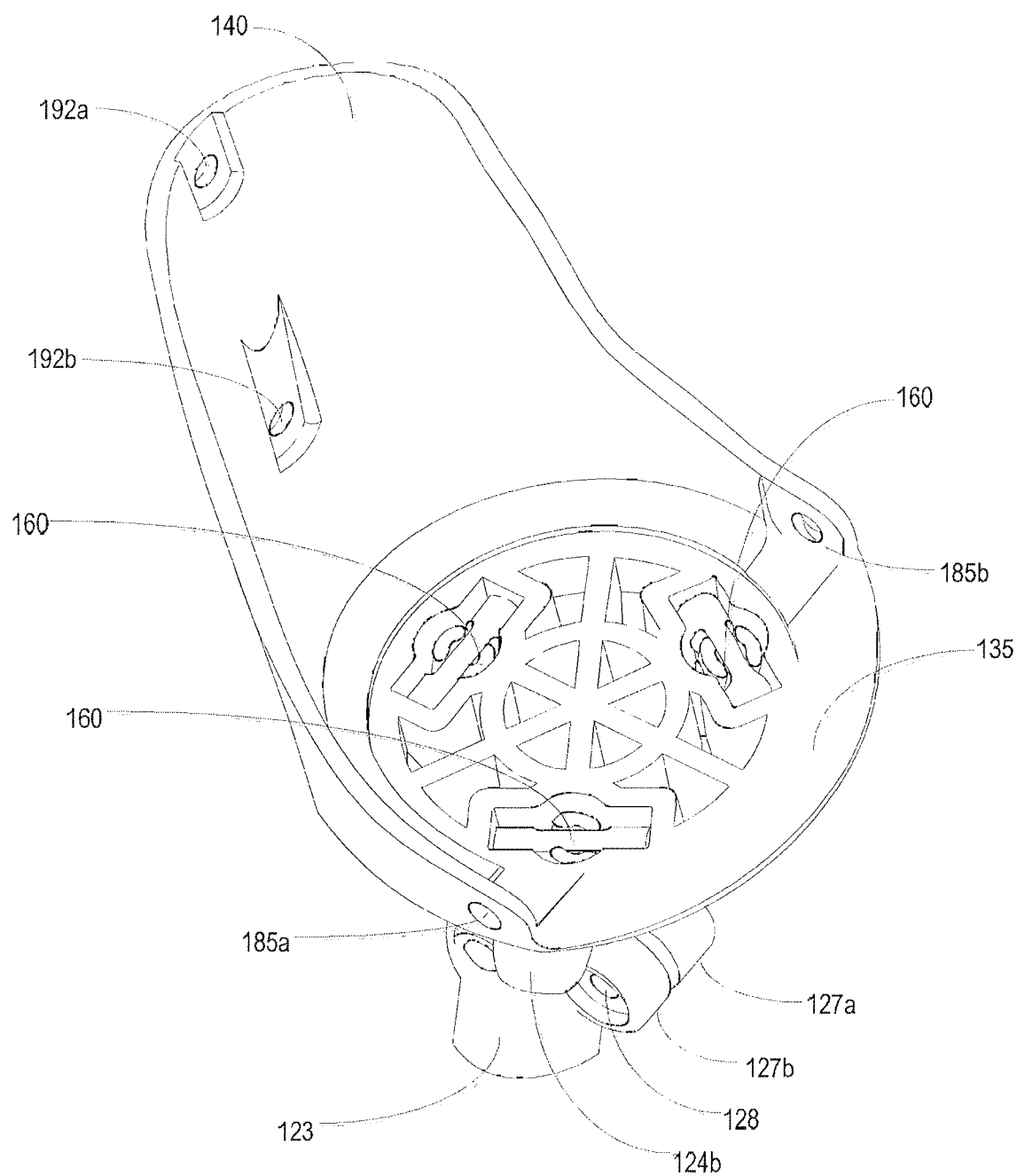
FIG. 18a illustrates an exemplary embodiment of a base component assembly for a rapid fit modular prosthetic device for accommodating gait alignment and residual limb shape and volume.
Figure 18B:
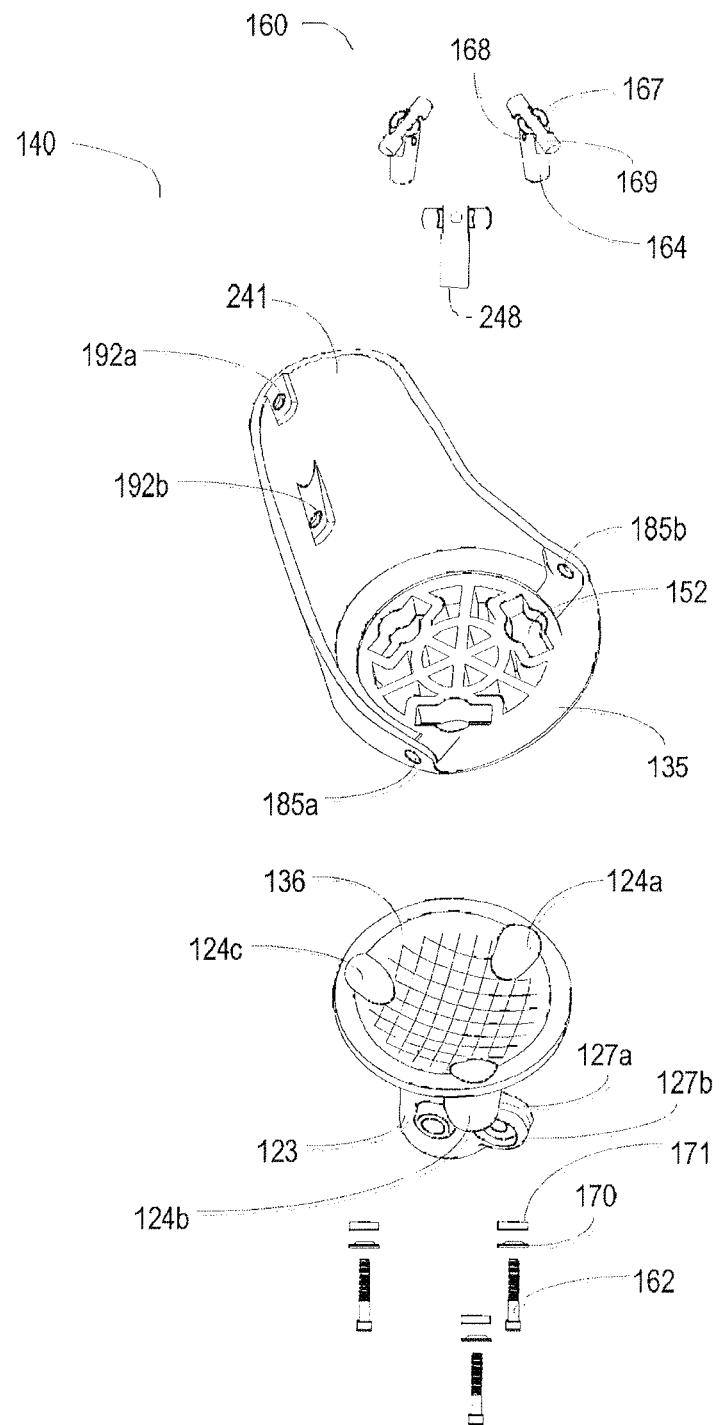
FIG. 18b illustrates an exploded view of an exemplary embodiment of a base component assembly for a rapid fit modular prosthetic device for accommodating gait alignment and residual limb shape and volume.

FIGS. 18a and 18b show the construction of an exemplary fitted base component 140. FIG. 18a illustrates an assembled fitted base component 140, with first convex plate 135 and rocker bolt assemblies 160 visible. As illustrated in FIG. 18a, convex plate 135 is an integral component with fitted base component 140 and is the top surface of fitted base component 140.

Rocker bolt assemblies 160 engage radial tubular portions 124a (not shown), 124b, 124c (not shown). Base plate bolts 184a (not shown), 184b (not shown) project through base plate apertures 185a, 185b to secure non-pivotal front limb engaging panel 120 (not shown) to fitted base component 140. When assembled, base plate apertures 185a, 185b align with base plate apertures 187a (not shown), 187b (not shown) of front limb engaging panel 120 (not shown).

Securing apertures 192a, 192b are adapted to receive securing bolts 190a (not shown), 190b (not shown), respectively, to secure fitted base component 140 to front limb engaging panel 120 (not shown).

In the exemplary embodiment shown, first convex plate 135 is constructed of a weight-bearing material.

Also illustrated in FIG. 18a are base clamping protuberances 127a, 127b with tightening bolt 128. Tightening bolt 128 pulls base clamping protuberances 127a, 127b closer together to tightly engage the pipe of a prosthetic device. In the exemplary embodiment shown, base clamping protuberances 127a, 127b are specifically designed to remain approximately 28-32 mm apart after tightening bolt 128 is tightened.

FIG. 18b is an exploded view of an exemplary fitted base component 140. Rocker bolt assemblies 160 are made of hollow threaded socket 164 with u-shaped upper portion 167 adapted to receive contoured horizontal rod 169, threaded hex bolt component 162 with convex collar washer 170 and concave funnel-shaped washer 171, and pivot pin 168. Pivot pin 168 is shown on hollow threaded socket 164 and secures contoured horizontal rod 169 to hollow threaded socket 164. Rocker bolt assemblies 160 rest in rocker bolt apertures 152 of first convex plate 135 and are unable to fall through rocker bolt apertures 152 because of contoured horizontal rod 169.

Hollow threaded socket 164 projects into radial tubular portions 124a, 124b, 124c of concave base plate 136, allowing threaded hex bolt component 162 to tighten within hollow threaded socket 164. Convex collar washer 170 and concave funnel-shaped washer 171 are secured between hollow threaded socket 164 and threaded hex bolt component 162.

In the exemplary embodiment shown, there are three rocker bolt assemblies 160, and radial tubular portions 124a (not shown), 124b, 124c (not shown), with corresponding rocker bolt apertures 152, are symmetrically arranged around concave base plate 136 and first convex plate base 135, respectively. In further exemplary embodiments, additional rocker bolt assemblies 160 may be used, and radial tubular portions 124 and rocker bolt apertures 152 may be unevenly distributed around the perimeter of concave base plate 136 and first convex plate base 135.

Base plate apertures 185a, 185b and securing bolt apertures 192a, 192b are also shown in fitted base component 140. Base plate bolts 184a, 184b (not shown) project through base plate apertures 185a, 185b and corresponding base plate apertures 187a (not shown), 187b (not shown) on non-pivotal front limb engaging panel 120 (not shown) to secure non-pivotal front limb engaging panel 120 (not shown) to fitted base component 140. Similarly, securing bolts 190a (not shown), 190b (not shown) project through securing bolt apertures 191a (not shown), 191b (not shown) on non-pivotal front limb engaging panel 120 and securing bolt apertures 192a, 192b to provide additional support in securing fitted base component 140 to rigid socket assembly 210 (not shown).

Rocker bolt assemblies 160 secure first convex plate base 135 to concave plate base 136. In the exemplary embodiment shown, concave plate base 136 is adapted to receive the lower surface of first convex plate base 135.

Figures 19A, 19B:
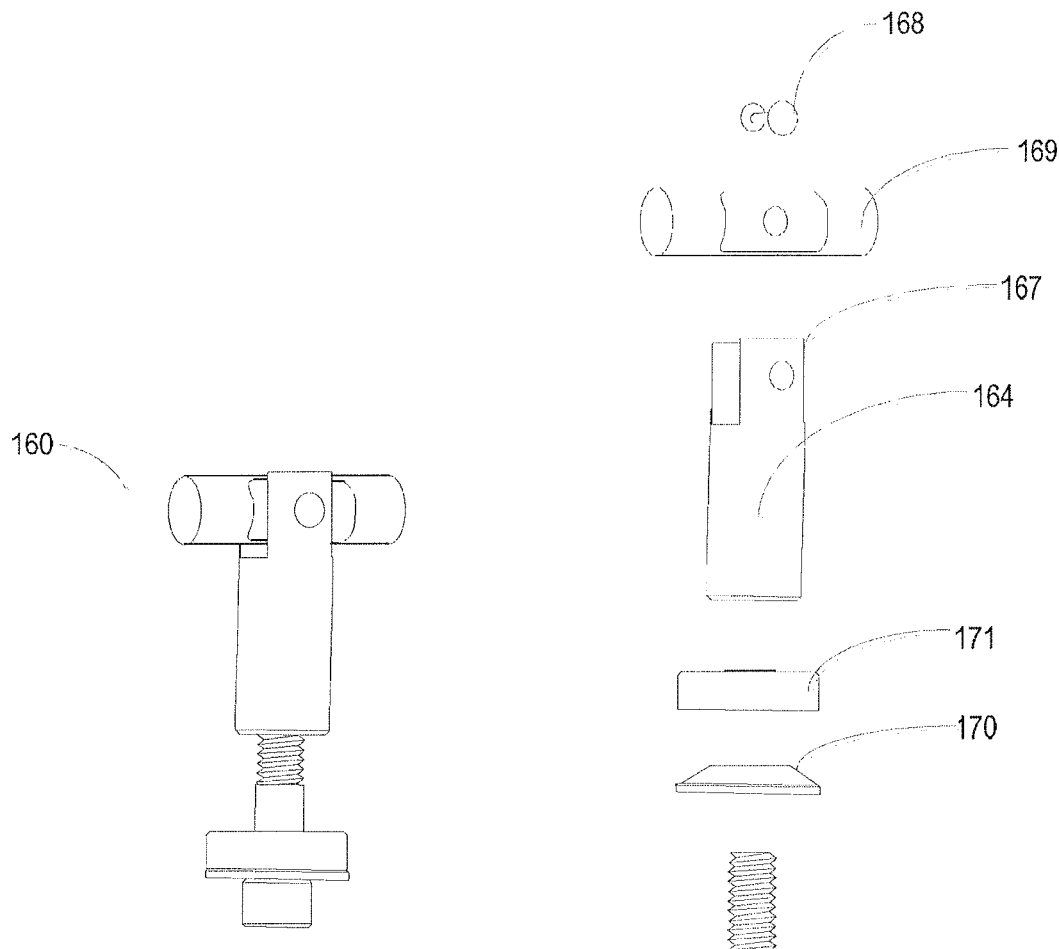
FIG. 19a illustrates an exemplary embodiment of a rocker bolt assembly.
FIG. 19b illustrates an exploded view of an exemplary embodiment of a rocker bolt assembly.

FIGS. 19a and 19b illustrate an exemplary rocker bolt assembly 160 in more detail. As illustrated, rocker bolt assembly 160 is comprised of pivot pin 168, contoured horizontal rod 169, hollow threaded socket 164 with u-shaped upper portion 167, concave funnel-shaped washer 171, convex collar washer 170 and threaded hex bolt component 162.

Pivot pin 168 pivotally secures contoured horizontal rod 169 to hollow threaded socket 164. Contoured horizontal rod 169 is therefore allowed to pivot relative to hollow threaded socket 164. In the exemplary embodiment shown, horizontal rod 169 can pivot up to 120 degrees relative to hollow threaded socket 164. Threaded hex bolt component 162 screws into hollow threaded socket 164, with concave funnel-shaped washer 171 and convex collar washer 170 secured between threaded hex bolt component 162 and hollow threaded socket 164. The construction of rocker bolt assembly 160 allows for limited movement between first convex base plate 135 and concave base plate 136.

In further exemplary embodiments, contoured horizontal rod 169 may be secured to hollow threaded socket 164 with a different securing structure. For example, contoured horizontal rod 169 may be friction fit or use a spring-pin mechanism or other structure which may pivotally secure horizontal rod 169 to hollow threaded socket 164. Different constructions of rocker bolt assemblies 160 may allow for increased movement or pivoting.

Figure 20A:
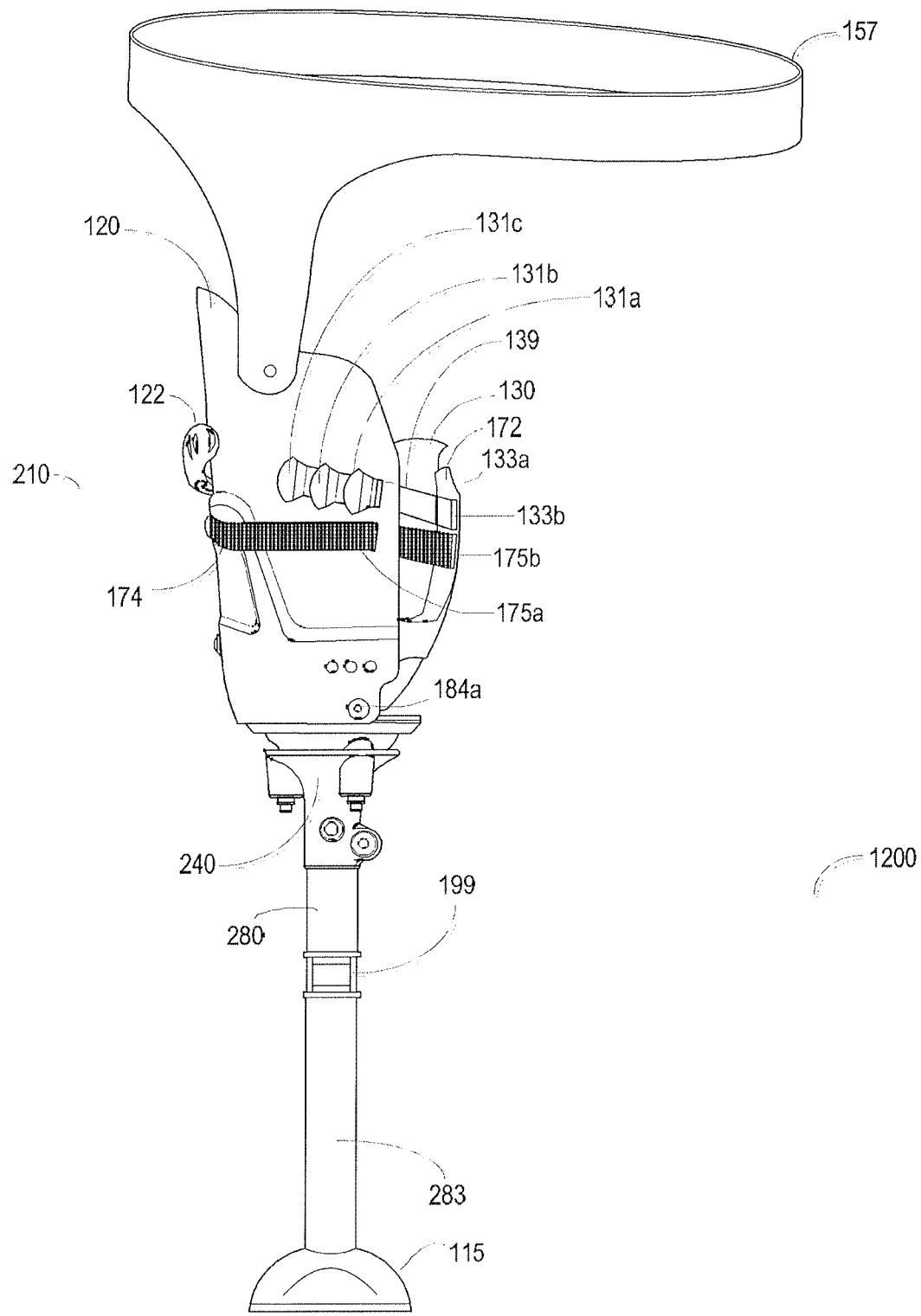
FIG. 20a is an exemplary embodiment of a rapid fit modular prosthetic device/prosthesis system for accommodating gait alignment and residual limb shape and volume for an above-the-knee residual limb.

FIG. 20a illustrates an exemplary embodiment of rapid fit modular prosthetic device for accommodating gait alignment and residual limb shape and volume adapted for an above-the-knee residual limb 1200. As illustrated, rapid fit modular prosthetic device for accommodating gait alignment and residual limb shape and volume for an above-the-knee residual limb 1200 is very similar to rapid fit modular prosthetic device for accommodating gait alignment and residual limb shape and volume for a below-the-knee residual limb 1100. However, the components of rigid socket assembly 210 may be larger to accommodate the larger size of an above-the-knee residual limb, and prosthetic device 115 includes knee 199. The entire rapid fit modular prosthetic device for accommodating gait alignment and residual limb shape and volume 1200 is also rotated 90 degrees compared to the orientation for a below-the-knee residual limb.

Rapid fit modular prosthetic device for accommodating gait alignment and residual limb shape and volume 1200 also includes waist strap 157 to help stabilize and secure rapid fit modular prosthetic device for accommodating gait alignment and residual limb shape and volume 1200.

In the exemplary embodiment illustrated in FIG. 20a, front limb engaging panel 120 and rigid outer support rib 172 are larger to accommodate a larger residual limb. Front limb engaging panel 120, specifically, needs to be taller in order to properly secure an above-the-knee residual limb. In the exemplary embodiment shown, non-pivotal front limb engaging panel 120 is 6 cm higher. Because of the way pressure is exerted on rapid fit modular prosthetic device for accommodating gait alignment and residual limb shape and volume 1200 by an above-the-knee residual limb, additional stabilizing is needed by front limb engaging panel 120. In other exemplary embodiments, rigid outer support rib 172 may be larger or of a more flattened shape to reduce projection between the legs.

In some exemplary embodiments, cable apertures 133a, 133b and securing strap apertures 175a, 175b may be positioned differently on front limb engaging panel 120 and rigid outer support rib 172 to create additional stability in securing rapid fit modular prosthetic device for accommodating gait alignment and residual limb shape and volume 1200 to a larger residual limb.

As illustrated, rapid fit modular prosthetic device for accommodating gait alignment and residual limb shape and volume 1200 contains an intricate strap/buckle system identical to that of rapid fit modular prosthetic device for accommodating gait alignment and residual limb shape and volume 1100. However, in further exemplary embodiments, rapid fit modular prosthetic device for accommodating gait alignment and residual limb shape and volume 1200 may contain additional looped cables 139, securing straps 174, buckles 122 or other securing members.

In the exemplary embodiment shown, looped cable 139 is looped around hook-shaped cable protuberance 131*b*, which creates a larger volume inside the recess created by non-pivotal front limb engaging panel 120 and pivotal rear limb engaging panel 130. In further exemplary embodiments, looped cable 139 may be secured using any of hook-shaped cable protuberances 131*a*, 131*b*, 131*c*.

Figure 20B:
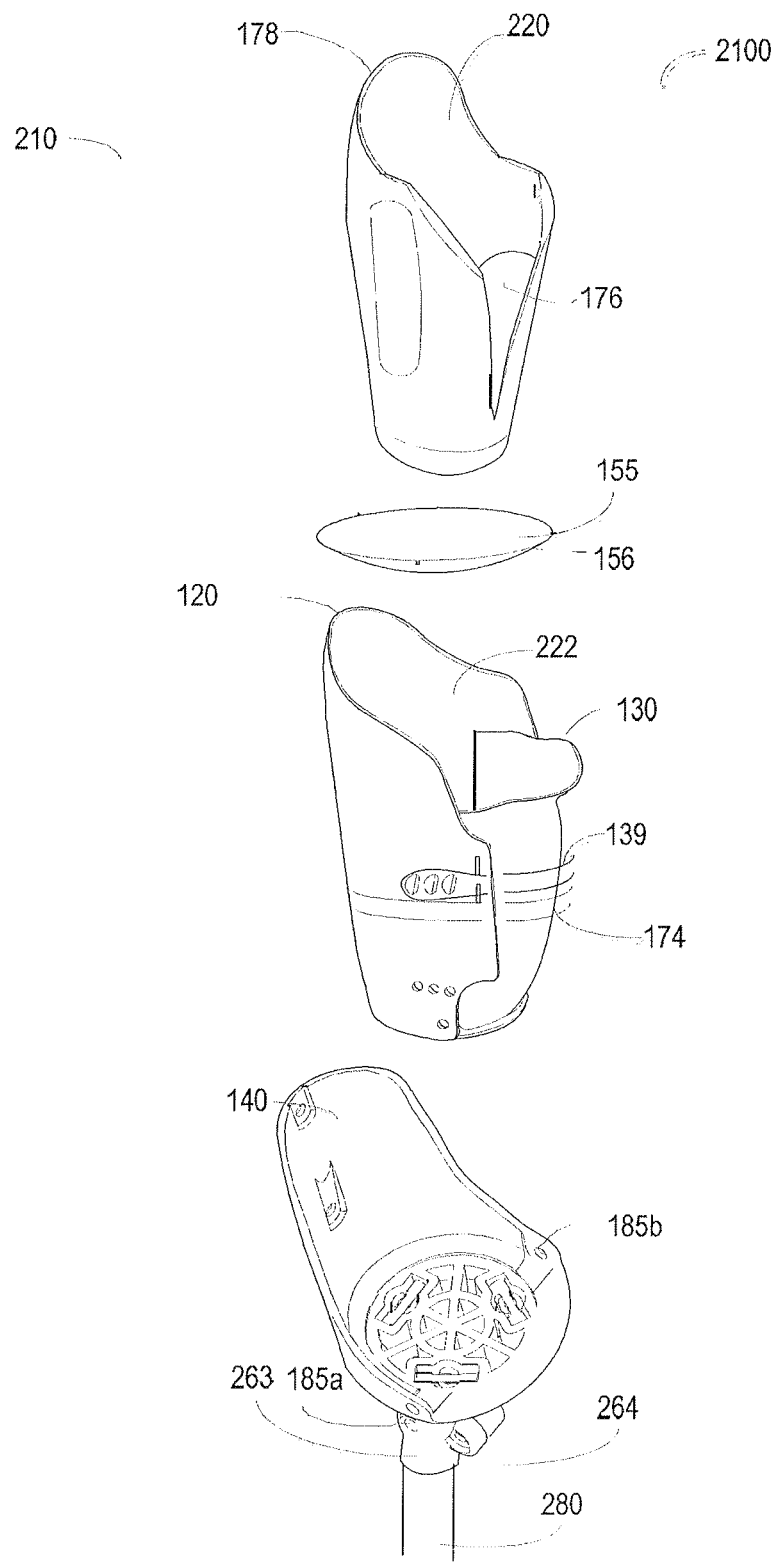
FIG. 20b is an exploded view of the above-the-knee components of an exemplary rapid fit modular prosthetic device for accommodating gait alignment and residual limb shape and volume.

FIG. 20*b* illustrates additional differences between rapid fit modular prosthetic device for accommodating gait alignment and residual limb shape and volume for above-the-knee residual limbs 1200 and rapid fit modular prosthetic device for accommodating gait alignment and residual limb shape and volume 1100 for below-the-knee residual limbs.

As illustrated, deformable inner liner 178 with rear tongue 176 does not contain a silicone liner. In further exemplary embodiments, deformable inner liner 178 may contain or utilize a liner made of silicone or other similar materials. Support cup 155, with support cup connectors 156, is inserted in rigid socket assembly 210 under deformable liner 178 to provide height adjustments.

In below-the-knee embodiments, the distance from a user's residual limb to the bottom of the prosthetic device is adjusted by the length of the pipe on the prosthetic device. However, in above-the-knee embodiments, the distance from a user's residual limb to the prosthetic knee must also be adjusted. Support cup 155 may be placed at any height in the tubular recess created by rigid socket assembly 210 to support a user's residual limb at the necessary height.

Support cup connectors 156 engage the interior surface of non-pivotal front limb engaging panel 120 to secure support cup 155. In the exemplary embodiment shown, support cup connectors 156 are screws which are screwed to both non-pivotal front limb engaging panel 120 and pivotal rear limb engaging panel 130. However, in further exemplary embodiments, support cup connectors 156 may be any securing structure or device known in the art, including, but not limited to, clips, clasps, braces, brackets, bolts, adhesives, friction-fit components, contours, and combinations of these and other structures. In still further exemplary embodiments, support cup 155 may be permanently, releasably or adjustably secured to rigid socket assembly 210.

In the exemplary embodiment shown, base plate apertures 185*a*, 185*b* are visible on both non-pivotal front limb engaging panel 120 and fitted base component 140. Base plate bolts 184*a*, 184*b* (not shown) project through base plate apertures 185*a*, 185*b* to secure non-pivotal front limb engaging panel 120 to fitted base component 140.

Figure 21:
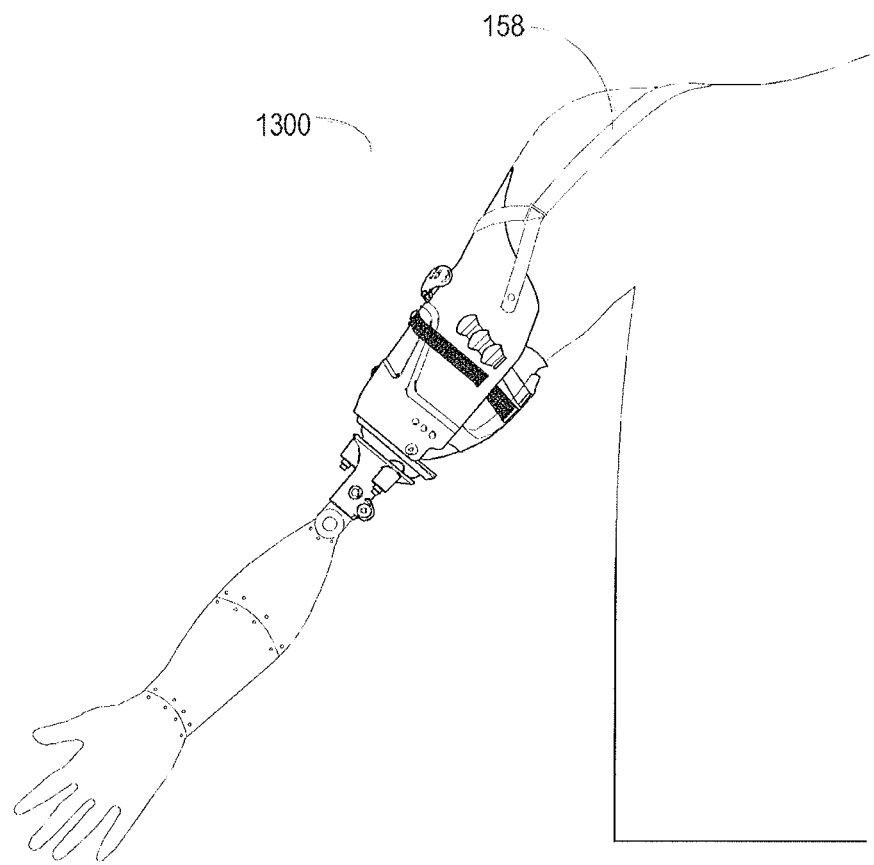
FIG. 21 illustrates an exemplary embodiment of a rapid fit modular prosthetic device for accommodating gait alignment and residual limb shape and volume adapted for use on arm-related residual limbs.

FIG. 21 illustrates rapid fit modular prosthetic device for accommodating gait alignment and residual limb shape and volume 1300 for use on a residual limb which is an arm. As illustrated, rapid fit modular prosthetic device for accommodating gait alignment and residual limb shape and volume 1300 contains basically identical structures as rapid fit modular prosthetic device for accommodating gait alignment and residual limb shape and volume 1100 for a below-the-knee residual limb and rapid fit modular prosthetic device for accommodating gait alignment and residual limb shape and volume 1200 for an above-the-knee residual limb. However, in the exemplary embodiment illustrated, rapid fit modular prosthetic device for accommodating gait alignment and residual limb shape and volume 1300 includes shoulder strap 158 to secure rapid fit modular prosthetic device for accommodating gait alignment and residual limb shape and volume 1300 to a residual limb which is an arm.

FIG. 20*a* illustrates an exemplary embodiment of an above-the-knee modular prosthesis system 1200. As illustrated in FIG. 20*a*, modular prosthesis system 1200 includes universal outer housing 210, consisting of soft inner liner 220 (not shown) and outer shell 120.

Closure components 139, 174 on outer shell 120 allow outer shell 120 to be adjusted to the circumference of an amputee's residual limb. In the exemplary embodiment shown, closure component 139 is a looped wire running from buckle 122 to secure around one of hook-shaped protuberances 131*b*, and closure component 174 is a strong non-elastic strap completely encircling outer shell 120 and serves as a safety strap. In further exemplary embodiments, outer shell 120 may contain any number of closure components, and closure components may be any structure or device known in the art to allow width adjustability of outer shell 22. For example, closure components may include, but are not limited to, buttons, snaps, clasps, clips, elastic components, buckles, laces, ties, interlocking components, hook-and-loop fasteners, hook-and-eye fasteners, hook-shaped components, and any combination of these and other structures and devices.

Universal outer housing 210 releasably secures to connector assembly 240 and connecting tube 280. Suspension component 157, which in the exemplary embodiment shown is a waist strap, helps an amputee more securely hold modular prosthesis system 1200 to a residual limb. In further exemplary embodiments, suspension component 157 may be any adjustable securing component or device known in the art, including, but not limited to, suspenders, belts, clasps or other attachment means which releasably attach to a user's clothing or existing belt, or any combination of these and other structures.

In some exemplary embodiments, suspension component 157 may contain additional elements to create a suspension system. For example, a liner or sleeve which fits over a residual limb may be provided with suspension component 157. In further exemplary embodiments, a liner or sleeve may include a cushioning gel substance or other component. In still further embodiments, a liner or sleeve may contain directionally frictional materials which allow the liner or sleeve to easily slide into outer housing 210, but require additional force to be removed from outer housing 210.

In yet further exemplary embodiments, outer housing 210 and connector assembly 240 may be adapted to accommodate a liner or sleeve with a serrated pin suspension system, such as the ALPS pin and gel liner suspension system known in the art.

In the exemplary embodiment shown, universal outer housing 210 is a single unit constructed of rigid plastic. In further exemplary embodiments, outer housing 210 may be multiple separate components molded or joined together, such as with closure components 139, 174. In still other exemplary embodiments, outer housing 210 may be constructed of a stronger material, such as metals, or materials specifically designed to withstand the pressure and wear caused by an amputee's activities. Closure components 139, 174 may be selected based on the material of outer housing 210 or the specific forces generated by an individual amputee's residual limb.

In the exemplary embodiment shown in FIG. 20*a*, connector tube 280 connects to prosthetic knee 199, which connects to below-the-knee shank 283, which is a standard below-the-knee shank known in the art and provides height adjustment for the distance from knee 199 to the prosthetic device 115 which contacts the ground.

Figure 22:
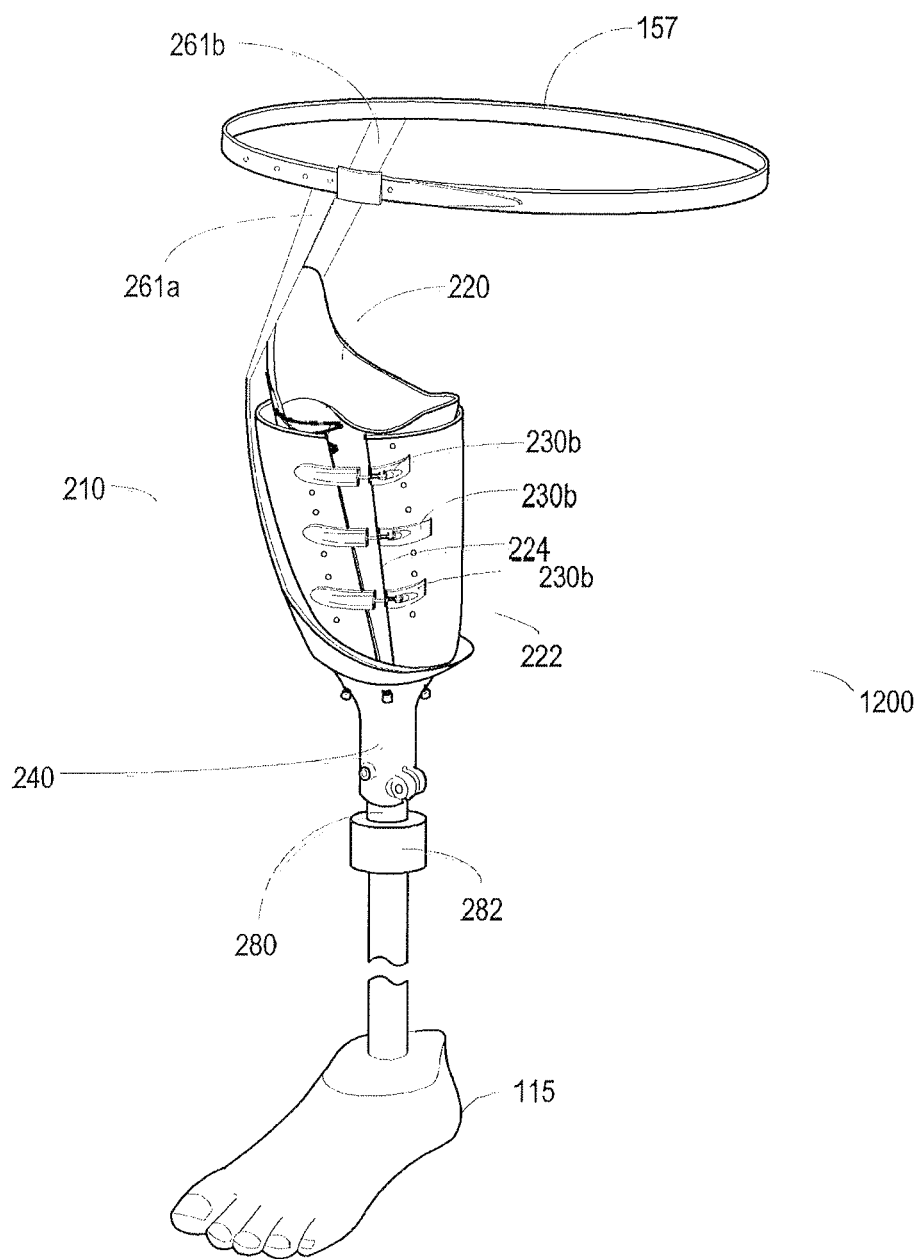
FIG. 22 illustrates an alternative embodiment of an above-the-knee modular prosthesis system with soft inner liner.

FIG. 22 illustrates an alternative embodiment of an above-the-knee modular prosthesis system 1200 with soft inner liner 220. In the exemplary embodiment shown, soft inner liner 220 fits within the cavity created by outer shell 222 and provides comfortable support for a residual limb. Soft inner liner 220 may also decrease the internal volume of the cavity created by outer shell 222 to help accommodate a residual limb having a smaller circumference.

In the exemplary embodiment shown, inner liner 220 is created of a deformable material, such as cushion, foam, gel or other pillow-like material which deforms to specifically contour a residual limb. In other exemplary embodiments, inner liner 220 may be custom-made to fit a specific residual limb.

As illustrated in FIG. 22, suspension component 157 is a belt with two side straps 261a, 261b which attach to outer housing 210. In other exemplary embodiments, side straps 261a, 261b may be attached to inner liner 220.

In the exemplary embodiment shown, outer housing 210 contains three identical closure components 230b which are buckles. Closure components 230b tighten against outer shell 222 to close gap 224 and apply pressure around a residual limb to keep it in outer housing 210. In further exemplary embodiments, closure components may each be different. In yet further exemplary embodiments, closure components may be specifically designed or positioned to apply pressure at specific points around a residual limb.

Outer housing 210 attaches to connector 240, which in the exemplary embodiment shown is adjustable for making angular adjustments. For example, connector 240 may be able to tilt backwards, forwards and/or to the sides to account for differences in an individual's gait and natural bone alignment. Connector 240 provides adjustment of the angle of the prosthesis and leg on the amputee to optimally align the prosthesis. After it is adjusted and put into the proper position angle, connector 240 is tightly secured in place such that it provides a stable and non-movable attachment for safe ambulation.

Connector 240 attaches outer housing 210 to connector pipe 280, which is a standard diameter pipe connector known in the art. In the exemplary embodiments shown in FIGS. 20a and 22, connector 280 is drawn attached to knee component 282, which connects via shank 283 to a foot-like prosthetic limb. In further exemplary embodiments, shank 283 may be any prosthetic shank known in the art.

Figure 23:
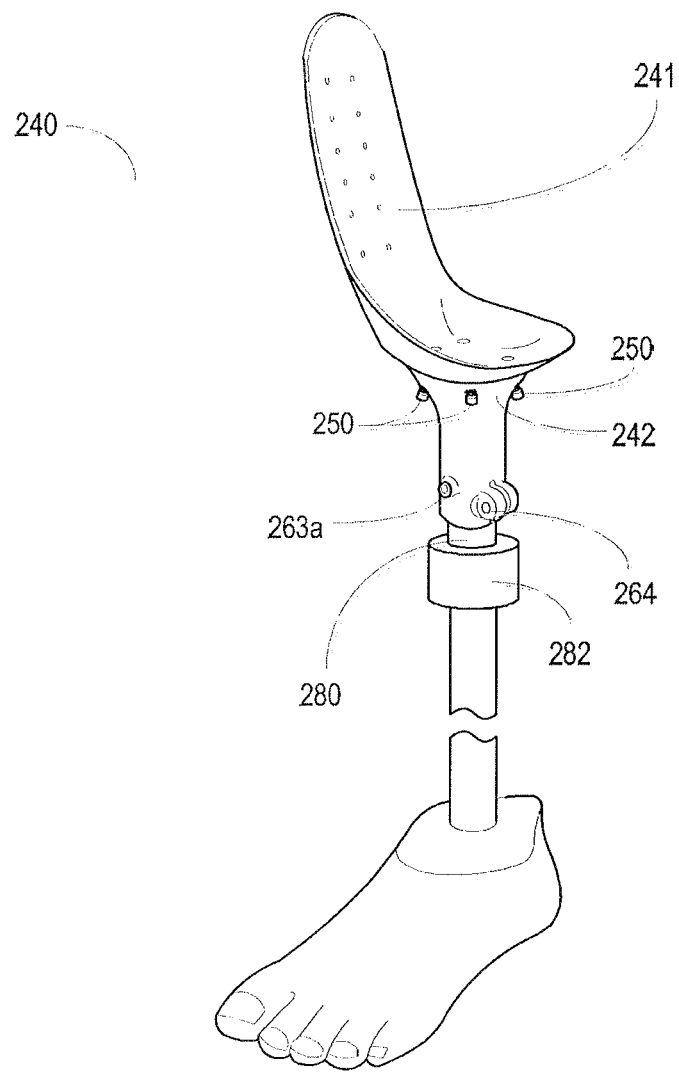
FIG. 23 illustrates an exemplary connector assembly for a modular prosthesis system.

FIGS. 23 and 18a illustrate exemplary connector assemblies 240, 140 for a modular prosthesis system 1200.

As illustrated in FIG. 23, connector assembly 240 includes upper plate 241 and lower plate 242 joined by bolts 250. Lower plate 242 contains an inner tubular recess for receiving connector pipe 280. Set screws 263a and 263b (not shown) and tightening bolt 264 help tighten connector pipe 280 to connector assembly 240.

Bolts 250 allow for gait adjustability. When a residual limb is secured in outer housing 210 (not shown), outer housing 210 (not shown) is securely attached to upper plate 241. Upper plate 241 and lower plate 242 may be pivotally adjustable, relative to each other, to conform modular prosthesis system 1200 to a specific individual. In further exemplary embodiments, upper plate 241 and lower plate 242 may contain a limited degree of rotational adjustability. Bolts 250 allow an amputee to account for differences in bone structure, curvature, and alignment.

FIG. 18b is an alternative exemplary connector assembly 140. Upper plate 241 connects to lower plate 136 using specialized bolts comprised of a hollow, pivotal female end 248 with threaded male end 162. Washers 171 may be optionally included with male end 162. Pivotal female ends 248 project downwards through bolt apertures 152, and male ends 162 project upwards through corresponding bolt channels 124a to engage female ends 248. Pivotal female ends 248 allow limited movement and adjustability of upper plate 241 relative to lower plate 136.

In the exemplary embodiment illustrated, once a desired position has been reached, the pivotal bolts assemblies may be tightened into place, permanently or adjustably, to prevent upper plate 241 and lower plate 136 from moving under the forces exerted by a residual limb and movement of an amputee. In further exemplary embodiments, upper plate 241 and lower plate 136 may be secured together with a limited amount of allowable movement for such things as absorbing excessive gait forces.

While upper plate 241 and lower plate 136 are illustrated as joined by three pivotal bolt assemblies, in further exemplary embodiments, upper plate 241 and lower plate 136 may be adjustably attached through any structure or device known in the art, including, but not limited to, screws, pins, bolts, interlocking components, or any combination of these and other structures or devices.

Both FIGS. 23 and 18b show different structures to provide limited adjustability of modular prosthetic system 1200 to account for differences in bone structure, shape and alignment, as well as differences in gait, to create a custom-like fit for each amputee.

In some exemplary embodiments, as illustrated in FIG. 18b, upper plate 241 and/or lower plate 136 may contain surface textures which may facilitate or incrementally limit the adjustability of connector assembly 240. As shown in FIG. 18b, lower plate 136 contains a grid pattern which corresponds to a similar grid pattern on the under-surface of upper plate 241. The corresponding grid patterns create a plurality of locations to which connector assembly 240 may be positioned. When the grid-like surfaces connect, the position is more stable and resistant to change when experiencing the various forces applied to connector assembly 240 by a residual limb and the general movement of an amputee.

FIG. 20b is an exploded view of an exemplary above-the-knee modular prosthesis system 1200. Soft inner liner 220 is removed from outer shell 222. In some exemplary embodiments, soft inner liner 220 may contain closure components, such as laces, buckles, hook-and-eye fasteners, hook-and-loop fasteners or other structures or combinations of structures known in the art to secure soft inner liner 220 around a residual limb. As illustrated, outer shell 222 contains closure components 139, 174, which are a looped cable and securing band, as shown in FIG. 20a. Height adjustment component 155 is shown between inner liner 220 and outer shell 222. Connector assembly 140 contains connector 280, rotationally and vertically secured in place by set screw 263 and tightening bolt 264.

In the exemplary embodiment shown, height adjustment component 155 is a plate which may be positioned within outer shell 222 to adjust for the distance between a residual limb and the natural location of a knee joint. As illustrated, height adjustment component 155 is friction-fit within outer shell 222. In further exemplary embodiments, height adjustment component 155 may contain pins, bolts, or other structures adapted to project through outer shell 222, creating a more permanent adjustment. In still further exemplary embodiments, outer shell 222 may contain a plurality of pre-determined height-adjustment locations to which height adjustment component 155 may be secured.

In further exemplary embodiments, height adjustment component 155 may also be used to adjust to the angle of a residual limb and therefore alter the angle at which modular prosthetic system 1200 is attached. For example, height adjustment component 155 may be pivotally attached to outer shell 222, or secured to outer shell 222 at an angle.

In some exemplary embodiments, height adjustment component 155 may be made of a solid material, such as plastics or metals. In further exemplary embodiments, height adjustment component 155 may contain a form of cushioning or padding to decrease the pressure on a residual limb. However, height adjustment component 155 will need to be able to support the weight of an amputee.

In further exemplary embodiments, when height adjustment is not necessary, height adjustment component 155 may be omitted. In yet further exemplary embodiments, an additional cushion or padded component may be placed between inner liner 220 and outer shell 222.

In yet further exemplary embodiments, inserts and adjustment components of various shapes, sizes and contours may be added to adjust for a residual limb's circumference, volume, size, angle, and other properties. For example, modular prosthetic system 1200 may include height adjustment components, volume adjustment components, angle adjustment components, circumference adjustment components and combinations of such adjustment components. By providing modular adjustment components, modular prosthetic system 1200 may be manufactured in a standard size, or select standard sizes, yet adjusted to provide a near custom fit for each residual limb. For example, universal outer housing 210 may be manufactured in three sizes, with variations in soft inner liner 220 and height adjustment component 155 and the adjustability provided by closure components 139, 174 and other components creating a wide range of sizes.

In the exemplary embodiments described, components of modular prosthetic system 1200 may be disposable. For example, the various liners, pads and adjustment components may be specifically designed to be quickly and easily changed and disposable as an amputee's residual limb changes size or shape. In other exemplary embodiments, components of modular prosthetic system 1200 which experience wear may be designed to be replaced and disposed as they weaken.

In other exemplary embodiments, components of modular prosthetic system 1200 may be specifically designed and manufactured for efficient shipping. For example, liners, shells and other components may be specifically designed to nest within each other, saving room during shipping. Other components, such as bolts, screws and closure components, may also be assembled for shipping.

Modular prosthetic system 1200 also allows a prosthetic limb to be quickly and securely attached to a residual limb. The adjustability of the various components provides a quick way to create a custom-like fit by accounting for differences in residual limb shape, circumference, volume and general size, as well as differences in gait, bone structure and bone alignment. Because it is not necessary to create custom pieces or molds, modular prosthetic system 1200 may be implemented immediately.

Another exemplary embodiment of Applicant's adjustable prosthesis system 1400 is illustrated in FIGS. 24-28. The system includes an outer shell 310, one or more closure components (not shown), such as a strap(s), buckle(s), or clasp(s), an inner liner 378, and an adjustable connector assembly 340, which connects the adjustable outer shell 310 to a shank 332 or another prosthetic device in a manner discussed in more detail below in view of FIGS. 28A and 28B. The system also may include a locking pin 386 and a locking mechanism 395, which also are discussed below in connection with the connector assembly 340 illustrated in FIGS. 28A and 28B.

Figure 26A:
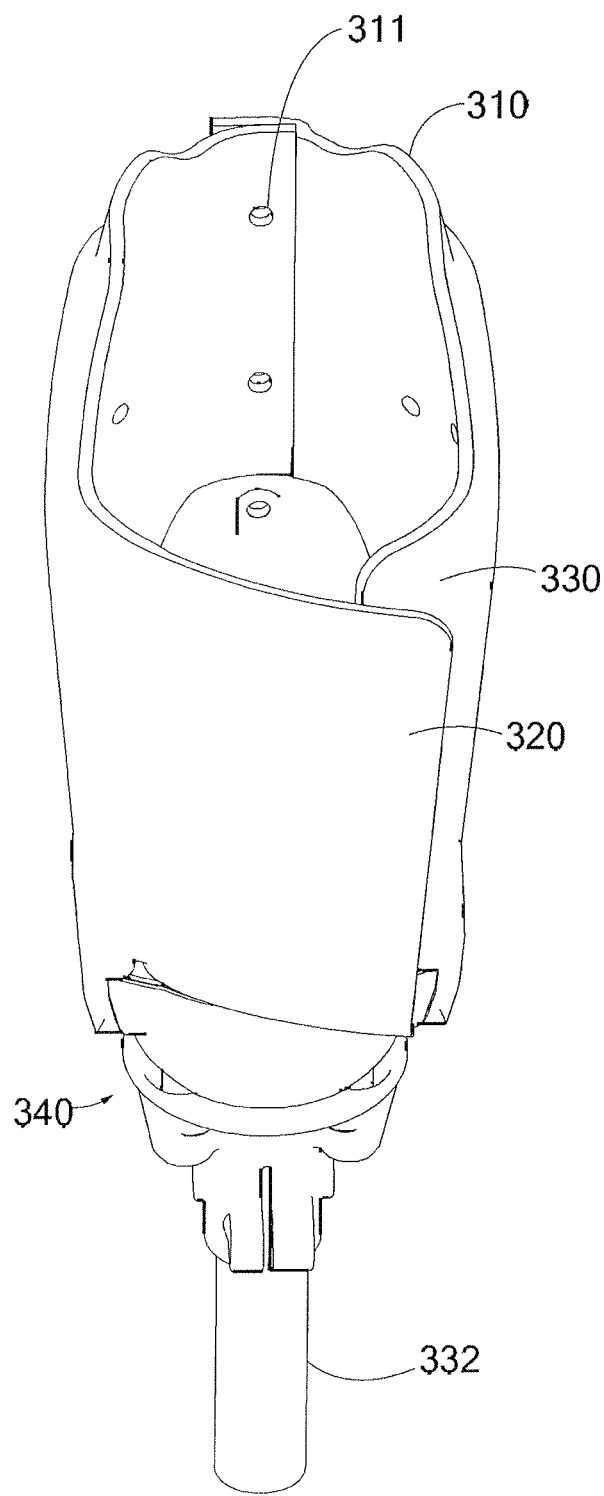
FIG. 26A illustrates a perspective view of an exemplary embodiment of an outer shell connected to a shank by a connector for use in an adjustable prosthesis system.
Figure 26B:
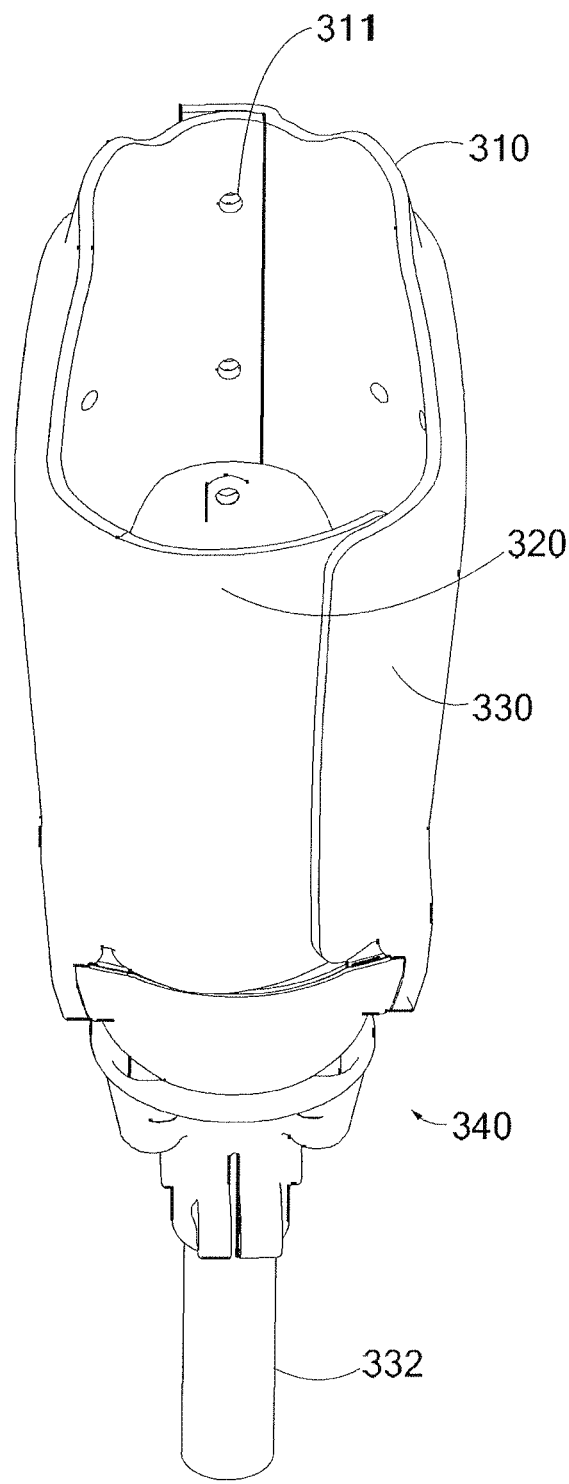
FIG. 26B illustrates a perspective view of another exemplary embodiment of an outer shell connected to a shank by a connector for use in an adjustable prosthesis system.
Figure 27B:
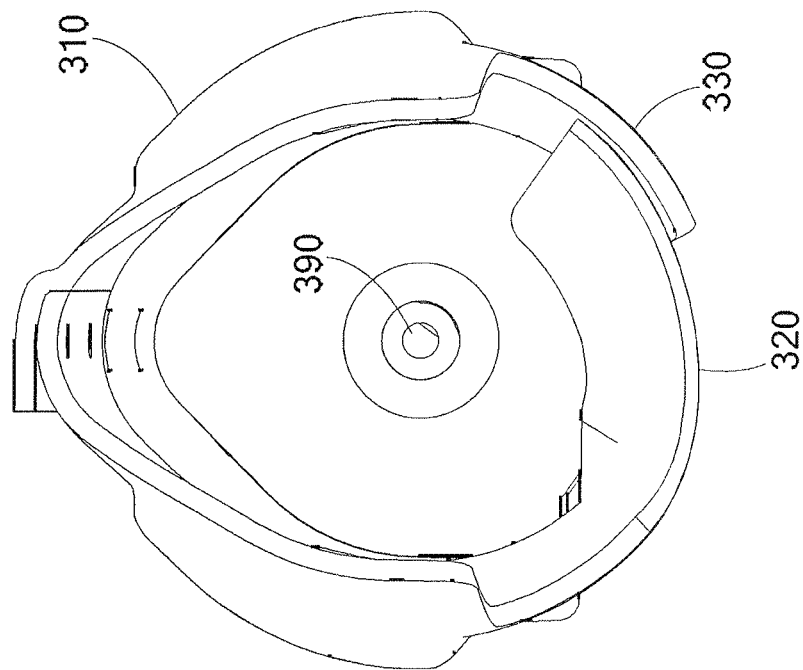
FIG. 27B illustrates a perspective top view of the exemplary embodiment of the outer shell illustrated in FIG. 26B.
Figure 27A:
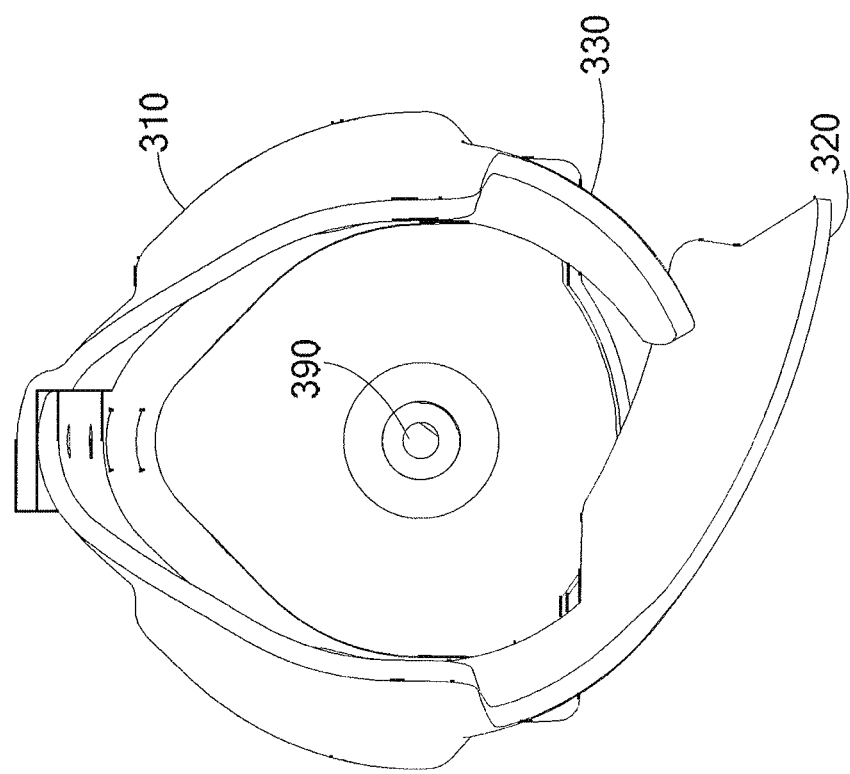
FIG. 27A illustrates a perspective top view of the exemplary embodiment of the outer shell illustrated in FIG. 26A.

The inner liner 378, which receives a residual limb, is inserted into the adjustable outer shell 310, which is primarily (substantially) constructed of a flexible material or a stiff material with flexible regions. In this embodiment, the outer shell 310 has two opposing, overlapping flaps 320, 330, as illustrated in FIGS. 26A, 26B, 27A and 27B. As shown in those figures, one flap 320 is longer than the other flap 330 in this exemplary embodiment. During use, the longer flap 320 may overlap the shorter flap 330, as illustrated in FIGS. 26A and 27A; or the shorter flap 330 may overlap the longer flap 320, as illustrated in FIGS. 26B and 27B. A closure component(s) (not shown) is used to hold the overlapping flaps 320, 330 in place and to tighten or loosen the adjustable outer shell 310 about the residual limb in the inner liner 378 positioned in the adjustable outer shell 310.

Optional stiffening components (not shown) may be included on the sides of outer shell 310. For example, long, narrow strips of metal or other material may be placed in a longitudinal position on the sides of the outer shell 310 shown in FIG. 26A or 26B. In one embodiment, the stiffening components may be molded in place in the flexible material of the outer shell 310. Selective stiffening parts (not shown) also may be encapsulated in the flexible material of the outer shell 310.

As shown in FIGS. 27A and 27B, a hole 390 for receiving the locking pin 386 is provided in the bottom of the adjustable outer shell 310.

Figure 28A:
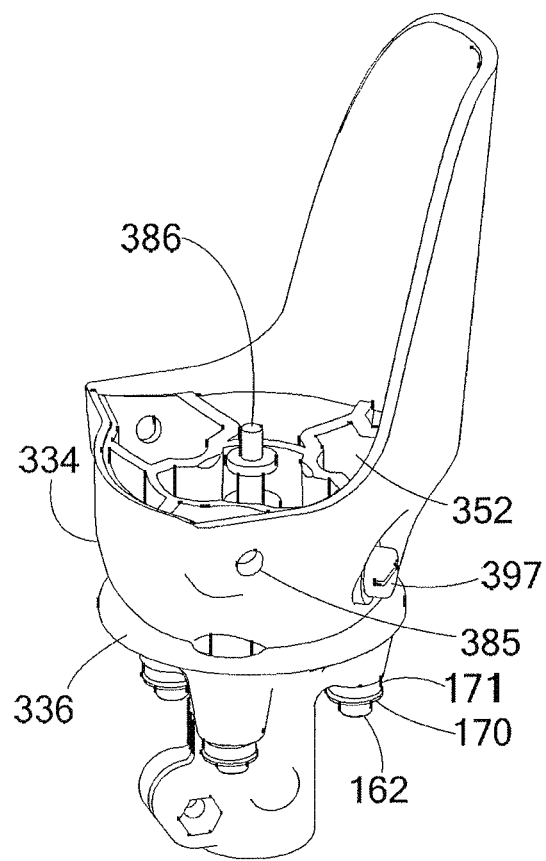
FIG. 28A illustrates a perspective view of an exemplary embodiment of a connector assembly for use in an adjustable prosthesis system.
Figure 28B:
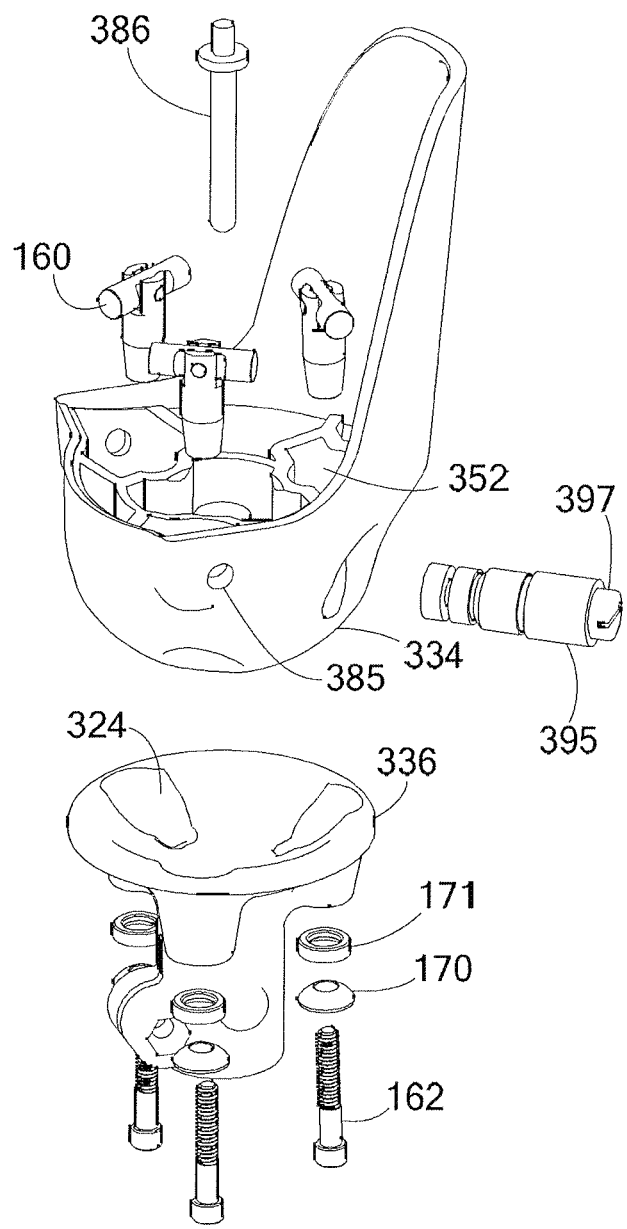
FIG. 28B illustrates a perspective exploded view of the exemplary embodiment of the connector assembly illustrated in FIG. 28A.
Figure 29:
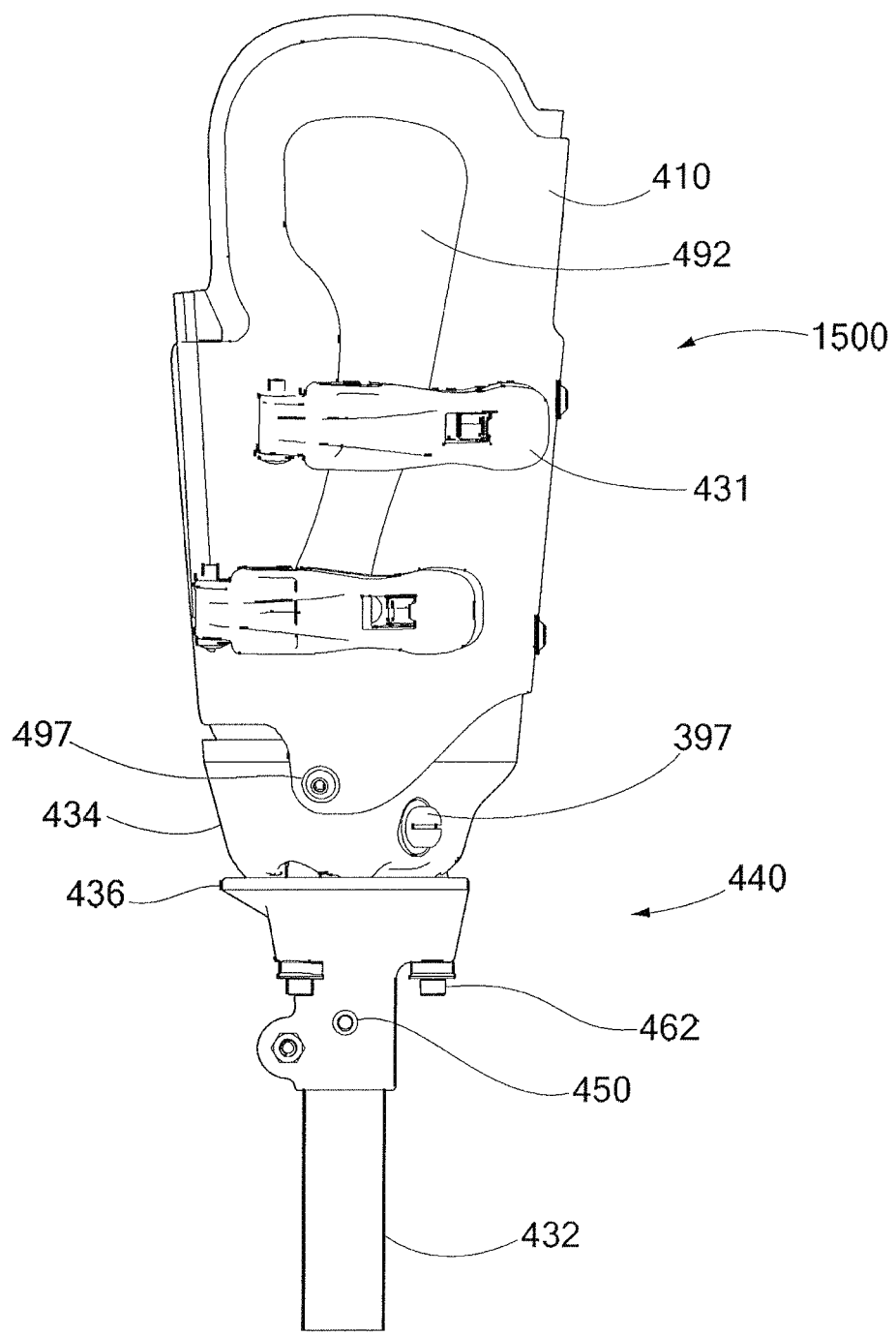
FIG. 29 illustrates a perspective view of an exemplary embodiment of a modular prosthetic device/prosthesis system.

FIG. 28A shows the connector assembly 340 used in this exemplary embodiment. An exploded view of the connector assembly 340, as shown in FIG. 28B, shows the various components of the connector assembly 340.

Figure 25:
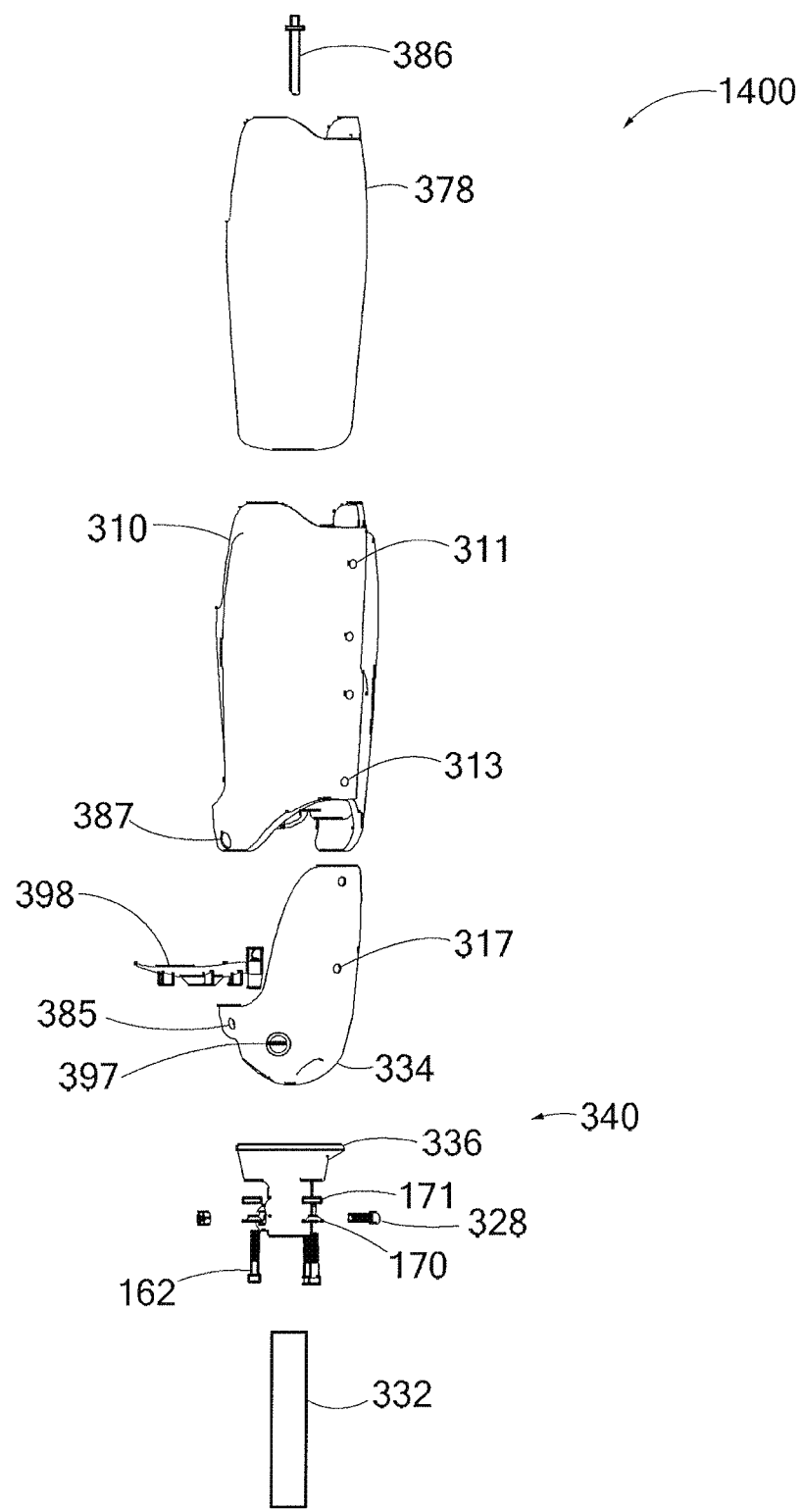
FIG. 25 is a slightly rotated view of the exemplary embodiment of the adjustable prosthesis system illustrated in FIG. 24.

The connector assembly 340 includes an upper plate 334 having a convex bottom surface and a lower plate 336 having a concave upper surface to receive the convex bottom surface of the upper plate. The upper plate 334 is connected to the outer shell 310 by a fastener(s) (not shown) at apertures 385 and 387. In addition, as shown in FIG. 25, the two apertures 317 on the back of plate 334 are connected by fasteners (not shown) to the two lower apertures 313 on the back of outer shell 310. Fasteners (not shown) connect the two sides of the outer shell 310 at the two upper apertures 311.

Rocker bolt assemblies 160 fasten the upper plate 334 and the lower plate 336 in this exemplary embodiment. As previously discussed, FIGS. 19a and 19b illustrate the exemplary rocker bolt assembly 160 in more detail. As explained in that previous discussion, each rocker bolt assembly 160 receives a threaded bolt component 162 with convex collar washer 170 and concave funnel-shaped washer 171. Rocker bolt assemblies 160 rest in rocker bolt apertures 352 of the upper plate 334 and are unable to fall through rocker bolt apertures 352 because of the horizontal rod 169 (FIG. 19b).

Hollow threaded socket 164 projects into aperture 324 on the lower plate 336, allowing threaded hex bolt component 162 to tighten within hollow threaded socket 164. Convex collar washer 170 and concave funnel-shaped washer 171 are secured between hollow threaded socket 164 and threaded hex bolt 162.

In the exemplary embodiment illustrated in FIGS. 28A and 28B, there are three rocker bolt assemblies 160. In further exemplary embodiments, additional rocker bolt assemblies 160 may be used.

The locking pin 386 is guided into the bottom of the adjustable outer shell 310 and into the hole 390 (see FIGS. 27A and 27B) where it engages the locking mechanism 395, which in the embodiment shown is a one-way clutch. The one-way clutch prevents the locking pin 386 from being pulled out (and prevents the residual limb from coming out also). The locking mechanism 395 is released by pushing on the button 397, which releases the locking pin 386. Persons skilled in the art will recognize that the locking mechanism 395 (one-way clutch) may be operated by means other than pushing a button 397, such as twisting a knob.

Figure 24:
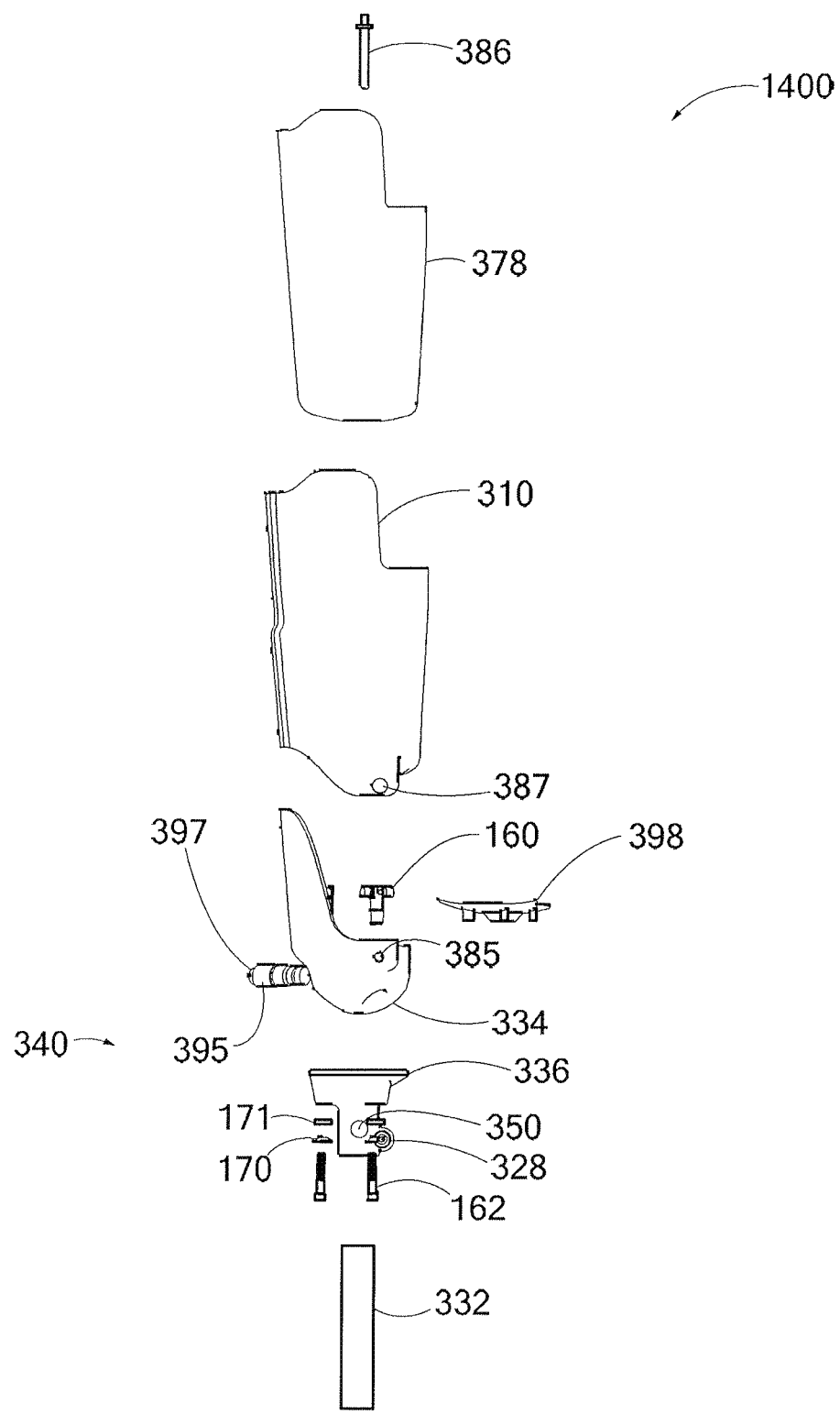
FIG. 24 illustrates a perspective exploded view of an exemplary embodiment of an adjustable prosthesis system.

As shown in FIGS. 24 and 25, a bottom plate 398 is positioned between the bottom of the outer shell 310 and the connector assembly 340 to accommodate the locking pin 386 suspension system and cover the rocker bolts 160.

As also shown in FIGS. 24 and 25, a fastener 328, such as a bolt and nut in the exemplary embodiment, is used to clamp the lower plate 336 of connector assembly 340 to the shank 332. Optional set screws (not shown) may be inserted in aperture 350 and an other aperture (not shown) on the opposite side of plate 336 to be used to adjust the positioning of the shank 332.

Another exemplary embodiment of Applicant's adjustable prostheses system 1500 is illustrated in FIGS. 29-34. The system includes an outer shell 410, one or more buckles 431, and an adjustable connector assembly 440, which connects the adjustable outer shell 410 to shank 432 or another prosthetic device. The system also may include a locking pin (not shown), such as the locking pin (386) illustrated in FIGS. 28A and 28B, which is released by pushing on button 397.

Figure 30:
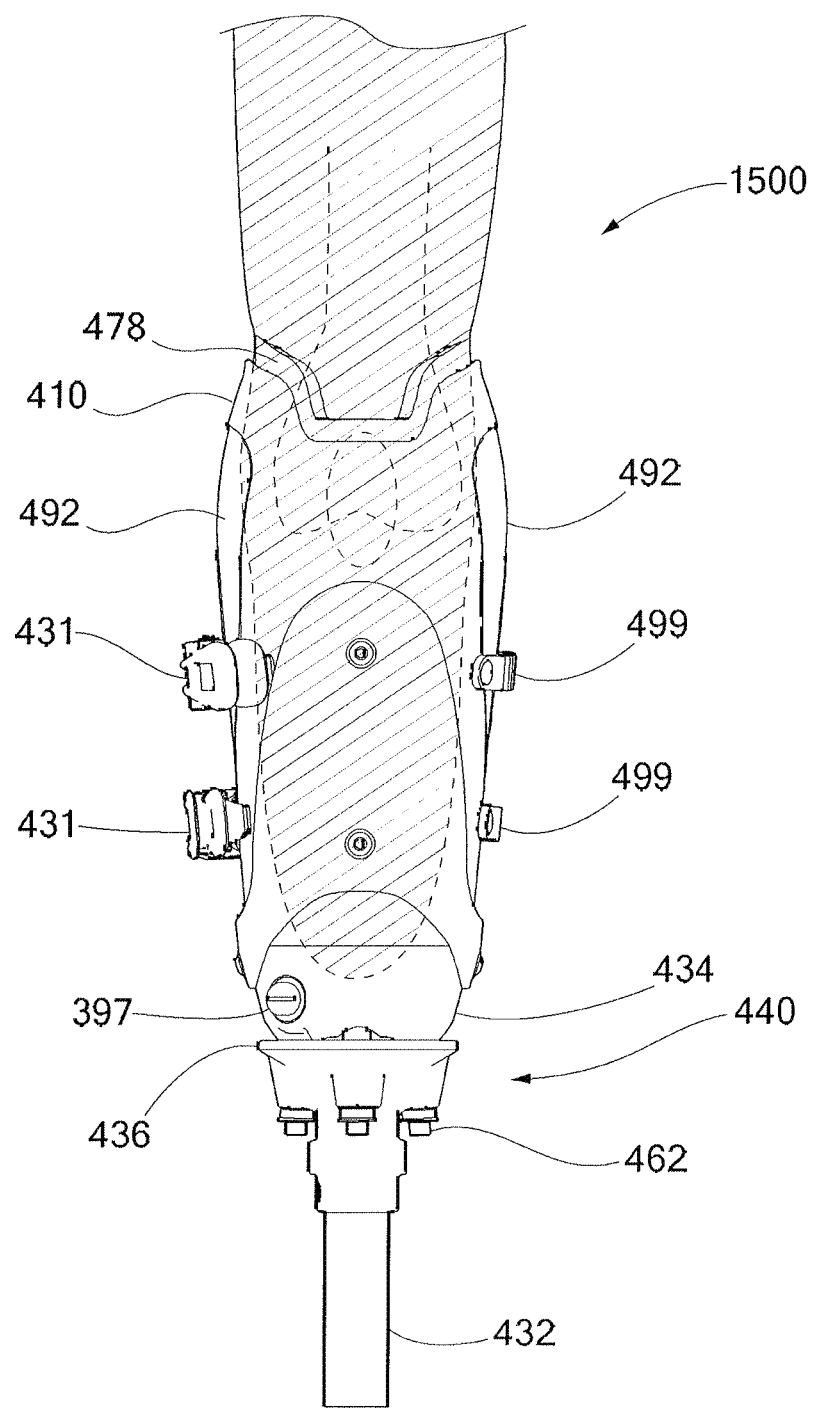
FIG. 30 illustrates a perspective view of an exemplary embodiment of a modular prosthetic device/prosthesis system on a residual limb.

The inner liner 478, which receives a residual limb, is inserted into the adjustable outer shell 410, as shown in FIG. 30. The outer shell 410 is primarily (substantially) constructed of a flexible material or a stiff material with flexible regions.

Figure 34:
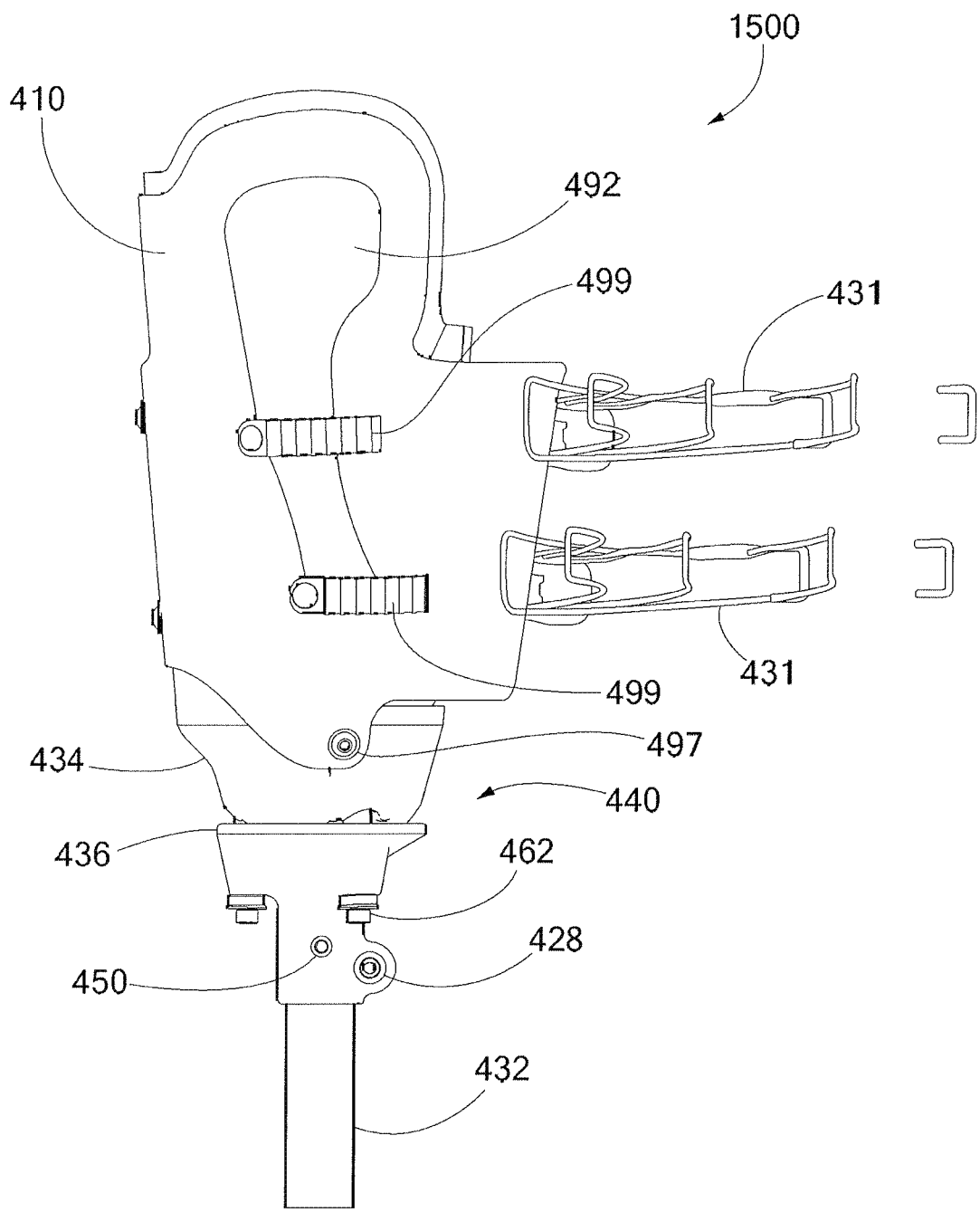
FIG. 34 illustrates a perspective view of an exemplary embodiment of a modular prosthetic device/prosthesis system.

Optional stiffening components 492 (FIG. 34) may be included on the sides of outer shell 410. For example, long, narrow strips of metal or other material may be placed in a longitudinal position on the sides of the outer shell 410, as shown in FIG. 34. In one embodiment, the stiffening components 492 may be molded in place in the flexible material of the outer shell 410. Selective stiffening parts (not shown) also may be encapsulated in the flexible material of the outer shell 410, or may be attached externally or internally to the outer shell 410 by various means.

The connector assembly 440 includes an upper plate 434 and a lower plate 436. The upper plate 434 is connected to the outer shell 410 by fasteners 497. The upper plate 434 and the lower plate 436 are connected by fasteners 462. In one embodiment, fasteners 462 are part of a rocker bolt assembly (not shown), such as the rocker bolt assembly illustrated in FIGS. 28A and 28B.

As shown in the exemplary embodiment illustrated in FIG. 30, the inner liner 478 extends over the knee (shown in phantom) on the medial and lateral sides (inside and outside of the knee). The buckles 431 compress the rigid stiffening components 492, which extend above the knee, providing a rigid force transfer to firmly grasp the knee. This grasp on the knee allows for knee flexion and extension yet limits medial and lateral movement, and provides both a solid, highly functional grasp of the knee and stability of gait.

In FIG. 30 the extent of the inner liner 478 can be seen in a frontal view of the adjustable prosthesis system 1500. In this view, the residual limb is shown in phantom relative to the inner liner 478 and outer shell 410, which view illustrates how the walls of the inner liner 478 and the outer shell 410 extend over the knee. The combination of the material properties of the inner liner 478, flexible outer shell 410, and rigid stiffening components 492 allows for the grasping of the residual limb. In one embodiment, force for the grasping is provided by the use of a system including buckle 431 and hook mechanism 499, such as illustrated in FIG. 34 and discussed below.

This type of adjustable prosthesis system 1500 is a supra-condylar system. Such a system is able to suspend the prosthesis on the residual limb. In addition, the system can stabilize the valgus and the varus stresses on the residual limb and knee.

Figure 32:
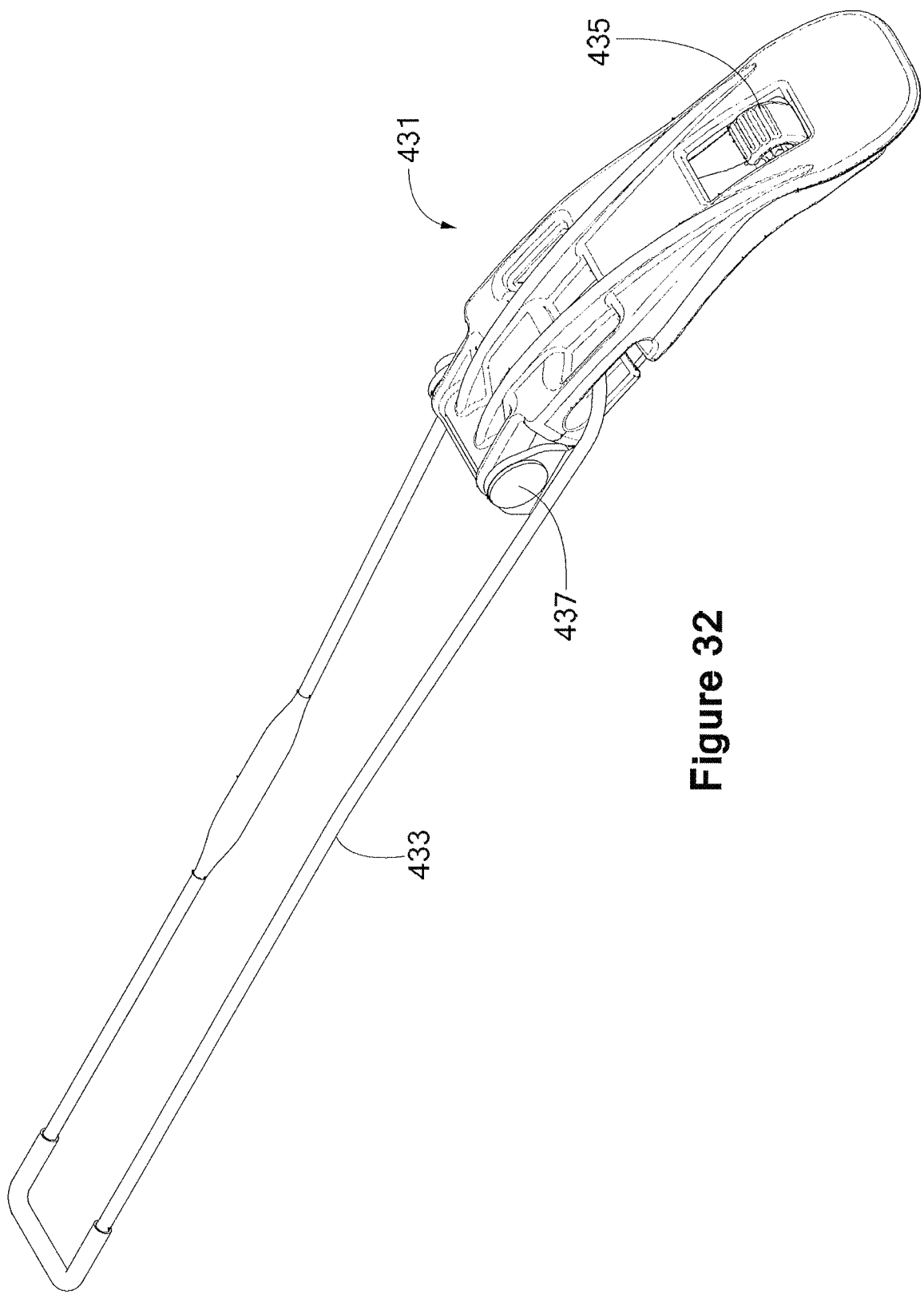
FIG. 32 illustrates another perspective view of the buckle and the cable shown in FIGS. 31A and 31B.

FIGS. 31-33 illustrate the closure components for one exemplary embodiment, which components include buckle(s) 431 and cable 433. Current commercially available buckles do not generate sufficient force without hand discomfort. For this reason, buckle 431 has been designed with a much higher mechanical advantage. The buckle 431 pulls the cable 433 over-center to latch the buckle and secure it.

Buckle 431 has a locking mechanism 435 to keep the buckle closed and prevent accidental opening. This safety latch, locking mechanism 435, makes it much less likely that outer shell 410 will accidentally open and put a patient at risk for a fall. The locking mechanism 435 requires two motions—one to push the locking mechanism 435 out of the way, and one to pull the buckle 431 away from the outer shell 410.

A slit 439 in the undersurface of the buckle 431 allows the user to switch sizes of cable 433 to most optimally fit around the outer shell 410 (and a residual limb in inner liner 478 inside outer shell 410).

FIGS. 31A and 31B show the buckle 431 in the open position, while FIG. 32 shows the buckle 431 in a closed position. The opening and closing of buckle 431 occurs when the upper part of buckle 431 rotates or pivots around pin 437.

Figure 33A:
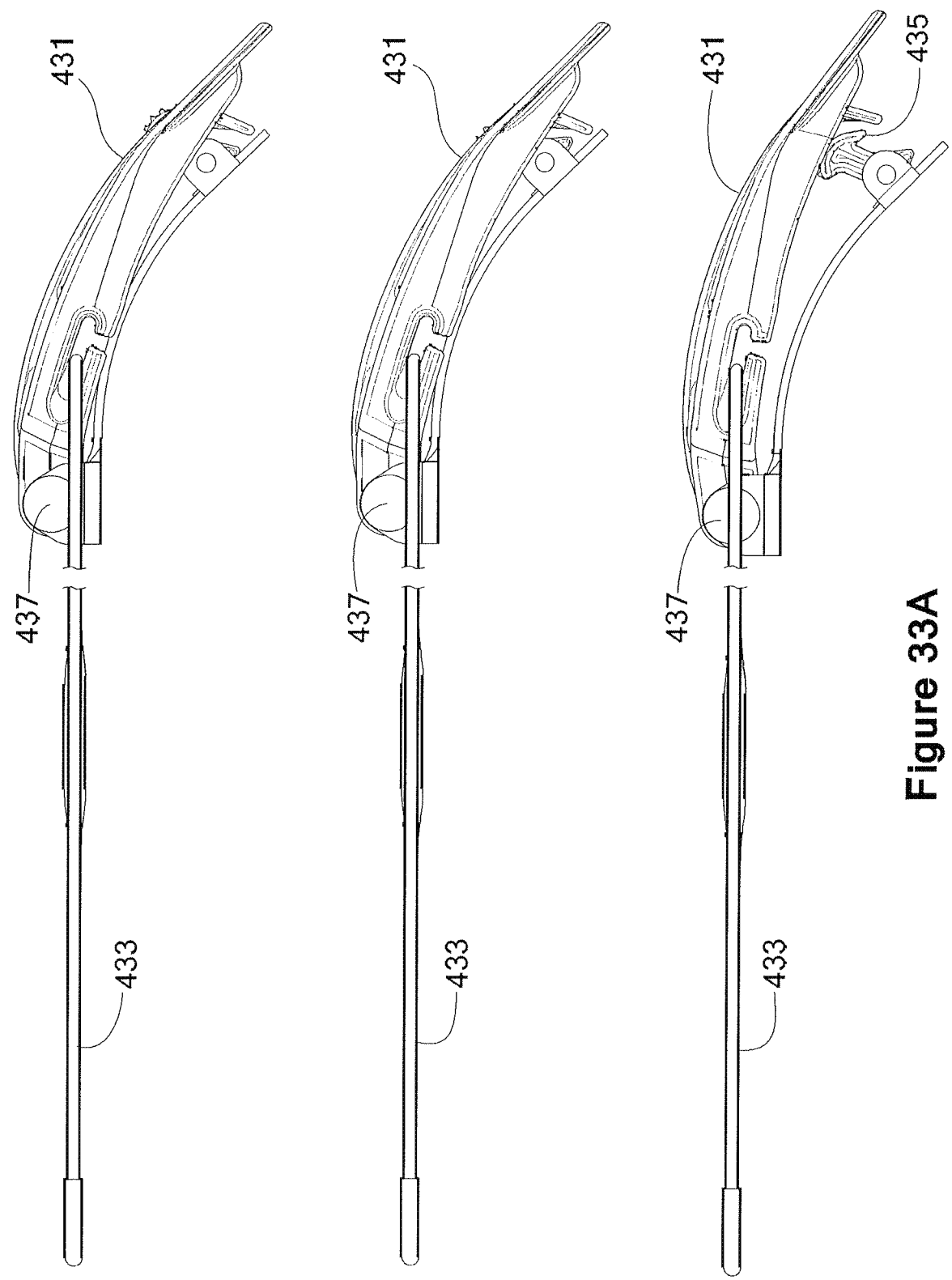
FIG. 33A illustrates a series of perspective views of different positions of the buckle and the cable shown in FIGS. 31A, 31B, and 32.
Figure 33B:
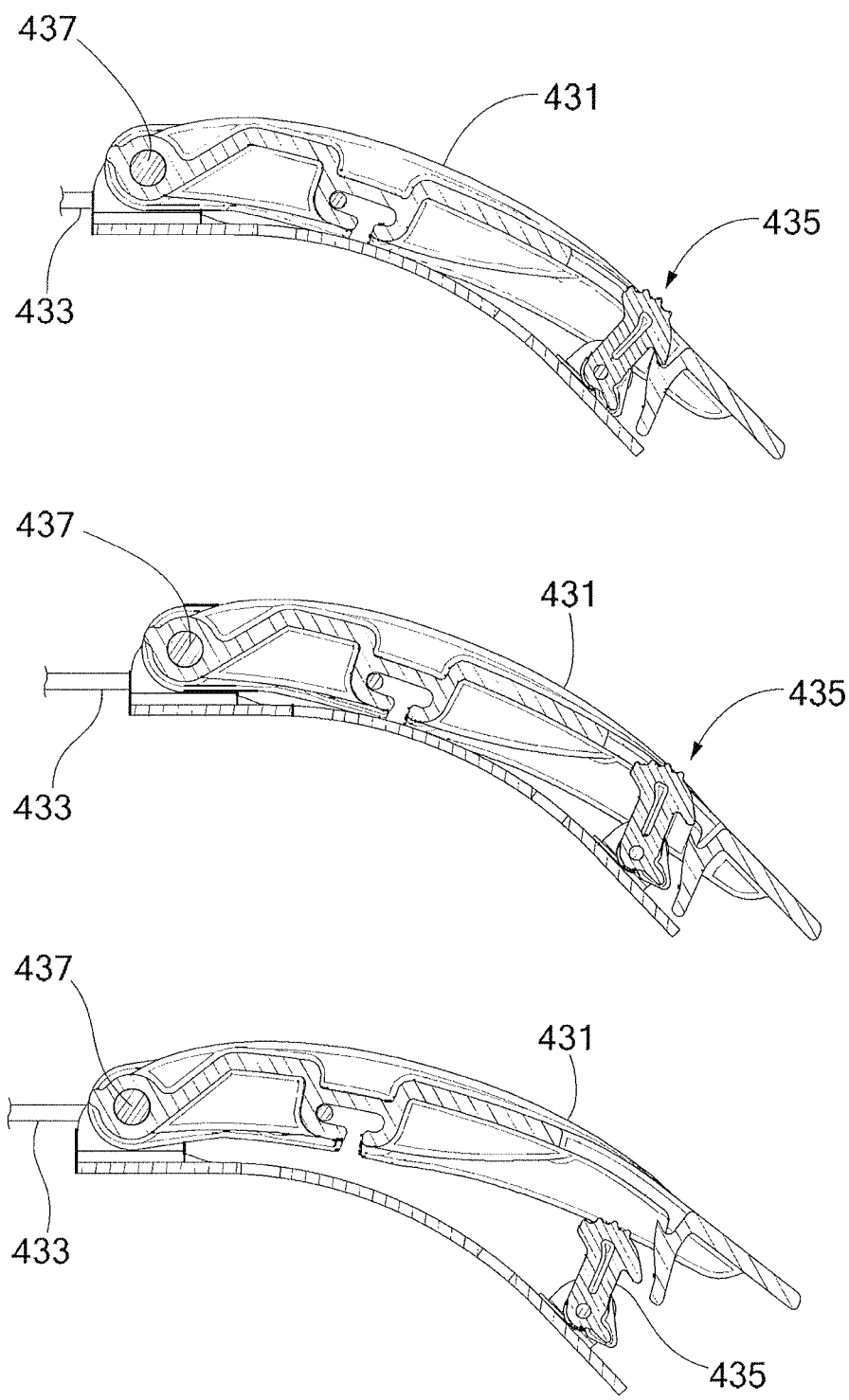
FIG. 33B illustrates another series of perspective views of different positions of the buckle and the cable shown in FIGS. 31A, 31B, and 32.

The series of the three positions of buckle 431 in FIG. 33A shows the opening of the buckle from an external perspective. The opening of buckle 431 from an internal perspective is illustrated by the series of three positions of the buckle in FIG. 33B.

The exemplary embodiment of Applicant's adjustable prosthesis system 1500 illustrated in FIG. 34 shows the hook mechanism 499 opposite the buckles 431 that allow the cable 433 to hook itself and provide a firm base of support for the buckle 431 to close the outer shell 410 and inner liner 478 around the residual limb. The hook mechanism 499 has multiple slots that allow fine adjustments for adjusting how much the buckle and cable system closes the outer shell 410.

Knurling of the shank 432 is done at the end that inserts into adjustable connector assembly 440. This knurling process is where a series of surface deformations (not shown) of the metal shank 432 are made to increase friction when the shank 432 is inserted into the adjustable connector assembly 440. The opening is made smaller by means of a closure bolt 438. The surface deformations or indentations may be straight, angled, diamond shaped, or other shapes as will be recognized by persons of skill in the art. A set screw 450 further indents and grasps the shank 432. Other mechanisms such as, but not limited to, carbon paste to increase friction between the connector and the metal shank 432 can be used.

The lower plate 436 of adjustable connector assembly 440, although adapted for attachment to a metal circular shank 432—a common means in the industry of connecting a prosthesis to a prosthetic feet, could also be modified from its present form. Instead of a receptor for a shank 432, it could be made with the bottom surface containing a rectangular pyramid or other specific pieces that allow it to attach to other commercially available feet and ankle mechanisms.

Another exemplary embodiment of Applicant's adjustable prosthesis system 1600 is illustrated in FIGS. 35 and 36A-36C. The system includes an outer shell 510, one or more closure components 599/531, an inner liner (not shown) and an adjustable connector assembly 540, which connects the adjustable outer shell 510 to a shank (not shown) or another prosthetic device.

Figure 35:
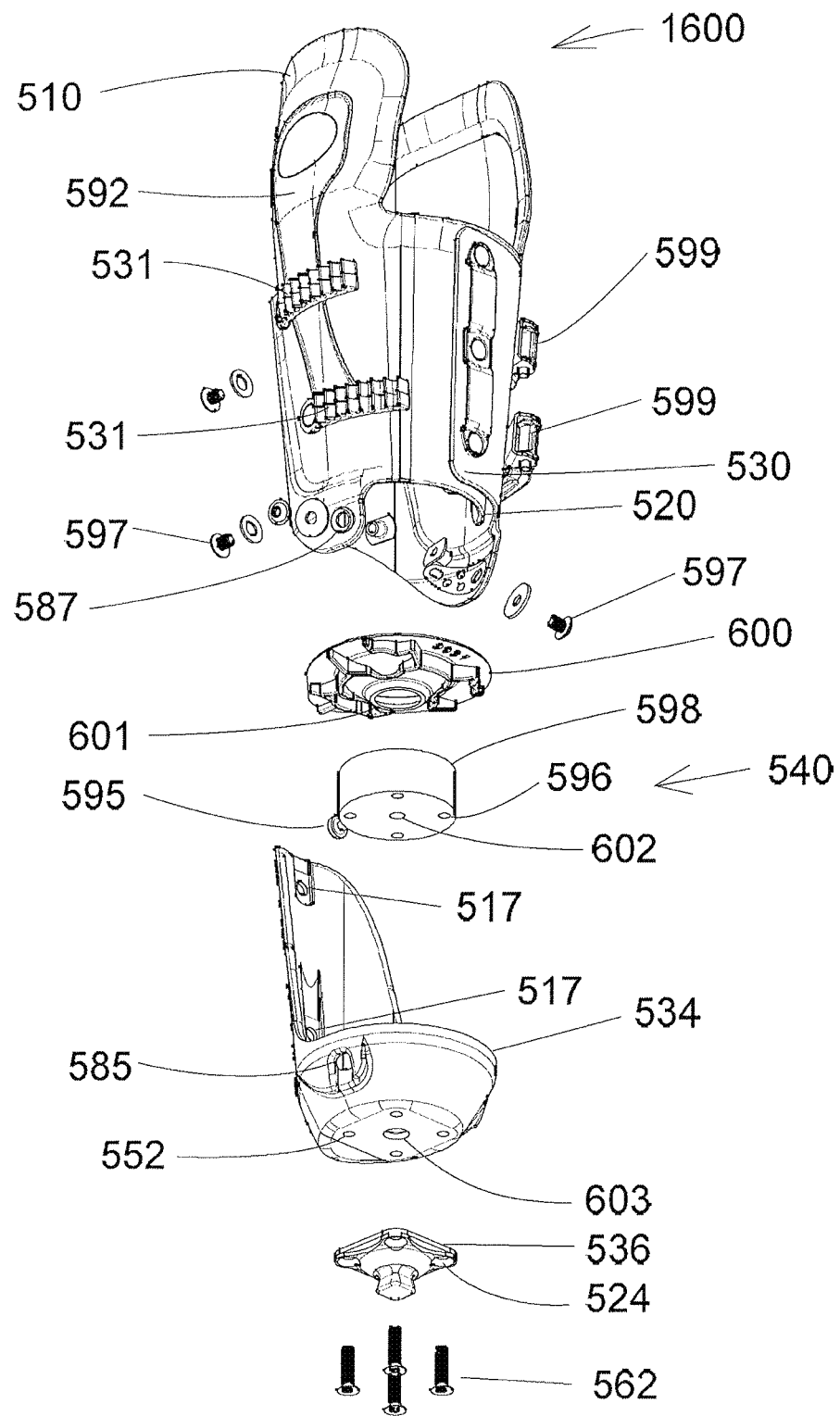
FIG. 35 illustrates a perspective exploded view of another exemplary embodiment of an adjustable prosthesis system without rocker bolts, using for example a pyramid connector.
Figure 37B:
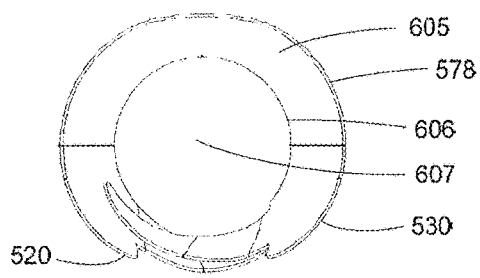
FIG. 37B illustrates a top view of an exemplary embodiment of a deformable inner liner for a modular prosthesis system.
Figure 38:
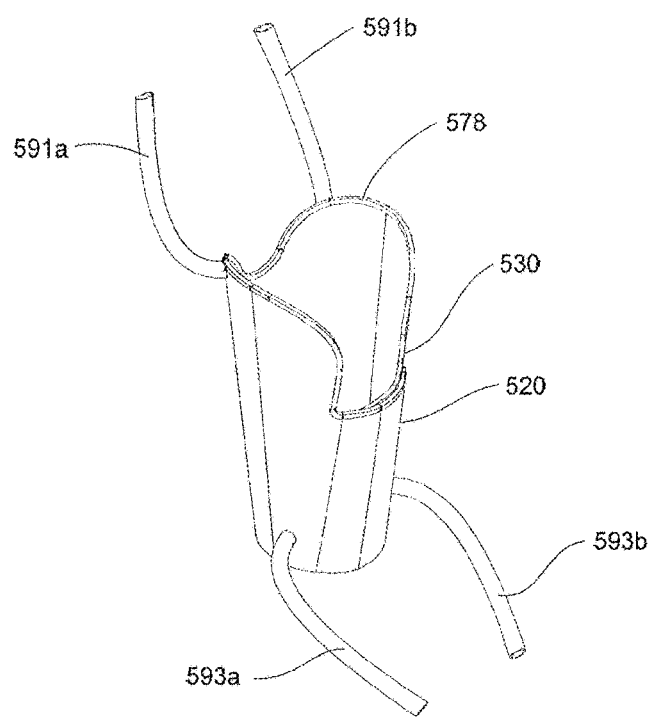
FIG. 38 illustrates a perspective view of an exemplary embodiment of a deformable inner liner for a modular prosthesis system including inlet tubes and outlet tubes for injecting and removing liquid foam or other material into and from an annular cavity within the deformable inner liner.
Figure 37A:
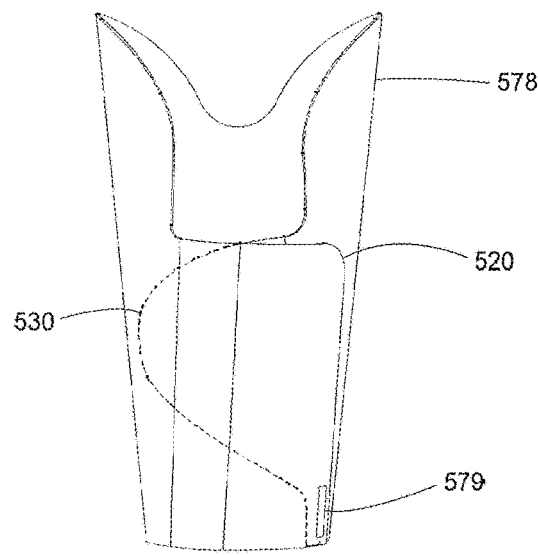
FIG. 37A illustrates a front view of an exemplary embodiment of a deformable inner liner for a modular prosthesis system.

As shown in FIGS. 37A, 37B, and 38, a deformable inner liner 578, which receives a residual limb, is inserted into the adjustable outer shell 510, which is primarily (substantially) constructed of a flexible material or a stiff material with flexible regions. In this embodiment, the outer shell 510 has two opposing, overlapping flaps 520, 530, as illustrated in FIG. 35. As shown in that figure, one flap 530 is longer than the other flap 520 in this exemplary embodiment. During use, the longer flap 530 overlaps the shorter flap 520, as illustrated in FIG. 35. A closure component(s) 599 is used to hold the overlapping flaps 520, 530 in place and to tighten or loosen the adjustable outer shell 510 above the residual limb and the deformable inner liner 578 positioned in the adjustable outer shell 510.

Optional stiffening components 592 may be included on the sides of outer shell 510. For example, long, narrow strips of metal or other material may be placed in a longitudinal position on the sides of the outer shell 510 shown in FIGS. 35, 36A, and 36B. In one embodiment, the stiffening components may be molded in place in the flexible material of the outer shell 510. Selective stiffening parts (not shown) also may be encapsulated in the flexible material of the outer shell 510.

Referring to FIG. 35, the adjustable connector assembly 540 includes a cup 534 and a pyramid connector 536. The cup 534 is connected to the outer shell 510 by fasteners 512 at apertures 517 on the back of the cup 534 and corresponding apertures (not shown) on the back of outer shell 510. Fasteners 597 connect the two sides of the outer shell 510 at the two apertures 587 of the outer shell 510 and the apertures 585 of the cup 534. The washers shown in connection with fasteners 597 may be optionally included.

The connector assembly 540 includes a clutch 598 into which a suspension pin (not shown) inserts from above. The clutch is connected to pyramid connector 536 by means of bolts 562 which pass through apertures 524 in the pyramid connector 536 and apertures 552 in the bottom of cup 534 and into apertures 596 of the clutch 598, thereby sandwiching the cup 534 between the clutch 598 and the pyramid connector 536.

The locking pin (not shown) is guided into the bottom of the adjustable outer shell 510 and into the aperture 601 of base plate 600, through aperture 602 of the clutch 598, and through aperture 603 of the cup 534 to an aperture (not shown) in pyramid connector 536. Base plate 600 prevents the residual limb from going down too far. The locking pin (not shown) is engaged by clutch 598, which prevents the locking pin from being pulled out (and prevents the residual limb from coming out also). The clutch 598 is released by pushing on the button 595, which releases the locking pin (not shown). Persons skilled in the art will recognize that the clutch 598 may be operated by means other than pushing a button 595, such as by twisting a knob.

A deformable inner liner 578 shown in FIG. 37A, which receives a residual limb, is inserted into the adjustable outer shell 510, in a manner similar to that shown in the embodiment illustrated in FIG. 30. The outer shell 510 is primarily (substantially) constructed of a flexible material or a stiff material with flexible regions.

FIG. 38 illustrates a deformable inner liner 578 equipped with inlet tubes 591a, 591b and outlet tubes 593a, 593b. The inlet tubes are used to inject liquid foam, or a comparable material, under pressure into the annular cavity 605 formed between flap 520 and flap 530, as shown in FIG. 37B. As shown in FIG. 34A, flaps 520 and 530 are connected by stitching 579. The liquid foam, or other material, injected through the inlet tubes 591a, 591b into the annular cavity 605 flows downward and exits the annular cavity 605 through the outlet tubes 593a, 593b. The injected foam (or other material) forms a solid material that takes a relatively short time to harden into a final shape around a residual limb using the process described below.

First, the patient's residual limb is inserted inside the deformable inner liner 578, which is then inserted inside the outer shell 510, or may already be inside and attached to the outer shell. The closure components 599 are buckled around the outer shell 510. Next, the rapidly forming liquid foam material is mixed and inserted into the annular cavity 605 of the deformable inner liner 578 via the inlet tubes 591a and 591b. The inner wall 606 of the deformable inner liner 578 is forced by the liquid foam (or other injected material) inward toward the inner cavity 607 around the residual limb and takes a shape that conforms closely to the shape of the residual limb. Next, any excess foam exits through the outlet tubes 593a and 593b, while the hardened foam in annular cavity 605 forms a customized shape that conforms to the shape of the residual limb. The removable inlet tubes 591a and 591b, as well as the removable outlet tubes 593a and 593b, are easily pulled from annular cavity 605 with relatively little force. This process leaves a final customized inner liner 578 that substantially provides for total contact and support for the various contours of the residual limb.

The custom fit inner liner 578 of this embodiment is a significant improvement over the prior art for the proper support of a patient's residual limb to control the prosthesis during walking by the patient. Such a customized inner liner 578 eliminates or minimizes pain with walking, helps prevent edema and skin breakdown, and reduces pressure over tender, bony prominences.

Figures 36A, 36B, 36C:
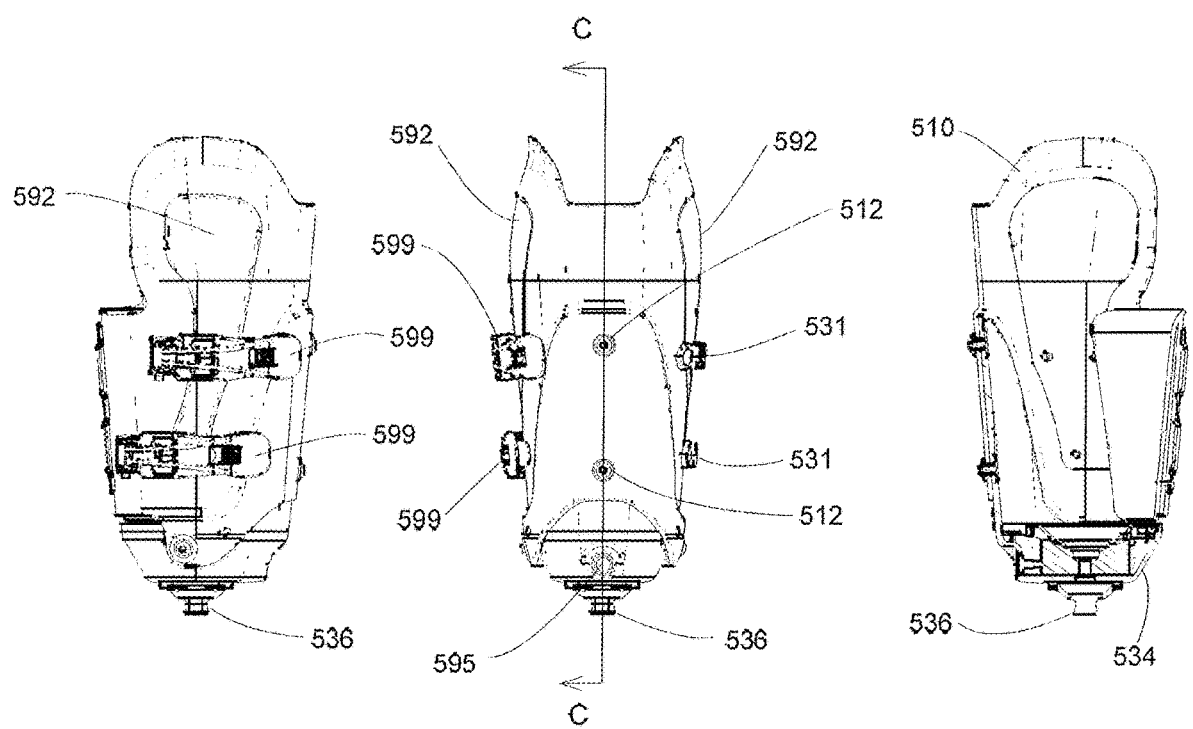
FIG. 36A illustrates a perspective side view of an exemplary embodiment of an outer shell with a pyramid connector and closure components for use in an adjustable prosthesis system.
FIG. 36B illustrates a perspective front view of an exemplary embodiment of an outer shell with a pyramid connector and closure components for use in an adjustable prosthesis system.
FIG. 36C illustrates a sectional view of an exemplary embodiment of the device shown in FIG. 36B.

Although the deformable inner liner 578 illustrated in FIGS. 37A and 37B, and the process for preparing a customized fitting inner liner 578 discussed above are described here for use with the embodiment illustrated in FIGS. 35 and 36A-36B, persons skilled in the art will recognize that inner liner 578 and the process for forming an inner liner 578 with a customized fit may be used in connection with other prosthetic devices and prosthesis systems, including, but not limited to, those disclosed throughout Applicant's present application and earlier related applications, including, but not limited to, the embodiments illustrated in FIGS. 1-34 attached to the present application.

Figure 39:
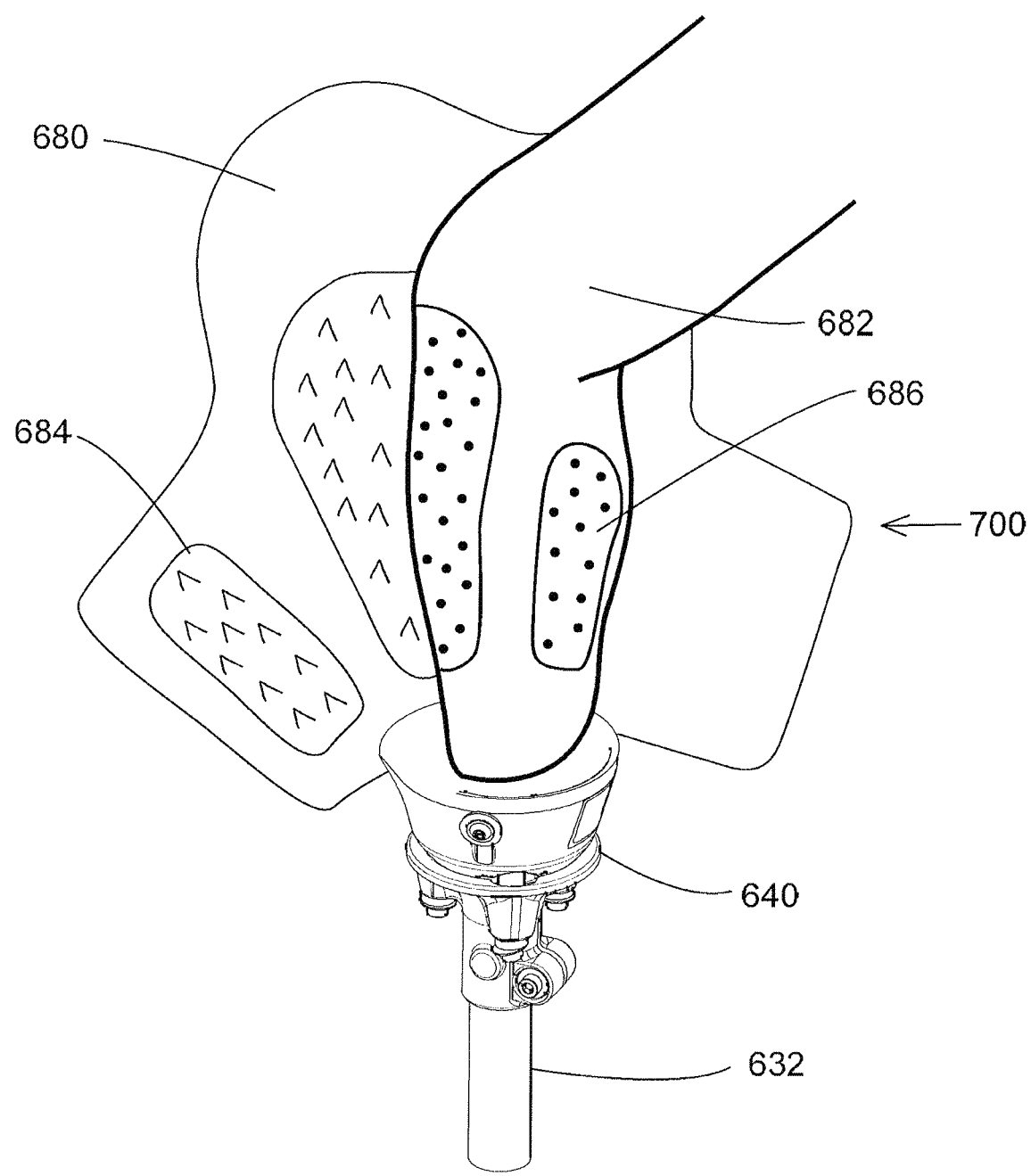
FIG. 39 illustrates a perspective view of an exemplary embodiment of a suspension system for a modular prosthesis system that uses material friction to provide a suspension of the device onto the limb.

FIG. 39 illustrates a friction suspension system 700, which also may be used with the prosthetic devices and prosthesis systems referred to in the above paragraph. Such a prosthesis system may include a shank 632 or another prosthetic device connected to an adjustable connector assembly 640 that connects to an adjustable prosthesis system, such as that illustrated in FIG. 35, for the residual limb of a patient.

In the embodiment of Applicant's adjustable prosthesis system illustrated in FIG. 35, as well as other embodiments of Applicant's adjustable prosthesis system discussed earlier, the patient's residual limb is received by an inner liner (e.g., inner liner 578 shown in FIGS. 37A and 37B), which is inserted in an adjustable outer shell (e.g., outer shell 510 shown in FIG. 35).

When the friction suspension system 700 shown in FIG. 39 is used, the adjustable prosthesis system is held on to the patient's residual limb by means of a flexible liner 680 (similar to inner liner 578 in FIGS. 37A and 37B). The inner side of the flexible liner has built in projections and patterns of raised elements that form a textured material 684. Those raised elements and projections are adapted to meet and mesh with corresponding built in projections and patterns of raised elements forming a textured material 686 on the outer side of a sleeve 682 that has been rolled onto the patient's residual limb.

When the flexible liner 680 is wrapped around the sleeve 682, the matching projections and patterns of raised elements on textured materials 684 and 686 form a bond that prevents removal of the residual limb and keeps the residual limb suspended when it is inserted into an inner liner (e.g., inner liner 578 shown in FIG. 37A) that is inserted into an adjustable outer shell (e.g., adjustable outer shell 510) in a manner similar to that shown in the embodiment illustrated in FIG. 30. The mechanical pressure placed on the flexible liner 680 when the adjustable outer shell (e.g., adjustable outer shell 510 in FIG. 35) is closed and held in place by closure component(s) (e.g., closure components 599 shown in FIGS. 36A and 36B) and the textured materials 684 and 686 help maintain a functional suspension of the prosthetic device or prosthesis system on the residual limb.

A further exemplary embodiment of the present invention relates to exemplary prosthetic devices that are useful for an amputation above the knee.

The use of prosthetic devices for above the knee amputation is known in the prosthetic arts. Shamp (U.S. Pat. No. 4,872,879) discloses an example of one such prosthetic device. In order to stay attached to the residual, and for purposes of providing support while in use, Shamp discloses that the containment recess of his prosthetic device is, as described in Shamp: "disposed to assure that the ischial tuberosity 33 and the associated ramus 34 (FIG. 8) of the ischium are contained within the open, proximal end 14 of the interface 11."

A drawing of the above arrangement may be illustrative.

Figure 40:
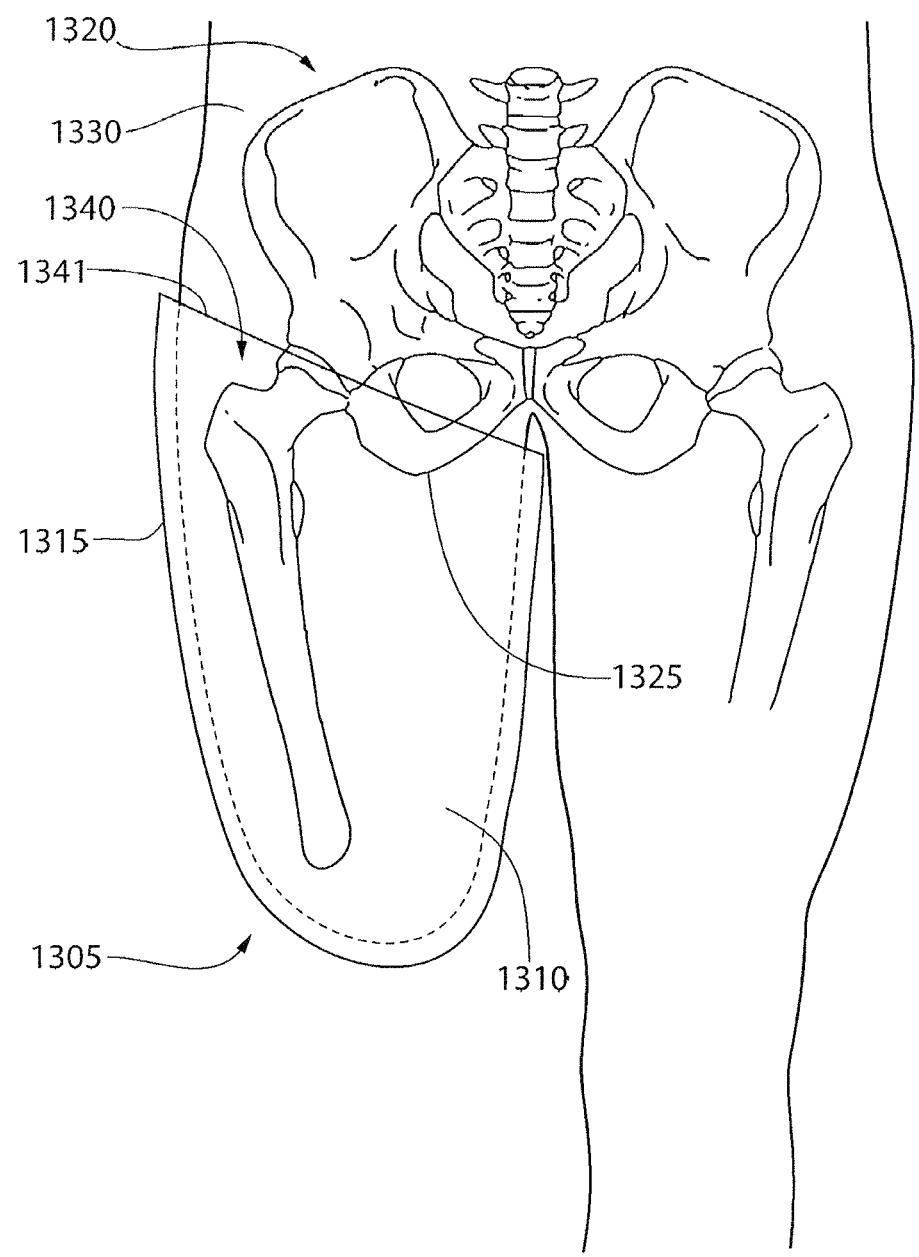
FIG. 40 is a line drawing of a prior art prosthetic system. This reflects ischial containment socket types.

FIG. 40 illustrates a prosthetic device similar to the one described by Shamp. The prior art device illustrated in FIG. 40 has been called in the literature: i) an ischial containment socket, ii) narrow ML (mediolateral), or iii) a CAT-CAM (contoured adducted trochanteric, controlled alignment method). The drawing is a front view line drawing of prosthetic device 1305 in use with a human body, and the location of various anatomical features are shown relative to the prosthetic device. Prosthetic device 1305 includes outer shell 1315 that surrounds residual limb 1310. Upper edge 1341 is below ilium 1330 of pelvis 1320. As shown, one of the pair of ischial tuberosities (or ischium) 1325 descends into prosthetic device 1305 via opening 1340 in the top of prosthetic device 1305. Put another way, a portion of ischium 1325 is below upper edge 1341 of prosthetic device 1305.

The prior art design shown in FIG. 40 suffers from a significant problem, because prosthetic device 1305 is uncomfortable to use when the patient is in the sitting position. In particular, when the patient is sitting, prosthetic device 1305 applies pressure to ischium 1325, which results in the patient feeling pain. Thus, the prosthetic device shown in FIG. 35 may be uncomfortable to wear.

Figure 41:
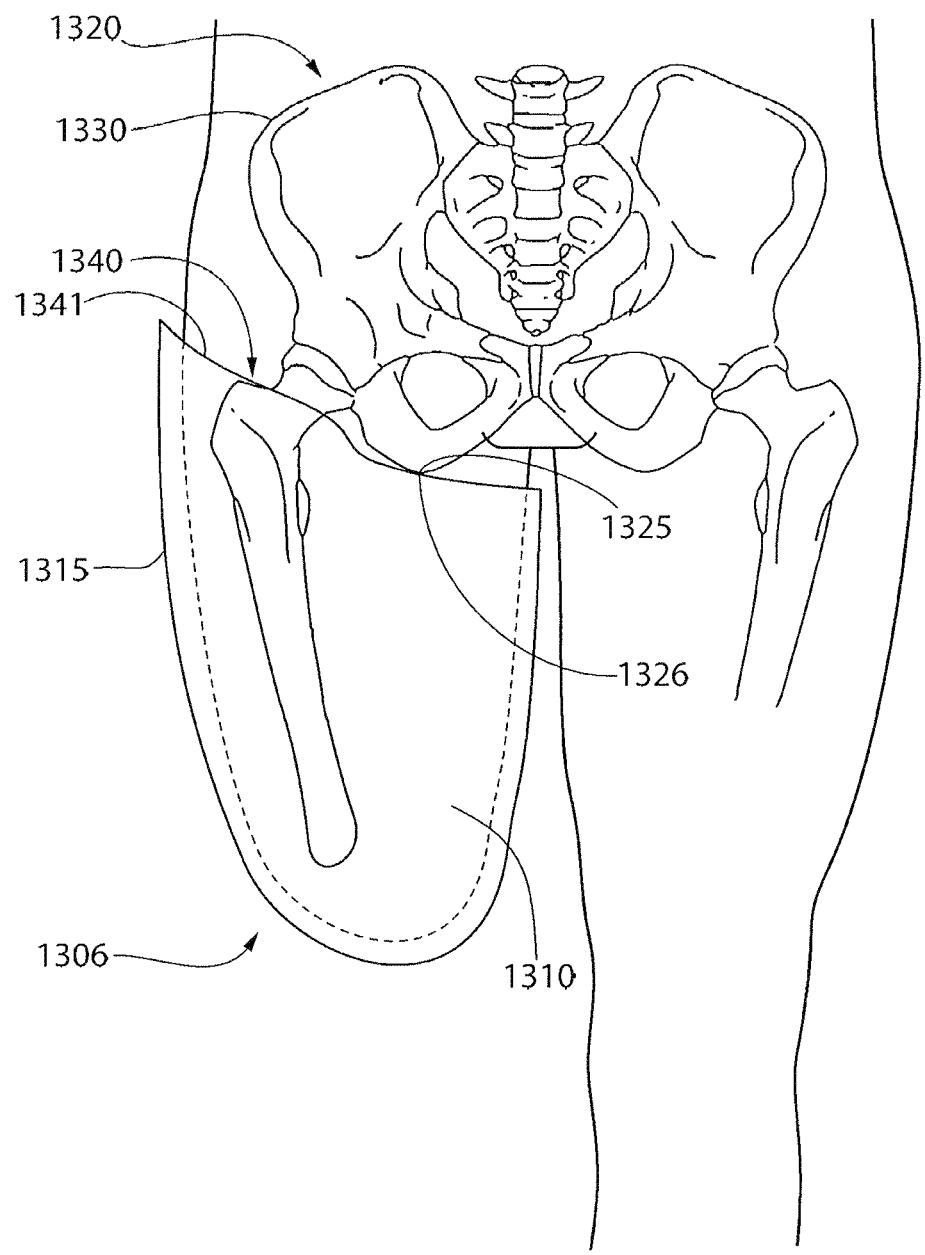
FIG. 41 is a line drawing of a further prior art prosthetic system. This reflects ischial weight bearing sockets such as the quadrilateral socket types

FIG. 41 is a front view line drawing that illustrates a further prosthetic device 1306 in the prior art. This prior art device is referred to as a quadrilateral or ischial weight bearing socket. Prosthetic device 1306 also includes outer shell 1315 that surrounds residual limb 1310, and the residual limb is inserted into prosthetic device 1306 via opening 1340. While upper edge 1341 is below illium 1330 and ischium 1325 of pelvis 1320, prosthetic device 1306 is positioned so that ischium 1325 sits on brim 1326. Thus, when the patient stands, brim 1326 applies direct pressure to ischium 1325 to provide load bearing during stance and gait. This direct pressure frequently causes the patient discomfort while sitting (due to the wide shelf or brim 1326 under he ischial tuberosity 1325). It also can cause pain during standing and walking as substantial body weight is borne through the ischium with this type of device. Prosthetic device 1306 shown in FIG. 41 may therefore be uncomfortable to wear.

Figure 42:
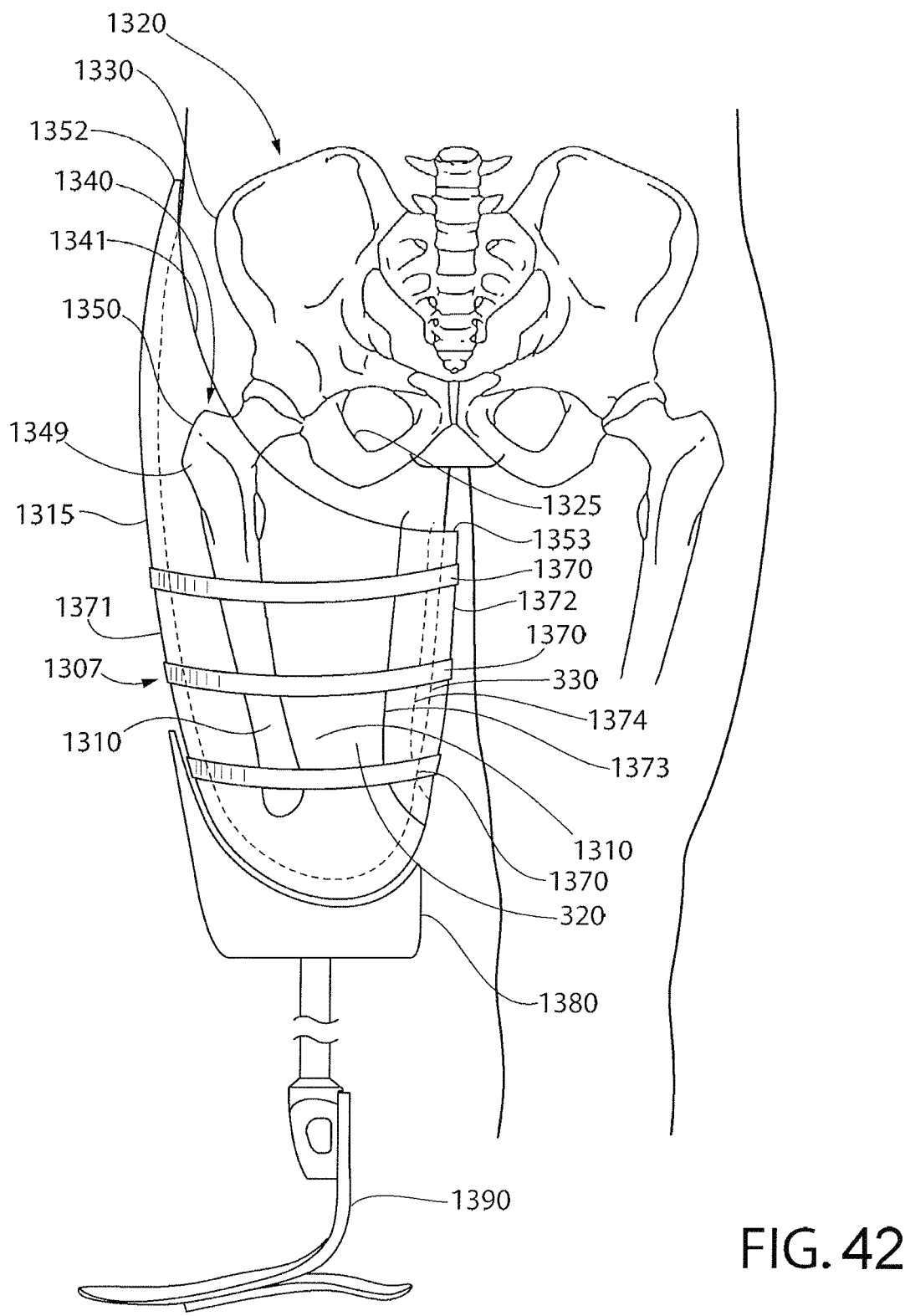
FIG. 42 is a line drawing of a prosthetic system in accordance with an exemplary embodiment of the present invention. This exemplary embodiment does not encompass or bear weight through the ischial bone.
Figure 43:
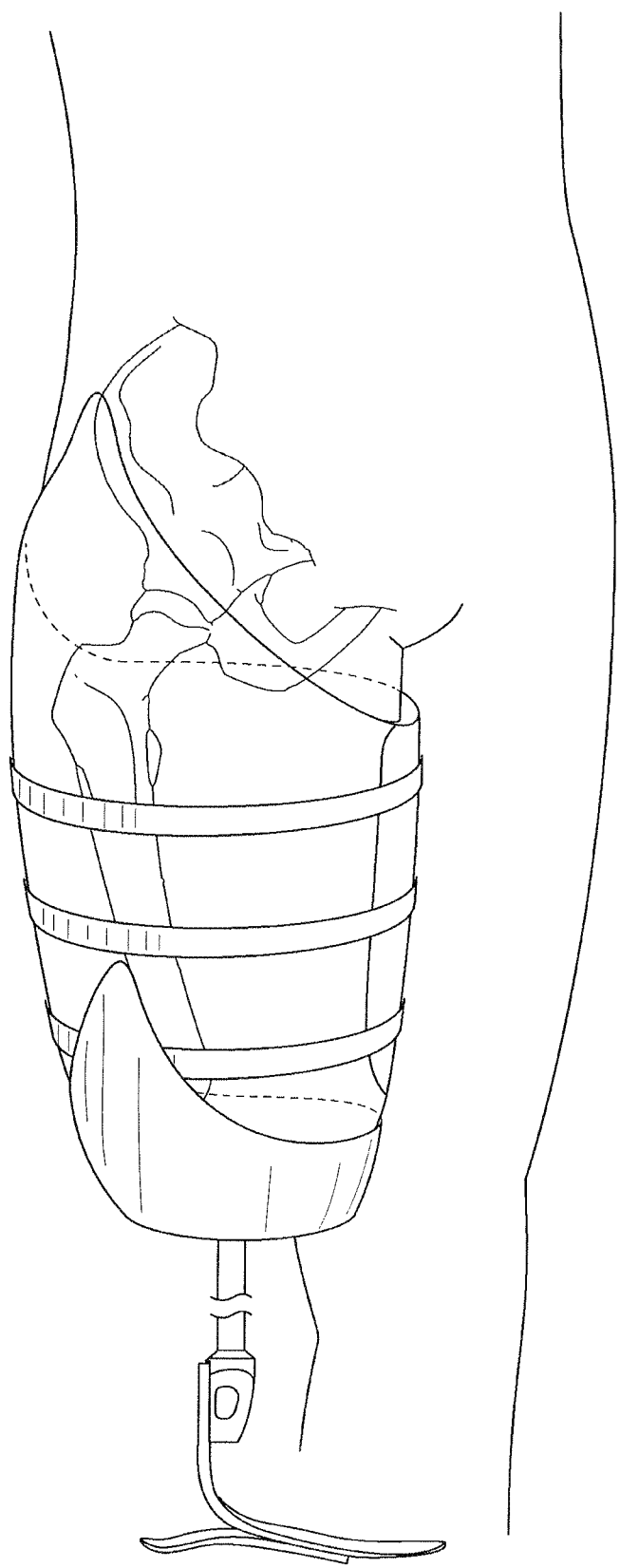
FIG. 43 is a perspective drawing of the prosthetic system illustrated in FIG. 42.

FIG. 42 is a front view line drawing that illustrates a further prosthetic device 1307 in accordance with an exemplary embodiment of the present invention. FIG. 43 is a perspective drawing of prosthetic device 1307 illustrated in FIG. 42. The exemplary embodiment illustrated in FIG. 42 and FIG. 43 will first be described by itself, following which, differences between the embodiment of FIGS. 42/43 and the prior art will be described.

Prosthetic device 1307 shares features included and described in other exemplary embodiments of the previously described above. Some of the features found in any of the above-described embodiments may also be found in prosthetic device 1307. Also, features from various embodiments may be combined and found within prosthetic device 1307.

Prosthetic device 1307 includes an outer shell 1315 that has features found in one or more of the exemplary embodiments of the present invention described above. For example, outer shell 1315 includes features similar to features found in socket 80 described above. Outer shell 1315 at least partially surrounds residual limb 1310. In one embodiment, outer shell 1315 partially surrounds residual limb 1310. In another embodiment, outer shell 1315 completely surrounds residual limb 1310.

In a further exemplary embodiment, outer shell 1315 includes a discontinuity in the form of flap 320 and flap 330. In FIG. 42, flap 320 extends from the left side of the drawing to the right side of the drawing and terminates at edge 1374. Flap 330 extends from the right side of the image towards the left side of the image and terminates at edge 1373. Because edge 1374 is behind flap 330 in FIG. 42, edge 1374 is shown in phantom.

Further views of flap 320 and flap 330 are shown in FIG. 26a and FIG. 26b. Flap 320 and flap 330 are described with reference to FIG. 26a and FIG. 26b. Flap 320 is able to slide relative to flap 330 and/or flap 330 is able to slide relative to flap 320.

Attachment devices 1370 are illustrated as an example of a mechanism for causing flap 320 and/or flap 330 to slide as described above. Tightening attachment devices 1370 thus changes the inner volume of prosthetic system 1307. Attachment devices 1370 may be straps, buckles, or some other type of mechanism which changes the fit of prosthetic system 1307 relative to residual limb 1310. Attachment devices 1370 may be similar to tightening components 84a, 84b described above. In one exemplary embodiment, attachment devices 1370 may be rigidly attached to prosthetic system 1307, for example to flap 320 and/or flap 330. In this manner, tightening of attachment devices 1370 causes flap 320 to move relative to flap 330 (and/or vice versa) in order to change the internal volume (and dimensions) of prosthetic system 1307. In this manner, prosthetic system 1307 may apply pressure to residual limb 1310.

Thus, as attachment devices 1370 are tightened, edge 1373 and/or edge 1374 move relative to each other. Once flaps 320 and 330 are overlapping, for example, further tightening of attachment devices 1370 causes edges 1373 and 1374 to move in opposite directions so that there is greater overlap between flap 320 and flap 330. In this manner, the internal volume of prosthetic system 1307 changes in order to change the fit of prosthetic system 1307 relative to residual limb 1310.

Outer shell 1315 includes outer side 1371 and inner side 1372 on opposite sides of residual limb 1310. Outer side 1371 and inner side 1372 may apply force to residual limb 1310 from opposite sides thereof. In a further exemplary embodiment, outer shell 1315 applies uniform force towards residual limb 1310 from about its circumference. Outer shell 1315 also includes upper most edge 1341 that defines opening 1340. Residual limb 1310 slides into prosthetic device 1307 by being inserted past upper edge 1341 and into opening 1340.

Prosthetic device is positioned relative to various bones in the patient's body. FIG. 42 illustrates several bones, namely pelvis 1320 that includes ischium 1325 and illium 1330. Also shown is femur 1349 and greater trochanter 1350.

In the exemplary embodiment shown in FIG. 42, an upper edge 1352 of the outer side 1371 is located above the greater trochanter, while the upper edge 1353 of the inner side 1372 is below ischium 1325 without being directly below ischium 1325. Also, in one embodiment, upper edge 1341 is not directly in-line with the bottom edge of ischium 1325. Rather, as shown in FIG. 37, there is a space as seen from the view of FIG. 37 between the bottom edge of ischium 1325 and upper most edge 1341.

Regarding the above language "below" and "directly below," if object A is directly below object B, then a line drawn directly downward from object B will intersect object A. if object A is below object B, then a line drawn directly downward from object B may or may not interest object A, however, object A appears lower than object B in the drawing.

In practice, prosthetic system 1307 is placed over (attached to) residual limb 1310 so that prosthetic system 1307 is situated relative to ilium 1330, greater trochanter 1350, and ischium 1325. Attachment members 1370 are then tightened to compress outer shell 1315 about residual limb 1310.

Outer Shell 1315 may optionally include inner shell 1316 therein. In one embodiment, the inner shell at least partially surrounds residual limb 1310. Also, inner shell 1316 may include a discontinuity with side edges, wherein as prosthetic system 1307 applies force about residual limb 1307, the side edges of inner shell 316 move in opposite directions relative to each other.

Outer shell 1315 may optionally include a base component 1380 at the bottom of outer shell 1315. Based component 140 may be similar to base component 140 described above. Base component 1380 may close prosthetic system 1307 on a bottom. Base component 1380 may completely (like a cap) or partially close prosthetic system 30 on a bottom.

In one embodiment, optional artificial leg 1390 may be coupled (directly or via an intermediary structure) to base component 1380. In another embodiment, artificial leg 1390 is excluded, and prosthetic system 1307 is used to provide post operative compression.

One embodiment of the present invention extends from residual limb 1310 upwards, past greater trochanter 350

In one exemplary embodiment of the present invention, when outer shell 1315 is placed on residual limb 1310, outer shell 1315 encloses residual limb 1310 without enclosing either iscial tuberosities.

In one exemplary embodiment, prosthetic system 1307 is prevented from applying direct pressure to either ischium.

In one exemplary embodiment, prosthetic system 1307 provides uniform support to residual limb 1310 by providing uniform pressure about the soft tissue around residual limb 1310. This pressure is also referred to as hydrostatic pressure. This pressure may be modified by changing, for example, the amount of tightening of attachment devices 1370.

In one exemplary embodiment, when outer side 1371 extends above greater trochanter 350, outer side 1371 curves inward (i.e. towards pelvis 1320).

Because of the manner in which prosthetic system 1307 is spaced relative to ischium 1325, a patient may have less discomfort than when the prior art prosthetic systems are in use. For example, in FIG. 40, ischium 1325 is within prosthetic system 1305 (i.e. ischium 1325 extends below top edge 1341) while in FIG. 41 ischium 1325 is outside of prosthetic system 1307 (i.e. ischium 1325 does not extend below top edge 1341) and in fact sits on the upper brim 1326. Furthermore, in FIG. 40, top edge 1341 is below illium 1330 while in FIG. 42, top edge 1352 is above greater trochanter 1350 (and may not only be above the greater trochanter but may reach the level of the ilium 1330; the socket is generally below the ilium and above the greater trochanter) The higher outer side 1371 and lower inner side 1372 (compared with FIG. 35) results in increased patient comfort, particularly when the patient is in a sitting position. This configuration also results in better gait stability and optimal prosthetic alignment on the limb when standing and ambulating.

Comparing FIGS. 41 and 42, in FIG. 41 brim 1341 is directly under ischium 1325 at the area of the brim 1326. In contrast in FIG. 42, upper brim 1341 is not directly below ischium 1325 and is not encompassing the iscium. In fact, in FIG. 42, there is space below ischium 1325 while in FIG. 41 the part of the brim 1326 under the iscium 1325 is directly below (and directly pressing against) ischium 1325. Also, in FIG. 41 top edge 1341 is below ilium 1330 while in FIG. 42 top edge 352 is above greater trochanter 1350 (and may also be at the same level as ilium 1330).

FIG. 43 is a perspective view of the apparatus shown in FIG. 42. The key difference between prior art and the current new device is the elimination of either i) enclosing the ischium or ii) sitting upon the ischium. This new device is below and off the ischium and uses hydrostatic compression forces to hold the limb and body weight up comfortably when standing and walking. With a thinner brim, that does not have an expanded shelf for the ischium to sit upon and which does not contact the ischium, this new socket is much more comfortable when sitting.

Figure 44:
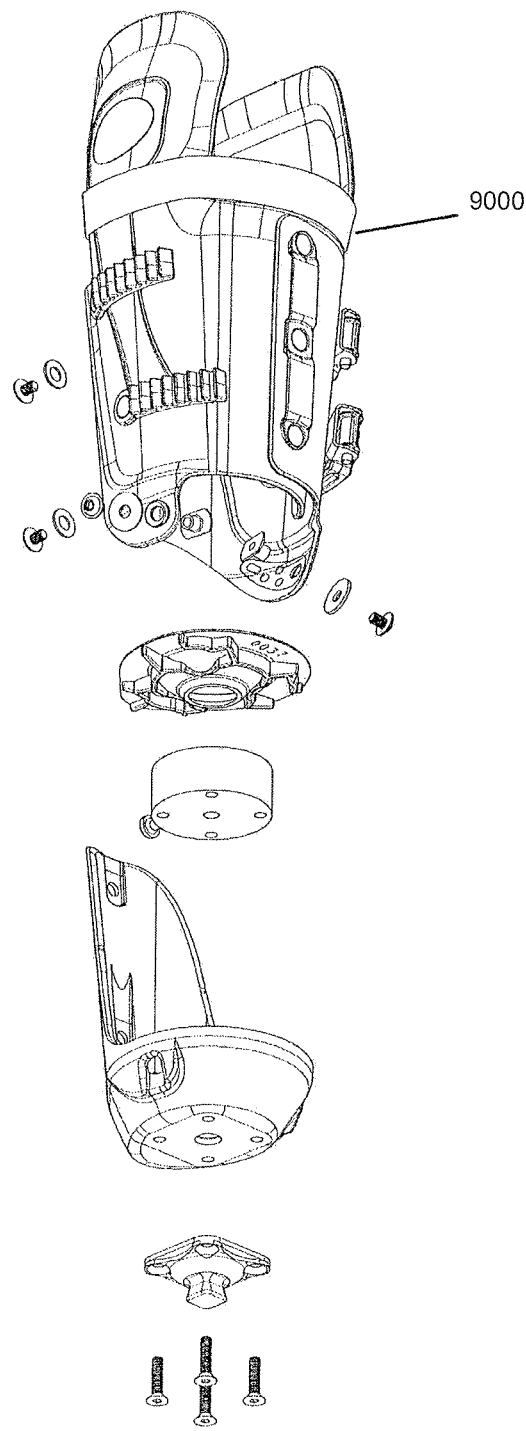
FIG. 44 is a perspective drawing of an exemplary embodiment of the present invention that includes features illustrated in FIG. 35 for illustrative purposes combined with an additional strap for stability.

FIG. 44 illustrates a further embodiment of the present invention. FIG. 44 illustrates the use of strap 9000 located about the prosthetic device. In particular, strap 9000 wraps around the top of the prosthetic device (for a below knee, transtibial, socket) and which provides considerable increase in knee stability and performance. Strap 900 may include webbing material that encircles the prosthetic device on the outside and hook and loop (e.g. Velcro brand) for attaching strap 9000 to itself. Strap 9000 reduces movement of the prosthetic device when walking and increases the grasp of the prosthetic device over the knee.

Figure 45:
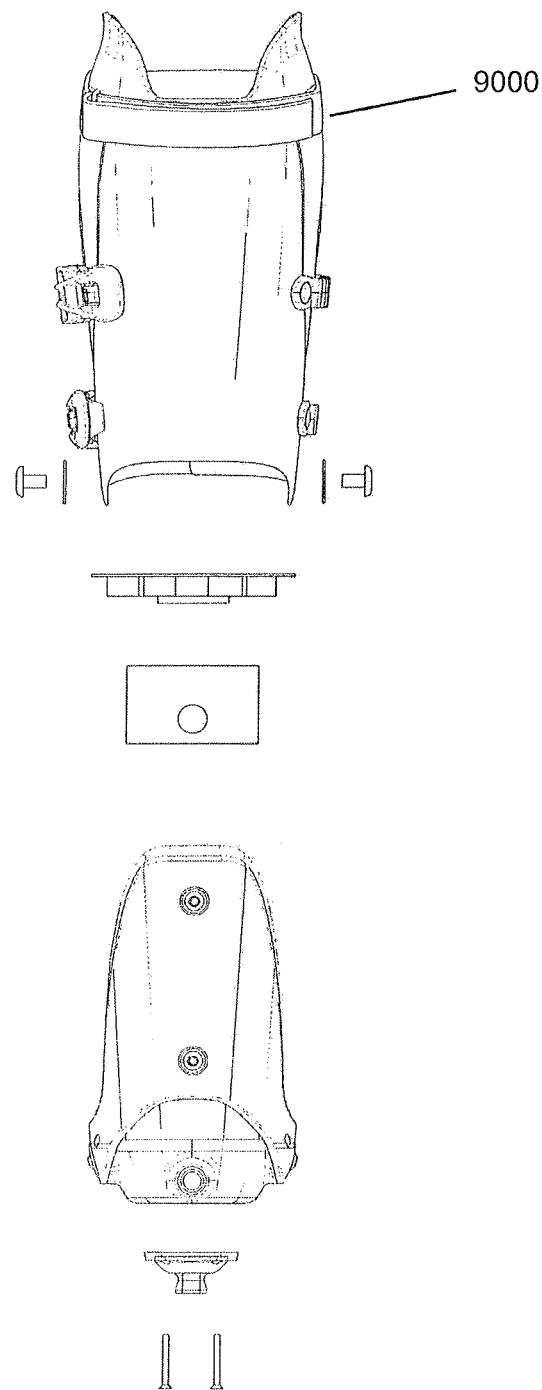
FIG. 45 is a front exploded view of the exemplary embodiment shown in FIG. 44.

FIG. 45 is an exploded front view of the exemplary embodiment shown in FIG. 44.

FIGS. 44 and 45 include features found in FIG. 35. These features are merely exemplary and are used to illustrate exemplary use of strap 9000.

Figure 48:
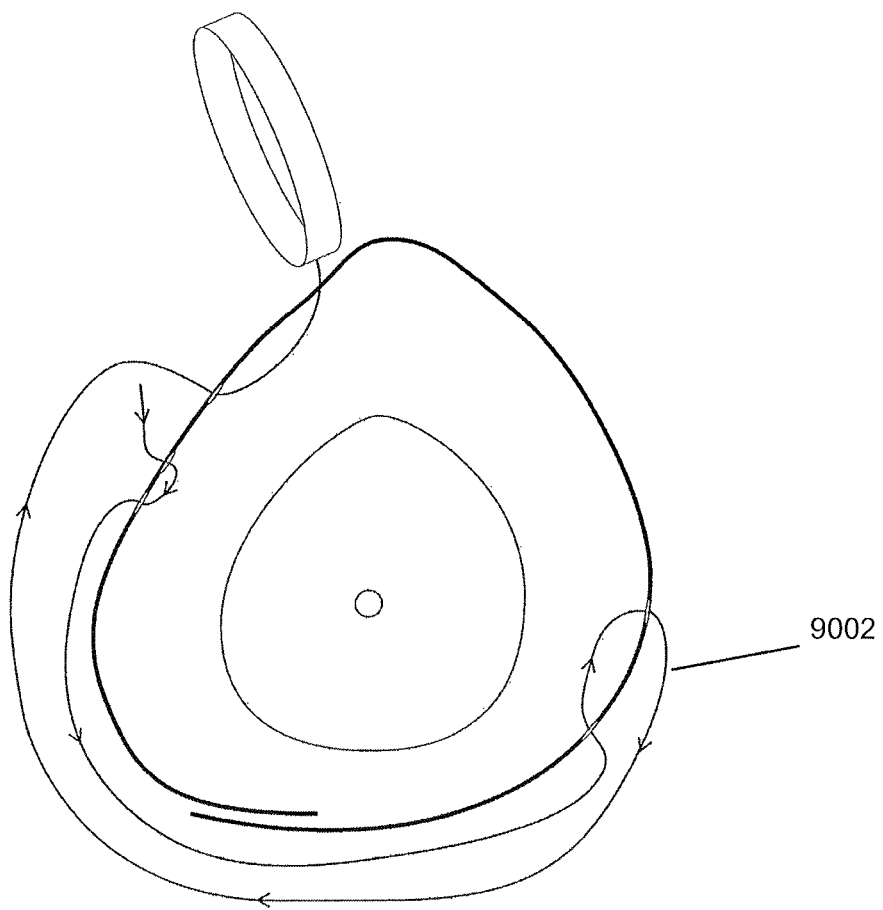
FIG. 48 is a top view of the exemplary embodiment shown in FIGS. 46 and 47.

FIGS. 46, 47, and 48 illustrate a further exemplary embodiment of the present invention in which pull-cords are used to tighten a prosthetic device about a residual limb. FIG. 46 is one side view of one side, FIG. 47 is another side view of another side, and FIG. 48 is a top view. As shown, two pull-cords 9002 and 9003 are threaded about a prosthetic device. Portions of each pull-cord 9002 and 9003 are either exterior to or interior to the prosthetic device. In each figure, the solid lines are exterior to the prosthetic device and the dotted lines are interior to the prosthetic device. One end of each pull cord 9002 and 9003 may be secured to the patient's leg while the other respective ends may be knotted together as shown. By pulling on one or both pull cords 9002, 9003 and then knotting them together the prosthetic device tightened about the residual limb.

In the exemplary embodiments shown in the drawings and discussed in the Detailed Description, various fasteners and adjustment components are used, including bolts, nuts, screws, washers, sets screws, etc. Persons skilled in the art will recognize that other types of fasteners and adjustment components could be used as well instead of those shown and discussed. Similarly, various types of components used for closing, tightening, and securing are illustrated and discussed, including straps, looped cables, laces, buckles, cable protuberances, buttons, snaps, clasps, clips, elastic components, ties, interlocking components, hook-and-loop fasteners, hook-and-eye fasteners, hook-shaped components, and any combination of these and other structures and devices. Persons skilled in the art will also recognize that other types of closing, tightening, and securing components also could be used as well instead of those shown and discussed.

Applicant's systems and devices include many other embodiments and variations thereof which are not illustrated in the drawings or discussed in the Detailed Description section. Those embodiments and variations, however, do fall within the scope of the appended claims and equivalents thereof.

Persons skilled in the art will recognize that the embodiments and variations illustrated in the drawings and discussed in the Detailed Description section do not disclose all of the possible arrangements of Applicant's systems and devices, and that other arrangements are possible. Accordingly, all such other arrangements are contemplated by Applicant's systems and devices, and are within the scope of the appended claims and equivalents thereof.

Persons skilled in the art also will recognize that many other embodiments incorporating Applicant's inventive concepts are possible, as well as many variations of the embodiments illustrated and described herein.

Although illustrated and described herein with reference to certain specific embodiments, Applicant's apparatus and devices are nevertheless not intended to be limited to the details shown. Rather, various modifications may be made in the details within the scope and range of equivalents of the claims without departing from the spirit of the invention.

320 flap
   330 flap
   1305 prior art prosthetic system
   1306 prior art prosthetic system
   1307 prosthetic system (exemplary embodiment)
   1310 residual limb
   1315 outer shell
   1316 inner shell (needs to be shown)
   1320 pelvis
   1325 ischium
   1326 brim
   1330 ilium
   1340 opening
   1341 upper edge
   1349 femur
   1350 greater trochanter
   1370 attachment devices
   1371 outer side
   1372 inner side
   1373 edge
   1374 edge
   1380 base component
   1390 artificial leg

What is claimed is:

1. An adjustable prosthesis system for a residual limb, comprising:
   - an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;
   - at least one closure component attached to the adjustable outer shell and adapted to adjust the width of the adjustable inner volume of the adjustable outer shell; and
   - an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted;
   - wherein the adjustable outer shell includes an exterior surface extending around said adjustable outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;
   - wherein tightening of the closure component causes the adjustable outer shell itself to increase tension at multiple locations around the adjustable outer shell towards its adjustable inner volume;
   - wherein the closure component is rigidly attached to one of the side ends of the adjustable outer shell, wherein tightening of the closure component creates pulling force where the closure component is rigidly attached to one of the side ends; and wherein tightening of the closure component applies force to the side ends in opposite directions, respectively, so that the side ends transition from a first amount of overlap to a second amount of overlap greater than the first amount of overlap.

2. An adjustable prosthesis system as in claim 1, wherein the adjustable outer shell comprises
   a first limb engaging panel, and
   a second limb engaging panel pivotally connected to the first limb engaging panel.

3. An adjustable prosthesis system as in claim 2, wherein at least a portion of the first limb engaging panel is rigid and at least a portion of the second limb engaging panel is not rigid.

4. An adjustable prosthesis system as in claim 1, further comprising:
   a connector comprising
      a plate coupled to the adjustable outer shell, and
      a plurality of connecting fasteners for adjustably coupling the plate to the bottom of the adjustable outer shell; and
   a coupling mechanism for coupling an artificial limb to the connector.

5. An adjustable prosthesis system as in claim 1, wherein the top edge of the adjustable outer shell varies in height, with a part of the top edge being higher than an other part of the top edge; and
   the closure component is below the top edge.

6. An adjustable prosthesis system as in claim 1, further comprising a suspension system connected to the adjustable outer shell.

7. An adjustable prosthesis system as in claim 1, wherein said at least one closure component is selected from a group consisting of buttons, snaps, clasps, clips, elastic components, buckles, laces, ties, interlocking components, hook-and-loop fasteners, hook-and-eye fasteners, hook-shaped components, looped wires, straps, and combinations thereof.

8. An adjustable prosthesis system as in claim 1, further comprising a pin suspension system with a locking pin.

9. An adjustable prosthesis system as in claim 8, further comprising a locking mechanism to lock and unlock the locking pin at a desired position.

10. An adjustable prosthesis system as in claim 9, further comprising a base plate adapted to guide the locking pin to a location adjacent the locking mechanism.

11. An adjustable prosthesis system as in claim 1, further comprising:
    a first stiffening member on a first side of the adjustable outer shell; and
    a second stiffening member on a second side of the adjustable outer shell substantially opposite the first side, wherein
    a proximal end of the adjustable outer shell extends above a knee portion of the residual limb,
    a proximal end of the inner liner extends above the proximal end of the adjustable outer shell, and
    the at least one closure component applies a force that moves the first and second stiffening members toward each other and moves an inner side of the adjustable outer shell and an inner side of the adjustable inner liner toward the residual limb,
    whereby at least a portion of the proximal end of the adjustable inner liner grasps the residual limb.

12. An adjustable prosthesis system as in claim 11 further comprising:
    a hook mechanism connected to an outer side of the adjustable outer shell,
    wherein the at least one closure component includes a buckle connected to the outer side of the adjustable outer shell, the buckle being adapted to removably connect with the hook mechanism.

13. An adjustable prosthesis system according to claim 1, wherein the adjustable outer shell is a socket with at least a partially closed end.

14. An adjustable prosthesis system according to claim 1, wherein the closure component is attached to one of the side ends.

15. An adjustable prosthesis system as in claim 1, wherein the adjustable inner liner has an upper end and a lower end, and at least a portion of the adjustable inner liner is deformable.

16. An adjustable prosthesis system as in claim 1, wherein a top edge along a front of the adjustable outer shell is higher than a top edge along a rear of the adjustable outer shell opposite the front of the adjustable outer shell.

17. An adjustable prosthesis system as in claim 1, wherein the adjustable inner liner defines a gap through which the residual limb is inserted, wherein the adjustable inner liner itself structurally supports the gap between opposing sides of the adjustable inner liner.

18. An adjustable prosthesis system for a residual limb, comprising:
    an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;
    at least one closure component attached to the adjustable outer shell and adapted to adjust the width of the adjustable inner volume of the adjustable outer shell; and
    an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted; and
    a connector adjustably coupled to the bottom of the adjustable outer shell and adapted for coupling an artificial limb to the connector;
    wherein the adjustable outer shell includes an exterior surface extending around said outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;
    wherein tightening of the closure component causes the adjustable outer shell itself to increase tension at multiple locations around the adjustable outer shell towards its adjustable inner volume;
    wherein the closure component is rigidly attached to one of the side ends of the adjustable outer shell, wherein tightening of the closure component creates pulling force where the closure component is rigidly attached to one of the side ends; and wherein tightening of the closure component applies force to the side ends in opposite directions, respectively, so that the side ends transition from a first amount of overlap to a second amount of overlap greater than the first amount of overlap.

19. An adjustable prosthesis system for a residual limb, comprising:
    an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;
    at least one closure component attached to the adjustable outer shell and adapted to adjust the width of the adjustable inner volume of the adjustable outer shell;
    an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted; and
    at least one pull cord attached to the adjustable outer shell and adapted to tighten the adjustable prosthesis system about the residual limb;
    wherein the adjustable outer shell includes an exterior surface extending around said adjustable outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;
    wherein tightening of the closure component causes the adjustable outer shell itself to increase tension at multiple locations around the adjustable outer shell towards its adjustable inner volume;
    wherein the closure component is rigidly attached to one of the side ends of the adjustable outer shell, wherein tightening of the closure component creates pulling force where the closure component is rigidly attached to one of the side ends; and
    wherein tightening of the closure component applies force to the side ends in opposite directions, respectively, so that the side ends transition from a first amount of overlap to a second amount of overlap greater than the first amount of overlap.

20. An adjustable prosthesis system as in claim 19, wherein the at least one closure component includes a locking mechanism or a safety latch.

21. An adjustable prosthesis system for a residual limb, comprising:
    an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;
    at least one closure component attached to the adjustable outer shell and adapted to adjust the width of the adjustable inner volume of the adjustable outer shell;
    an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted;
    a first stiffening member on a first side of the adjustable outer shell; and
    a second stiffening member on a second side of the adjustable outer shell substantially opposite the first side, wherein
    a proximal end of the adjustable outer shell extends above a knee portion of the residual limb,
    a proximal end of the inner liner extends above the proximal end of the adjustable outer shell, and
    the at least one closure component applies a force that moves the first and second stiffening members toward each other and moves an inner side of the adjustable outer shell and an inner side of the adjustable inner liner toward the residual limb,
    whereby at least a portion of the proximal end of the adjustable inner liner grasps the residual limb;
    wherein the adjustable outer shell includes an exterior surface extending around said adjustable outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;
    wherein tightening of the closure component causes the adjustable outer shell itself to increase tension at multiple locations around the adjustable outer shell towards its adjustable inner volume;
    wherein the closure component is rigidly attached to one of the side ends of the adjustable outer shell, wherein tightening of the closure component creates pulling force where the closure component is rigidly attached to one of the side ends;
    wherein tightening of the closure component applies force to the side ends in opposite directions, respectively, so that the side ends transition from a first amount of overlap to a second amount of overlap greater than the first amount of overlap; and
    wherein the at least one closure component comprises a buckle and a cable.

22. An adjustable prosthesis system as in claim 21, wherein the buckle includes a locking mechanism or a safety latch.

23. An adjustable prosthesis system for a residual limb, comprising:
    an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;

at least one closure component attached to the adjustable outer shell and adapted to adjust the width of the adjustable inner volume of the adjustable outer shell; and an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted;

wherein the adjustable outer shell includes an exterior surface extending around said adjustable outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;

wherein tightening of the closure component causes the adjustable outer shell itself to increase tension at multiple locations around the adjustable outer shell towards its adjustable inner volume;

wherein the closure component is rigidly attached to one of the side ends of the adjustable outer shell, wherein tightening of the closure component creates pulling force where the closure component is rigidly attached to one of the side ends;

wherein tightening of the closure component applies force to the side ends in opposite directions, respectively, so that the side ends transition from a first amount of overlap to a second amount of overlap greater than the first amount of overlap; and wherein the adjustable inner liner comprises:
an outer wall,
a flexible inner wall spaced apart from the outer wall and surrounding an inner cavity adapted to receive the residual limb,
an annular cavity between the outer wall and the flexible inner wall, the annular cavity adapted to receive a liquid foam or other material,
at least one removable inlet tube fluidly connected to the annular cavity adapted to transmit a flow of the liquid foam or other material into the annular cavity, and
at least one removable outlet tube fluidly connected to the annular cavity adapted to transmit at least a portion of the flow of the liquid foam or other material out of the annular cavity,
wherein the adjustable inner liner has an upper end and a lower end, and at least a portion of the adjustable inner liner is deformable.

24. An adjustable prosthesis system for a residual limb, comprising:
an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;
at least one closure component attached to the adjustable outer shell and adapted to adjust the width of the adjustable inner volume of the adjustable outer shell;
an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted;
a cup having an upper end connected to a distal end of the adjustable outer shell, an inner space, and a lower end;
a pyramid connector below and connected to the lower end of the cup and adapted to adjustably connect to a shank or an other prosthetic device; and
a clutch positioned in the inner space of the cup and adapted to connect to the pyramid connector, thereby sandwiching the lower end of the cup between the clutch and the pyramid connector;
wherein the adjustable outer shell includes an exterior surface extending around said adjustable outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;
wherein tightening of the closure component causes the adjustable outer shell itself to increase tension at multiple locations around the adjustable outer shell towards its adjustable inner volume;
wherein the closure component is rigidly attached to one of the side ends of the adjustable outer shell, wherein tightening of the closure component creates pulling force where the closure component is rigidly attached to one of the side ends; and
wherein tightening of the closure component applies force to the side ends in opposite directions, respectively, so that the side ends transition from a first amount of overlap to a second amount of overlap greater than the first amount of overlap.

25. An adjustable prosthesis system as in claim 24, further comprising:
a base plate located above the clutch and having an aperture for receiving a locking pin or other component.

26. An adjustable prosthesis system for a residual limb, comprising:
an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;
at least one closure component attached to the adjustable outer shell and adapted to adjust the width of the adjustable inner volume of the adjustable outer shell; and
an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted;
wherein the adjustable outer shell includes an exterior surface extending around said adjustable outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;

wherein tightening of the closure component causes the adjustable outer shell itself to increase tension at multiple locations around the adjustable outer shell towards its adjustable inner volume;

wherein the closure component is rigidly attached to one of the side ends of the adjustable outer shell, wherein tightening of the closure component creates pulling force where the closure component is rigidly attached to one of the side ends;

wherein tightening of the closure component applies force to the side ends in opposite directions, respectively, so that the side ends transition from a first amount of overlap to a second amount of overlap greater than the first amount of overlap;

wherein the adjustable inner liner is a friction suspension system comprising:

a sleeve adapted to be rolled onto the residual limb with an inner side of the sleeve adjacent an outer side of the residual limb, at least a portion of an outer side of the sleeve having a first textured material, and a flexible liner adapted to be wrapped around the sleeve when the sleeve has been rolled onto the residual limb with at least a portion of an inner side of the flexible liner adjacent at least a portion of the outer side of the sleeve, at least a part of said portion of the outer side of the sleeve having a second textured material, wherein the first textured material and the second textured material are adapted to meet and form a bond, and wherein the adjustable inner liner has an upper end and a lower end, and at least a portion of the adjustable inner liner is deformable.

27. An adjustable prosthesis system for a residual limb, comprising:

an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;

at least one closure component attached to the adjustable outer shell and adapted to adjust the width of the adjustable inner volume of the adjustable outer shell; and an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted;

wherein the adjustable outer shell includes an exterior surface extending around said outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;

wherein tightening of the closure component causes the adjustable outer shell itself to increase tension at multiple locations around the adjustable outer shell towards its adjustable inner volume;

wherein the closure component is rigidly attached to one of the side ends of the adjustable outer shell, wherein tightening of the closure component creates pulling force where the closure component is rigidly attached to one of the side ends;

wherein tightening of the closure component applies force to the side ends in opposite directions, respectively, so that the side ends transition from a first amount of overlap to a second amount of overlap greater than the first amount of overlap; and wherein a top edge along an outer side of the adjustable outer shell is higher than a top edge along an inner side of the adjustable outer shell opposite the outer side of the adjustable outer shell.

28. An adjustable prosthesis system as in claim 27, further comprising:

at least one pull cord attached to the adjustable outer shell and adapted to tighten the adjustable prosthesis system about the residual limb.

29. An adjustable prosthesis system for a residual limb comprising:

an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;

at least one closure component attached to the adjustable outer shell and adapted to adjust the width of the adjustable inner volume of the adjustable outer shell;

an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted;

a connector adjustably coupled to the bottom of the adjustable outer shell and adapted for coupling an artificial limb to the connector; and at least one pull cord attached to the adjustable outer shell and adapted to tighten the adjustable prosthesis system about the residual limb;

wherein the adjustable outer shell includes an exterior surface extending around said outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;

wherein tightening of the closure component causes the adjustable outer shell itself to increase tension at multiple locations around the adjustable outer shell towards its adjustable inner volume;

wherein the closure component is rigidly attached to one of the side ends of the adjustable outer shell, wherein tightening of the closure component creates pulling force where the closure component is rigidly attached to one of the side ends; and wherein tightening of the closure component applies force to the side ends in opposite directions, respectively, so that the side ends transition from a first amount of overlap to a second amount of overlap greater than the first amount of overlap.

30. An adjustable prosthesis system as in claim 29, wherein the at least one closure component comprises a buckle and a cable.

31. An adjustable prosthesis system for a residual limb, comprising:
- an adjustable outer shell having a top opening along a top edge that extends around said adjustable outer shell and into which the residual limb is insertable, a bottom surface opposite the top opening, and an adjustable inner volume, the adjustable inner volume having an outer shell width, the bottom surface of the adjustable outer shell configured to be weight bearing for the residual limb;
- at least one closure component attached to the adjustable outer shell and adapted to adjust the width of the adjustable inner volume of the adjustable outer shell;
- an adjustable inner liner in the adjustable outer shell, adapted to receive the residual limb, the adjustable inner liner having an inner liner width that adjusts responsive to adjustment of the outer shell width, the adjustable inner liner having a discontinuity bordered by two respective edges about a circumference thereof, wherein the edges move towards or away from each other as the inner liner width is adjusted; and
- a connector adjustably coupled to the bottom of the adjustable outer shell and adapted for coupling an artificial limb to the connector;
- wherein the adjustable outer shell includes an exterior surface extending around said outer shell, said exterior surface having side ends that overlap and extend between the top opening and the bottom surface, and that slide one relative to the other, wherein tightening of the closure component causes one of the side ends to slide relative to an other of the side ends in order to decrease the outer shell width;
- wherein tightening of the closure component causes the adjustable outer shell itself to increase tension at multiple locations around the adjustable outer shell towards its adjustable inner volume;
- wherein the closure component is rigidly attached to one of the side ends of the adjustable outer shell, wherein tightening of the closure component creates pulling force where the closure component is rigidly attached to one of the side ends;
- wherein tightening of the closure component applies force to the side ends in opposite directions, respectively, so that the side ends transition from a first amount of overlap to a second amount of overlap greater than the first amount of overlap; and
- wherein the at least one closure component comprises a buckle and a cable.

32. An adjustable prosthesis system as in claim 31, wherein the buckle includes a locking mechanism or a safety latch.

* * * * *